(12) United States Patent
Klumpp et al.

(10) Patent No.: US 7,608,599 B2
(45) Date of Patent: Oct. 27, 2009

(54) ANTIVIRAL PHOSPHORAMIDATES

(75) Inventors: Klaus Klumpp, Mountain View, CA (US); Joseph Armstrong Martin, Harpenden (GB); Christopher McGuigan, Cardiff (GB); David Bernard Smith, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 262 days.

(21) Appl. No.: 11/503,558

(22) Filed: Aug. 11, 2006

(65) Prior Publication Data

US 2007/0042988 A1    Feb. 22, 2007

Related U.S. Application Data

(60) Provisional application No. 60/708,726, filed on Aug. 15, 2005.

(51) Int. Cl.
| | | |
|---|---|---|
| C07H 19/04 | (2006.01) | |
| C07H 19/10 | (2006.01) | |
| C07H 19/044 | (2006.01) | |
| A01N 43/04 | (2006.01) | |
| A61K 31/70 | (2006.01) | |

(52) U.S. Cl. ............................ 514/43; 514/47; 514/48; 514/51; 536/26.1; 536/26.8; 536/26.9

(58) Field of Classification Search ........................ None
See application file for complete search history.

(56) References Cited

U.S. PATENT DOCUMENTS

| | | | | |
|---|---|---|---|---|
| 6,846,810 | B2 * | 1/2005 | Martin et al. | ................. 514/49 |
| 2003/0236216 | A1 | 12/2003 | Devos et al. | |
| 2004/0121980 | A1 * | 6/2004 | Martin et al. | ................. 514/50 |

FOREIGN PATENT DOCUMENTS

| | | |
|---|---|---|
| WO | WO 9010012 A1 | 9/1990 |
| WO | WO 01/18013 A1 | 3/2001 |
| WO | WO 01/74827 A1 | 10/2001 |
| WO | WO 02/100415 A2 | 12/2002 |

OTHER PUBLICATIONS

Curley, D., et al., "Synthesis and Anti-HIV Evaluation of some Phospamidate Derivatives of AZT," *Antiviral Res.* (1990) vol. 14 pp. 345-356.
Gudmundsson, K., et al., "Phosphoramidate Protides of 2',3'-Dideoxy-3'-fluoroadenosine and related Nucleosides with Potent Activity Against HIV and HBV, Nucleosides," *Nucleotides & Nucleic Acids* (2003) vol. 22(10) pp. 1953-1961.
McGuigan, C., et al. "Synthesis and Evaluation of some novel phosphoramidate derivatives of 3'-azido-3'deoxythymidine (AZT) as anti-HIV Compounds," *Antiviral Chem. & Chemother.* (1990) vol. 1(2) pp. 107-113.

McGuigan, C., et al. "Synthesis and anti-HIV Evaluation of some novel phosphoramidate derivatives of 3'-azido-3'deoxythymidine (AZT)," *Antiviral Res.* (1991) vol. 15(3) pp. 255-263.
McGuigan, C., et al. "Aryl phosphate derivatives of AZT retain activity against HIV1 in cell lines resistant to the action of AZT," *Antivir. Res.* (1992) vol. 17(4) p. 311.
McGuigan, C., et al., "Intracellular Delivery of Bioactive AZT Nucleotides by Arl Phosphate Derivatives of AZT," *J. Med. Chem.* (1993) vol. 36(8) p. 1048.
McGuigan, C., et al. "Synthesis and anti-HIV activity of some novel diaryl phosphate derivatives of AZT," *Antiviral Res.* (1994) vol. 24 pp. 69-77.
McGuigan, C., et al., "Aryl Phosphoramidate Derivatives of d4T have Improved Anti-HIV Efficacy in tissue Culture and May Act by the Generation of a Novel intracellular Metabolite," *J. Med. Chem.* (1996) vol. 39(8) p. 17848.
McGuigan, C., et al. "Application of Phosphoramidate Technology to Abacavir leads to Significant Enhancement of Antiviral Activity," *J. Med Chem.* (2005) vol. 48 p. 3504.
Saboulard, D., et al. "Characterization of the Activation Pathway of Phosphoramidate Triester Prodrugs of Stavudine and Zidovudine," *Mol. Pharmacol.* (1999) vol. 56 p. 693.
Siddiqui, A.D., et al. "The Presence of Substituents on the Aryl Moiety of the Aryl Phosphoramidate Derivative of d4T Enhances Anti-HIV Efficacy in Cell Culture," *J. Med Chem.* (1999) vol. 42(3) p. 393.
Siddiqui, A.D., et al., "Stereospecific chemical and enzymatic stability of phosphoramidate triester prodrugs of d4T in vitro," *Eur. J. Pharm. Sci.* (2004) vol. 22 p. 25.
Tobias,S.C. et. al., "Synthesis and Biological Studies of Novel Nucleoside Phosphoramidate Prodrug," *J. Med. Chem.* (2001) vol. 44 pp. 4475-4480.
Wagner, C.R. et. al., "Pronucleotides: Towards the In Vivo Delivery of Antiviral and Anticancer Nucleotides," *Medicinal Research Reviews*, NY, 2000, vol. 20 (6), pp. 417-450.

* cited by examiner

*Primary Examiner*—Traviss C McIntosh, III
(74) *Attorney, Agent, or Firm*—Brian L. Buckwalter

(57) ABSTRACT

The invention provides novel nucleoside compounds of formula I wherein $R^1$, $R^{2a}$, $R^{2b}$, $R^3$, $R^4$, $R^5$ $R^6$, $R^{8a}$, $R^9$ and $R^{10}$ are as defined herein which are useful for the treatment of Hepatitis C Virus (HCV) mediated diseases. The invention further provides methods for treatment or prophylaxis of HCV mediated diseases with compounds of formula I and pharmaceutical compositions comprising these compounds,

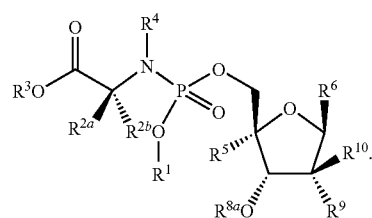

13 Claims, No Drawings

ANTIVIRAL PHOSPHORAMIDATES

CROSS REFERENCE TO RELATED APPLICATIONS

This application claims the benefit of priority to U.S. Ser. No. 60/708,726 filed Aug. 15, 2005 the contents of which are hereby incorporated in their entirety by reference.

FIELD OF THE INVENTION

The invention relates to the field of antiviral therapy and in particular to nucleoside derivatives for treating Hepatitis C Virus (HCV) mediated diseases. The invention provides novel chemical compounds, pharmaceutical compositions comprising these compounds, methods for treatment or prophylaxis of HCV mediated diseases employing said compounds in monotherapy or in combination therapy.

BACKGROUND

The invention relates to nucleoside derivatives that inhibitor HCV replicon RNA replication. In particular, the invention is concerned with the use of phosphoramidate esters of 4'-substituted nucleosides that inhibit subgenomic HCV RNA replication and pharmaceutical compositions containing said compounds.

Hepatitis C virus is the leading cause of chronic liver disease throughout the world (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae. The viruses and their replication.* In: *Fields Virology,* Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5' untranslated region (UTR), a long open reading frame encoding a polyprotein precursor of—approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia (X. Forns and J. Bukh, *Clinics in Liver Disease* 1999 3:693-716; J. Bukh et al., *Semin. Liv. Dis.* 1995 15:41-63).

Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently there are a limited number of approved therapies available for the treatment of HCV infection. Existing therapies and new therapies currently in development for treating HCV and inhibition of HCV NS5B polymerase have been reviewed: R. G. Gish, *Sem. Liver. Dis.,* 1999 19:5; Di Besceglie, A. M. and Bacon, B. R., Scientific American, October: 1999 80-85; G. Lake-Bakaar, *Current and Future Therapy for Chronic Hepatitis C Virus Liver Disease,* Curr. Drug Targ. Infect. Dis. 2003 3(3):247-253; P. Hoffmann et al., *Recent patents on experimental therapy for hepatitis C virus infection* (1999-2002), *Exp. Opin. Ther. Patents* 2003 13(11): 1707-1723; M. P. Walker et al., *Promising Candidates for the treatment of chronic hepatitis C, Exp. Opin. Investing. Drugs* 2003 12(8):1269-1280; S.-L. Tan et al., *Hepatitis C Therapeutics: Current Status and Emerging Strategies, Nature Rev. Drug Discov.* 2002 1:867-881; J. Z. Wu and Z. Hong, *Targeting NS5B RNA-Dependent RNA Polymerase for Anti-HCV Chemotherapy, Curr. Drug Targ.-Infect. Dis.* 2003 3(3):207-219. The development of resistance by HCV strains along with existing strains which are refractive to current therapy make new anti-HCV compounds very desirable.

A number of potential molecular targets for drug development as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome. Consequently, this enzyme has elicited significant interest among medicinal chemists. Nucleoside inhibitors of RNA polymerase can act either as a chain terminator during DNA synthesis or as a competitive inhibitor which interferes with nucleotide binding to the polymerase. To function as a chain terminator the nucleoside analog must be taken up be the cell and converted in vivo to a triphosphate to compete for the polymerase nucleotide binding site. The required conversion of nucleosides to the corresponding triphosphate is commonly mediated by cellular kinases imparting additional structural requirements on a potential nucleoside polymerase inhibitor. This also limits the direct evaluation of nucleosides as inhibitors of HCV replication to cell-based assays. Modification of the furanose ring of nucleosides has afforded compounds with anti-viral activity. Modification of the 2'- and 3'-positions of the sugar ring has been extensively investigated. Modification of the 4'-position of the furanose ring has been explored to a lesser extent because of the difficulties associated with introduction of substituents at this position.

Maag et al. (*J. Med. Chem.* 1992 3 5:1440-1451) disclose the synthesis of 4'-azido-2-deoxyribonucleosides and 4-azido nucleosides. C. O'Yang et al. (*Tetrahedron Lett.* 1992 33(1): 37-40 and 33(1):41-44) disclose the synthesis 4'-cyano, 4'-hydroxymethyl- and 4'-formyl substituted nucleosides. These compounds were evaluated as anti-HIV compounds.

In WO02/100415 published Dec. 19, 2002 (US 2003/0236216 A1), R. R. Devos et al. disclose 4'-substituted nucleoside compounds that exhibit anti-HCV activity. Four compounds explicitly identified include the 4'-azido compound, 1a, the 4'-ethynyl compound 1b, the 4'-ethoxy compound 1c and the 4'-acetyl compound 1d. Other exemplified modifications of the ribose moiety exemplified include the 2'-deoxy 2a derivative, 3'-deoxy derivative 2b, the 3'-methoxy derivative 2e, the 3'-fluoro derivative 2c and the 2',3'-difluoro derivative 2d. In WO2004/046159 published Jun. 3, 2004 (now U.S. Pat. No. 6,846,810), J. A. Martin et al. disclose mono-, di-, tri- and tetra-acyl prodrugs of 1a useful for treating HCV-mediated diseases. Both U.S. applications are hereby incorporated by reference in their entirety.

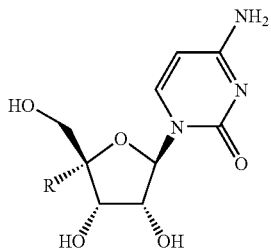

1a: R = N$_3$
1b: R = ethynyl
1c: R = OEt
1d: R = C(=O)Me

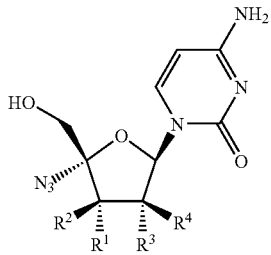

2a: R$^1$ = OH, R$^2$ = R$^3$ = R$^4$ = H
2b: R$^3$ = OH, R$^1$ = R$^2$ = R$^4$ = H
2c: R$^3$ = OH, R$^2$ = F, R$^1$ = R$^4$ = H
2d: R$^1$ = R$^2$ = H, R$^3$ = R$^4$ = F
2e: R$^1$ = OMe, R$^3$ = OH, R$^2$ = R$^4$ = H

Y.-H. Yun et al. (*Arch. Pharm. Res.* 1985 18(5):364-35) disclose the synthesis and antiviral activity of 4'-azido-2'-deoxy-2'-fluoro-arabinofuranosyl nucleosides (3: R=H, Me and Cl).

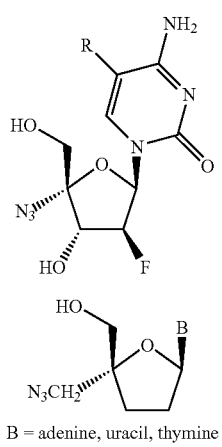

3

B = adenine, uracil, thymine

4

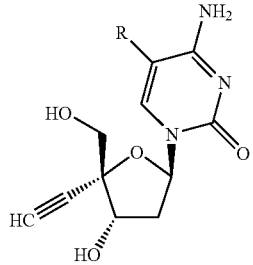

5

G. S. Jeon and V. Nair (*Tetrahedron* 1996 52(39): 12643-50) disclose the synthesis 4'-azidomethyl-2',3'-deoxyribonucleosides 4 (B=adenine, thymine and uracil) as HIV reverse transcriptase inhibitors.

I. Sugimoto et al. (*Bioorg. Med. Chem. Lett.* 1999 9:385-88) disclosed the synthesis and the HIV and H. simplex bioassay of 4'-ethynyl-2'-deoxycytidine (5) and other two-carbon substituents at the 4'-position. T. Wada et al. (*Nucleosides & Nucleotides* 1996 15 (1-3):287-304) disclose the synthesis and anti-HIV activity of 4'-C-methyl nucleosides.

In WO02/18404 published Mar. 7, 2002, R. Devos et al. disclose novel and known purine and pyrimidine nucleoside derivatives and their use as inhibitors of subgenomic HCV replication and pharmaceutical compositions containing said nucleoside derivatives. The compounds disclosed consist of nucleosides with substituted purine and pyrimidine bases.

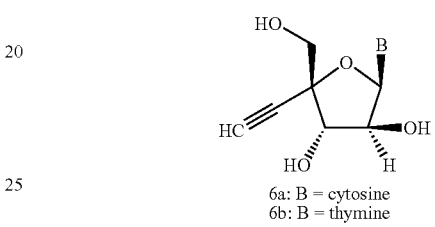

6a: B = cytosine
6b: B = thymine

H. Ohrui et al. (*Antimicrobial Agents and Chemother.* 2001 45(5):1539-1546; see also S. Koghgo et al., *Tennen Yuki Kagobutsu Toronkai Koen Yoshishu* 2000 42:835 (Chem. Abs. 2001:102156 and H. Ohrui et al. WO2000069876 published Nov. 23, 2000) disclose the synthesis and anti-HIV activity of 4'-C-ethynyl-β-D-arabino- and 4'-C-ethynyl-2'-deoxy-β-D-ribo-pentofuranosyl pyrimidines and -purines. 4-Ethynylcytarabine (6a) exhibits good anti-HIV activity while the corresponding nucleoside wherein the base was thymine 6b was inactive. Several 4'-C-ethylnyl-2'-deoxy-β-D-ribopentofuranosyl pyrimidines and -purines were potent inhibitors of HIV reverse transcriptase (HIV-RT).

K. Kitano et al. (Tetrahedron 1997 53(39):13315-13322) disclose the synthesis 4'-fluoromethyl 2-deoxy-D-erythro-, ribo- and arabino-pentofuranosyl cytosines and anti-neoplastic activity.

4'-Azidocytidine, 4'-azidouridine, 4'-ethynylcytidine, 4'-ethynyluridine, 4'azido-arabinose (see e.g. U.S. Ser. No. 60/603,778 which is incorporate by reference in its entirety), 4'-(Z-2-chlorovinyl)cytidine and 4'-(Z-2-chlorovinyl)uridine have exhibited activity against HCV and Flaviviridiae in cell culture or phosphorylated analogs were active against HCV polymerase in vitro. However, more potent compounds are desirable to provide safe therapeutically effective levels in vivo. Surprisingly, certain phosphoramidate derivatives have now been found to exhibit useful biological activity against Flaviviridae.

Although nucleoside derivatives have proven to be effective inhibitors of HCV polymerase, their practical utility is often limited by two factors. Firstly, suboptimal physical properties and poor pharmacokinetics frequently limit the intracellular concentration of the nucleoside derivative. The present invention relates to phosphoramidate derivatives of 4'-substituted nucleosides compounds with improved physiochemical and pharmacokinetic properties. These derivatives more efficiently permeate the intestinal mucosa and ultimately are transported into the cell. These "pronucleotides" enhance biological activity, bioavailability or stability of the parent nucleotide (for reviews, see e.g., R. J. Jones and N. Bischofberger, *Antiviral Res.* 1995 27; 1- 15 and C. R. Wagner et al., *Med. Res. Rev.* 2000 20:417-451).

Secondly, if the prodrug successfully penetrates an infected cell and is converted to the parent nucleoside, the biologically activity of these compounds depends upon kinase-mediated phorsphorylation to generate the nucleoside triphosphate. Chemically modified nucleosides that are effective enzyme inhibitors are frequently poor substrates for endogenous nucleoside kinases resulting in the inefficient product of the triphosphate. Furthermore, cells with low levels of nucleoside kinases are unable to phosphorylate the nucleoside analog. Formation of the monophosphate by a nucleoside kinase is normally rate-limiting and the second and third phosphorylations are less sensitive to modifications to the nucleoside.

Aryloxy phosphoramidate derivatives 7a afford a mechanism to overcome both problems. The phosphate moiety is masked with neutral lipophilic groups to obtain a suitable partition coefficient to optimize uptake and transport into the cell. Enzyme-mediated hydrolysis of the ester produces a nucleoside monophosphate 7e wherein the rare limiting initial phosphorylation is unnecessary. (Scheme I) C. McGuigan et al., *Antiviral Res.* 1992 17(4):311-321; *Antiviral. Res.* 1991 15:255-263; *J. Med. Chem.* 1993 36(9):1048-1052; *Antiviral Res.* 1994 24:69-77; *J. Med. Chem.* 1996 39:1748-1753; *Bioorg. Med. Chem. Lett.* 1996 6:2359-2361; P. Franchetti et al., *J. Med. Chem.* 1994 37:3534-3541; G. Valette et al., *J. Med. Chem.* 1996 39:1981-1990; J. Balzarini et al., *FEBS Lett.* 1997 410: 324-328; D. Saboulard et al., *Mol. Pharmacol.* 1999 56:693-704; A. D. Siddiqui et al., *Bioorg. Med. Chem. Lett.* 1999 9:2555-2260; S. C. Tobias and R. F. Borch *J. Med. Chem.* 2001 44:4475-4480; K. S. Gudmundsson et al., *Nucleosides, Nucleotides & Nucleic Acids* 2003 22(10): 1953-1961; D. Siccardi et al., *Eur. J Pharm. Sci.* 2004 22:25-31.

Phosphoramidate diesters of nucleoside compounds have been reported including AZT (zidovudine), d4T (stauvidine), FudR (5-fluorodeoxyuridine), 2'-deoxyuridine, thymidine, d4A (2',3'-didedehydro-2',3'-dideoxyadenosine), isoddA (2',3'-dideoxy-3'-oxoadensoine), FLT (alovudine, 3-deoxy-3-fluorothymidine), ddC (2',3'-dideoxycytosine), ddA (dideoxyadenosine), hypoxallene, 2',3'-dideoxy-3'-thiacytidine (3TC) and Ara-C (Wagner, id., p. 438).

SUMMARY OF THE INVENTION

The present invention is directed toward novel phosphoramidate derivatives of 4'-substituted nucleoside compounds that inhibit HCV polymerase, methods of treating a disorder mediated by HCV with said compounds and pharmaceutical compositions containing said compounds Compounds of the present invention possesses a structure according to formula I Scheme 1

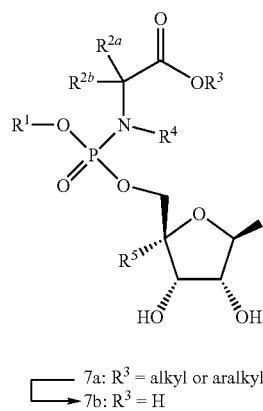

7a: $R^3$ = alkyl or aralkyl
7b: $R^3$ = H

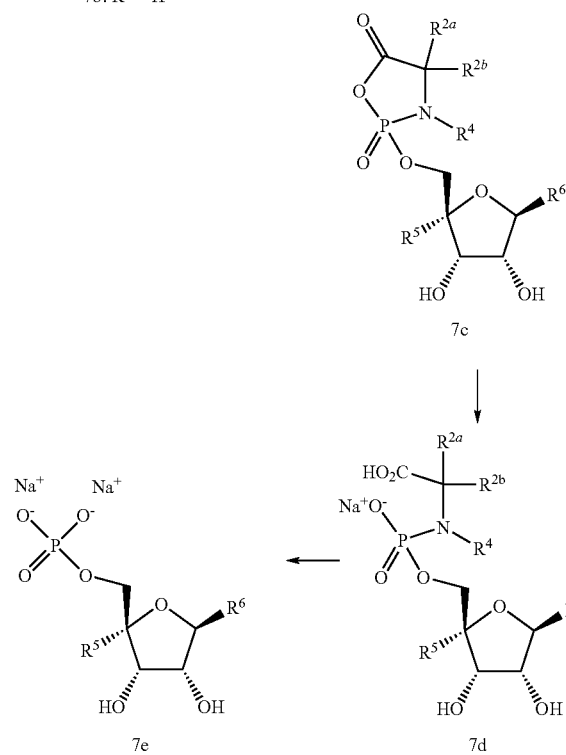

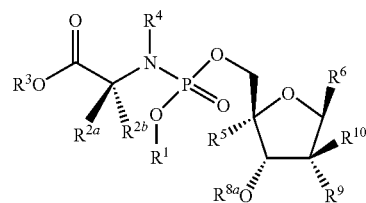

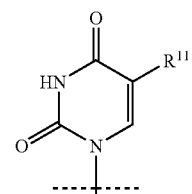

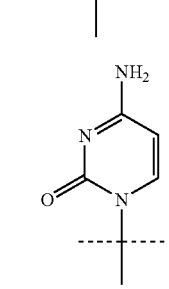

$R^5$ is H or a substituent
$R^6$ is cytidine, uridine or a 5-substituted derivative thereof -continued

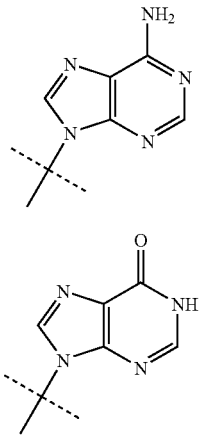

wherein:
R$^1$ is hydrogen or aryl wherein said aryl is phenyl or naphthyl optionally substituted with one to three substituents independently selected from the group consisting of C$_{1-6}$ alkyl, C$_{2-6}$ alkenyl, C$_{2-6}$ alkynyl, C$_{1-6}$ alkoxy, halogen, C$_{1-6}$ haloalkyl, —N(R$^{1a}$)$_2$, C$_{1-6}$ acylamino, —NHSO$_2$C$_{1-6}$ alkyl, —SO$_2$N(R$^{1a}$)$_2$, —SO$_2$C$_{1-6}$ alkyl, COR$^{1b}$, nitro and cyano;
R$^{1a}$ is independently hydrogen or C$_{1-6}$ alkyl;
R$^{1b}$ is —OR$^{1a}$ or —N(R$^{1a}$)$_2$;
R$^{2a}$ and R$^{2b}$ are (i) independently selected from the group consisting of hydrogen, C$_{1-10}$ alkyl, —(CH$_2$)$_r$(NR$^{1a}$)$_2$, C$_{1-6}$ hydroxyalkyl, —CH$_2$SH, —(CH$_2$)$_2$S(O)$_p$Me, —(CH$_2$)$_3$NHC(=NH)NH$_2$, (1H-indol-3-yl)methyl, (1H-imidazol-4-yl)methyl, —(CH$_2$)$_m$COR$^{1b}$, aryl and aryl C$_{1-3}$ alkyl, said aryl groups optionally substituted with a group selected from the group consisting of hydroxyl, C$_{1-10}$ alkyl, C$_{1-6}$ alkoxy, halogen, nitro and cyano; (ii) R$^{2a}$ is hydrogen and R$^{2b}$ and R$^4$ together are (CH$_2$)$_3$; (iii) R$^{2a}$ and R$^{2b}$ together are (CH$_2$)$_n$; or, (iv) R$^{2a}$ and R$^{2b}$ both are C$_{1-6}$ alkyl;
R$^3$ is hydrogen, C$_{1-10}$ alkyl, C$_{1-10}$ haloalkyl, aryl or aryl-C$_{1-3}$ alkyl wherein said aryl is phenyl;
R$^4$ is hydrogen, C$_{1-3}$ alkyl, or R$^{2b}$ and R$^4$ together are (CH$_2$)$_3$;
R$^5$ is azide, C≡CH or -(Z)-CH=CHCl;
R$^6$ is A, B, C or D wherein R$^{11}$ is hydrogen or C$_{1-3}$ alkyl;
R$^7$ is hydrogen, methyl, halomethyl or halogen;
either
 (a) R$^9$ is OR$^{8b}$ and R$^{10}$ is hydrogen wherein R$^{8a}$ and R$^{8b}$ are (i) independently hydrogen, benzoyl or C$_{1-4}$ acyl or (i) together R$^{8a}$ and R$^{8b}$ are C(Me)$_2$, C(CH$_2$)$_4$, CHPh, or
 (b) R$^9$ is hydrogen and R$^{10}$ is OR$^{8b}$ wherein R$^{8a}$ and R$^{8b}$ are independently hydrogen or C$_{1-6}$ acyl;
m is 0 to 3;
n is 4 or 5;
p is 0 to 2;
r is 1 to 6; and, pharmacologically acceptable salts thereof.

DETAILED DESCRIPTION OF THE INVENTION

In one embodiment of the present invention there is provided a compound according to formula I wherein I, A, B, C, D, R$^1$, R$^{1a}$, R$^{1b}$, R$^{2a}$, R$^{2b}$, R$^3$, R$^4$, R$^5$, R$^6$, R$^7$, R$^{8a}$, R$^{8b}$, R$^9$, R$^{10}$, m, n, p and r are as defined hereinabove and pharmaceutically acceptable salts thereof.

In one embodiment of the present invention there is provided a compound according to formula I wherein R$^{11}$ is hydrogen and R$^3$ is R$^3$ is hydrogen, C$_{1-10}$ alkyl, aryl or aryl-C$_{1-3}$ alkyl wherein said aryl is phenyl; I, A, B, C, D, R$^1$, R$^{1a}$, R$^{1b}$, R$^{2a}$, R$^{2b}$, R$^3$, R$^4$, R$^5$, R$^6$, R$^7$, R$^{8a}$, R$^{8b}$, R$^9$, R$^{10}$, m, n, p and r are as defined hereinabove and pharmaceutically acceptable salts thereof.

In another embodiment of the present invention there is provided a compound according to formula I wherein R$^{2a}$ and R$^{2b}$ are (i) independently hydrogen, methyl, iso-propyl, iso-butyl, sec-butyl, —CH$_2$OH, —CH(OH)CH$_3$, —CH$_2$SH, —CH$_2$CH$_2$S(O)$_p$Me, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene; (ii) R$^{2a}$ and R$^{2b}$ together are (CH$_2$)$_n$; or, (iii) R$^{2a}$ and R$^{2b}$ both are C$_{1-3}$ alkyl; R$^3$ is hydrogen, C$_{1-10}$ alkyl or benzyl; R$^9$ is OR$^{8b}$; R$^4$, R$^7$, R$^{8a}$, R$^{8b}$, R$^{10}$ and R$^{11}$ are hydrogen. Other Substituents not specifically limited in this embodiment are as defined in the summary of the invention. When R$^3$ is hydrogen it optionally can be replaced with a pharmaceutically acceptable cation.

In another embodiment of the present invention there is provided a compound according to formula I wherein R$^{2a}$ and R$^{2b}$ are (i) independently hydrogen, methyl, iso-propyl, iso-butyl, sec-butyl, —CH$_2$OH, —CH(OH)CH$_3$, —CH$_2$SH, —CH$_2$CH$_2$S(O)$_p$Me, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene; (ii) R$^{2a}$ and R$^{2b}$ together are (CH$_2$)$_n$; or, (iii) R$^{2a}$ and R$^{2b}$ both are C$_{1-3}$ alkyl; R$^3$ is hydrogen, C$_{1-10}$ alkyl or benzyl; R$^5$ is azide, R$^9$ is OR$^{8b}$; R$^4$, R$^7$, R$^{8a}$, R$^{8b}$, R$^{10}$ and R$^{11}$ are hydrogen. Other substituents not specifically limited in this embodiment are as defined in the summary of the invention. When R$^3$ is hydrogen it optionally can be replaced with a pharmaceutically acceptable cation.

In another embodiment of the present invention there is provided a compound according to formula I wherein R$^{2a}$ and R$^{2b}$ are (i) independently hydrogen, methyl, iso-propyl, iso-butyl, sec-butyl, —CH$_2$OH, —CH(OH)CH$_3$, —CH$_2$SH, —CH$_2$CH$_2$S(O)$_p$Me, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene; (ii) R$^{2a}$ and R$^{2b}$ together are (CH$_2$)$_n$; or, (iii) R$^{2a}$ and R$^{2b}$ both are C$_{1-3}$ alkyl; R$^3$ is hydrogen, C$_{1-10}$ alkyl or benzyl; R$^5$ is azide, R$^6$ is A or B, R$^9$ is OR$^{8b}$; R$^4$, R$^7$, R$^{8a}$, R$^{8b}$, R$^{10}$ and R$^{11}$ are hydrogen. Other substituents not specifically limited in this embodiment are as defined in the summary of the invention. When R$^3$ is hydrogen it optionally can be replaced with a pharmaceutically acceptable cation.

In another embodiment of the present invention there is provided a compound according to formula I wherein R$^{2a}$ and R$^{2b}$ are (i) independently hydrogen, methyl, iso-propyl, iso-butyl, sec-butyl, —CH$_2$OH, —CH(OH)CH$_3$, —CH$_2$SH, —CH$_2$CH$_2$S(O)$_p$Me, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene; (ii) R$^{2a}$ and R$^{2b}$ together are (CH$_2$)$_n$; or, (iii) R$^{2a}$ and R$^{2b}$ both are C$_{1-3}$ alkyl; R$^3$ is hydrogen, C$_{1-10}$ alkyl or benzyl; R$^5$ is azide; R$^6$ is C or D, R$^9$ is OR$^{8b}$; R$^4$, R$^7$, R$^{8a}$, R$^{8b}$, R$^{10}$ and R$^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein $R^{2a}$ is hydrogen and $R^{2b}$ is hydrogen, methyl, iso-propyl, iso-butyl, sec-butyl, —CH$_2$OH, —CH(OH)CH$_3$, —CH$_2$SH, —CH$_2$CH$_2$SMe, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene or (4-imidazolyl)methylene; $R^3$ is hydrogen, $C_{1-10}$ alkyl or benzyl; $R^5$ is azide or —C≡CH; $R^9$ is OR$^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein $R^{2a}$ is hydrogen and $R^{2b}$ is hydrogen, methyl, iso-propyl, iso-butyl, sec-butyl, —CH$_2$OH, —CH(OH)CH$_3$, —CH$_2$SH, —CH$_2$CH$_2$SMe, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene or (4-imidazolyl)methylene; $R^3$ is hydrogen, $C_{1-10}$ alkyl or benzyl; $R^5$ is azide or —C≡CH; $R^9$ is OR$^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with an alkylammonium cation.

In another embodiment of the present invention there is provided a compound according to formula I wherein $R^2$, is hydrogen and $R^{2b}$ is hydrogen, methyl, iso-propyl, iso-butyl, sec-butyl; $R^3$ is hydrogen, $C_{1-10}$ alkyl or benzyl, $R^5$ is azide or —C≡CH; $R^9$ is OR$^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein $R^2$, is hydrogen and $R^{2b}$ is hydrogen, methyl, iso-propyl, iso-butyl, sec-butyl; $R^3$ is hydrogen, $C_{1-10}$ alkyl or benzyl, $R^5$ is azide; $R^9$ is OR$^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein both $R^{2a}$ and $R^{2b}$ are Me or $R^{2a}$ and $R^{2b}$ together are (CH$_2$)$_n$ wherein n is 4; $R^3$ is hydrogen, $C_{1-10}$ alkyl or benzyl, $R^5$ is azide or —C≡CH; $R^9$ is OR$^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein both $R^{2a}$ and $R^{2b}$ are Me or $R^{2a}$ and $R^{2b}$ together are (CH$_2$), wherein n is 4; $R^3$ is hydrogen, $C_{1-10}$ alkyl or benzyl, $R^5$ is azide; $R^9$ is OR$^{8b}$; $R^4$, $R^7$, $R^{8a}$, $R^{8b}$, $R^{10}$ and $R^{11}$ are hydrogen.

In another embodiment of the present invention there is provided a compound according to formula I wherein $R^{2a}$ and $R^{2b}$ are (i) independently hydrogen, methyl, iso-propyl, iso-butyl, sec-butyl, —CH$_2$OH, —CH(OH)CH$_3$, —CH$_2$SH, —CH$_2$CH$_2$S(O)$_p$Me, —(CH$_2$)$_m$COR$^{1b}$ wherein m is 1 or 2, —(CH$_2$)$_r$—NH$_2$ where r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene; (ii) $R^{2a}$ and $R^{2b}$ together are (CH$_2$)$_n$; or, (iii) $R^{2a}$ and $R^{2b}$ both are $C_{1-3}$ alkyl; $R^3$ is hydrogen, $C_{1-10}$ alkyl or benzyl; $R^{10}$ is OR$^{8b}$; $R^4$, $R^7$, $R^{8a}$, $R^{8b}$ and $R^9$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein $R^2$, is hydrogen and $R^{2b}$ is hydrogen, methyl, iso-propyl, iso-butyl, sec-butyl, —CH$_2$OH, —CH(OH)CH$_3$, —CH$_2$SH, —CH$_2$CH$_2$SMe, —(CH$_2$)$_m$COR$^{1b}$ wherein m is 1 or 2, —(CH$_2$)$_r$—NH$_2$ wherein r is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene or (4-midazolyl)methylene; $R^3$ is hydrogen, $C_{1-10}$ alkyl or benzyl; $R^5$ is azide or —C≡CH; $R^{10}$ is OR$^{8b}$; $R^4$, $R^7$, $R^{8a}$, $R^{8b}$, $R^9$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein $R^{2a}$ is hydrogen and $R^{2b}$ is hydrogen, methyl, iso-propyl, iso-butyl, sec-butyl; $R^3$ is hydrogen, $C_{1-10}$ alkyl or benzyl; $R^5$ is azide or —C≡CH; $R^{10}$ is OR$^{8b}$; $R^4$, $R^7$, $R^{8a}$, $R^{8b}$, $R^9$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a compound according to formula I wherein both $R^{2a}$ and $R^{2b}$ are Me or $R^{2a}$ and $R^{2b}$ together are (CH$_2$)$_n$ wherein n is 4; $R^3$ is hydrogen, $C_{1-10}$ alkyl or benzyl; $R^5$ is azide or —C≡CH; $R^{10}$ is OR$^{8b}$; $R^4$, $R^7$, $R^{8a}$, $R^{8b}$, $R^9$ and $R^{11}$ are hydrogen. Other substituents not limited in this embodiment are as defined in the summary of the invention. When $R^3$ is hydrogen it optionally can be replaced with a pharmaceutically acceptable cation.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof.

In another embodiment of the present invention there is provided a method for treating a disease caused by hepatitis C virus (HCV) comprising treating a patient in need thereof with a therapeutically effective amount of a compound according to formula I wherein $R^9$ is OR$^{8b}$; $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a method for treating a disease caused by hepatitis C virus (HCV) comprising treating a patient in need thereof with a therapeutically effective amount of a compound according to formula I wherein $R^9$ is OR$^{8b}$; $R^{10}$ is hydrogen; $R^5$ is azide or —C≡CH. Other substituents not specifically limited in this embodiment are as defined in the summary of the invention. When $R^3$ is hydrogen it optionally can be replaced with a pharmaceutically acceptable cation.

In another embodiment of the present invention there is provided a method for treating a disease caused by hepatitis C virus (HCV) comprising treating a patient in need thereof with a therapeutically effective amount of a compound according to formula I wherein $R^{10}$ is $OR^{8b}$; $R^9$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a method for treating a disease caused by hepatitis C virus (HCV) comprising treating a patient in need thereof with a therapeutically effective amount of a compound according to formula I wherein $R^2$, is hydrogen and $R^{2b}$ is hydrogen, methyl, iso-propyl, iso-butyl, sec-butyl, —$CH_2OH$, —$CH(OH)CH_3$, —$CH_2SH$, —$CH_2CH_2SMe$, —$(CH_2)_mCOR^{1b}$ wherein m is 1 or 2, —$(CH_2)_r$—$NH_2$ wherein r is 3 or 4, —$(CH_2)_3$—$NHC(=NH)NH_2$, —$CH_2C_6H_5$, —$CH_2$-p-$C_6H_4$—$OH$, (3-indolinyl)methylene or (4-imidazolyl)methylene; $R^3$ is hydrogen, $C_{1-10}$ alkyl or benzyl; $R^5$ is azide or —$C\equiv CH$; $R^9$ is $OR^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a method for treating a disease caused by hepatitis C virus (HCV) comprising treating a patient in need thereof with a therapeutically effective amount of a compound according to formula I wherein $R^{2a}$ is hydrogen and $R^{2b}$ is hydrogen, methyl, iso-propyl, iso-butyl, sec-butyl; $R^3$ is hydrogen, $C_{1-10}$ alkyl or benzyl, $R^5$ is azide or —$C\equiv CH$; $R^9$ is $OR^{8b}$; $R^4$, $R^7$, $R^{8a}$, $R^{8b}$, $R^{10}$ and $R^{11}$ are hydrogen. Other substituents not specifically limited in this embodiment are as defined in the summary of the invention. When $R^3$ is hydrogen it optionally can be replaced with a pharmaceutically acceptable cation.

In another embodiment of the present invention there is provided a method for treating a disease caused by Flaviviridae virus comprising treating a patient in need thereof with a therapeutically effective amount of a compound according to formula I wherein I, Ia, Ib, $R^1$, $R^{1a}$, $R^{1b}$, $R^{2a}$, $R^{2b}$, $R^3$, $R^4$, $R^5$, $R^6$, $R^7$, $R^8$, $R^{8b}$, $R^9$, $R^{10}$, $R^{11}$, m, n, p and r are as defined in the summary of the invention and pharmaceutically acceptable salts thereof.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with at least one immune system modulator and/or at least one antiviral agent that inhibits replication of HCV.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with an immune system modulator selected from the group consisting of an interferon, interleukin, tumor necrosis factor and colony stimulating factor.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with an interferon, or a chemically derivatized interferon.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with PEGASYS® or PEG-INTRON®.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with at least one antiviral agent that inhibits replication of HCV.

In another embodiment of the present invention there is provided a method for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in combination with at least one antiviral agent that inhibits replication of HCV selected from the group consisting of an HCV protease inhibitor, another nucleoside HCV polymerase inhibitor, a non-nucleoside HCV polymerase inhibitor, an HCV helicase inhibitor, an HCV primase inhibitor and an HCV fusion inhibitor.

In another embodiment of the present invention there is provided a pharmaceutical composition for treating a disease caused by hepatitis C virus (HCV) comprising treating a patient in need thereof with a therapeutically effective amount of a compound according to formula I wherein A, B, C, D, $R^1$, $R^{1a}$, $R^{1b}$, $R^{2a}$, $R^{2b}$, $R^3$, $R^4$, $R^5$, $R^6$, $R^7$, $R^{8a}$, $R^{8b}$, $R^9$, $R^{10}$, $R^{11}$, m, n, p and r are as defined in the summary of the invention and pharmaceutically acceptable salts thereof, in admixture with at least one pharmaceutically acceptable carrier, diluent or excipient.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first and/or broadest definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The term "alkyl" as used herein denotes an unbranched or branched chain, saturated, monovalent hydrocarbon residue containing 1 to 10 carbon atoms unless otherwise designated. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkenyl" as used herein denotes an unsubstituted hydrocarbon chain radical having from 2 to 10 carbon atoms having one, or where possible, two olefinic double bonds unless designated otherwise. "$C_{2-10}$ alkenyl" as used herein refers to an alkenyl composed of 2 to 10 carbons. Examples are vinyl, 1-propenyl, 2-propenyl (allyl) or 2-butenyl (crotyl).

The term "alkynyl" as used herein denotes an unbranched or branched hydrocarbon chain radical having from 2 to 10 carbon atoms, and having one or where possible two triple bonds unless otherwise designated. $C_{2-10}$ alkenyl" as used herein refers to an alkenyl composed of 2 to 10 carbons. Examples are ethynyl, 1-propynyl, 2-propynyl, 1-butynyl, 2-butynyl or 3-butynyl.

The term "alkoxy" as used herein means an -O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "halogen" or "halo" as used herein means fluorine, chlorine, bromine, or iodine.

The term "haloalkyl" as used herein denotes a unbranched or branched chain alkyl group as defined above wherein 1, 2, 3 or more hydrogen atoms are replaced by a halogen. "$C_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term "arylcarbonyl" as used herein means a group of formula C(=O)R wherein R is an aryl group; the term "benzoyl" as used herein is an "arylcarbonyl" group wherein R is phenyl.

The term "acylamino" as used herein denotes a group of formula —NHC(=O)R wherein R is hydrogen or lower alkyl as defined herein The terms "hydroxyalkyl" and "alkoxyalkyl" as used herein denotes the radical R'R" where R' is a hydroxy radical or a alkoxy radical respectively and R" is alkylene as defined herein and the attachment point of the hydroxyalkyl radical will be on the alkylene radical. The term "alkylene" as used herein denotes a divalent saturated linear hydrocarbon radical of 1 to 6 carbon atoms or a branched saturated divalent hydrocarbon radical of 3 to 6 carbon atoms, unless otherwise indicated. Examples of alkylene radicals include, but are not limited to, methylene, ethylene, propylene, 2-methyl-propylene, butylene, 2-ethylbutylene. The term "hydroxyalkyl" herein also includes the threonine side chain —CH(OH)Me and $C_{3-8}$ homologs thereof.

The terms (1H-indol-3-yl)methyl and (1H-imidazol-4-yl) methyl as used herein refer to (a) and (b) respectively:

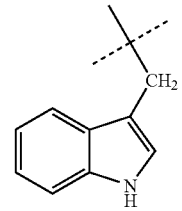

(a)

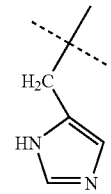

(b)

The term "aryl" as used herein denotes a phenyl or naphthyl radical optionally substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group.

The term "arylalkyl" or "aralkyl" as used herein denotes the radical R'R"—, wherein R' is an aryl radical as defined herein, and R" is an alkylene radical as defined herein with the understanding that the attachment point of the arylalkyl moiety will be on the alkylene radical. Examples of arylalkyl radicals include, but are not limited to, benzyl (aryl-$C_1$ alkyl), phenylethyl, 3-phenylpropyl.

The term "alkylammonium cation" as used herein refers to a radical $NR^1R^2R^3R^{4+}$ where $R^1$-$R^4$ are indendently hydrogen or alkyl.

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (G. Lake-Bakaar, Curr. Drug Targ. Infect Dis. 2003 3(3):247-253)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release,* 2001 72:217-224).

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes peginterferon-α-2a (PEGASYS®) and peginterferon-α-2b (PEGINTRON®).

A number of potential molecular targets for drug development as anti-HCV therapeutics have now been identified including, but not limited to, the NS2-NS3 autoprotease, the N3 protease, the N3 helicase and the NS5B polymerase. The RNS-dependent RNA polymerase is absolutely essential for replication of the single-stranded, positive sense, RNA genome. Combination therapy has proved a useful strategy in anti-viral therapy and compounds of the present invention can be used in combination with other NS5B polymerase inhibitors or with inhibitors of other viral targets.

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al., WO 01/47833, H. Hashimoto et al. WO 03/000254, P. L. Beaulieu et al., WO 03/020240 A2; P. L. Beaulieu et al., U.S. Pat. No. 6,448,281 B1; P. L. Beaulieu et al., WO 03/007945 A1); indoles, (P. L. Beaulieu et al., WO 03/0010141 A2); benzothiadiazines (D. Dhanak et al., WO 01/85172 A1; D. Dhanak et al., WO 03/037262 A2; K. J. Duffy et al., WO03/099801 A1, D.Chai et al., WO 2004/0526313, J. K. Pratt et al., WO 2004/041818 A1; J. K. Pratt et al., WO 2004/087577 A1), thiophenes, (C. K. Chan et al., WO 02/100851 A2); benzothiophenes (D. C. Young and T. R. Bailey, WO 00/18231); β-ketopyruvates (S. Attamura et al., U.S. Pat. No. 6,492,423 B1, A. Attamura et al., WO 00/06529); pyrimidines (C. Gardelli et al., WO 02/06246 A1); pyrimidinediones (T. R. Bailey and D. C. Young, WO 00/13708); triazines (K.-H. Chung et al., WO 02/079187 A1); rhodanine derivatives (T. R. Bailey and D. C. Young, WO 00/10573, J. C. Jean et al., WO 01/77091 A2); 2,4-dioxopyrans (R. A. Love et al., EP 256628 A2); phenylalanine derivatives (M. Wang et al., *J. Biol. Chem.* 2003 278:2489-2495).

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo [3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo [5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TB-DMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Phosphoramidate compounds of the present invention can be prepared by condensation of a 4'-substituted nucleoside with a suitably substituted phosphochloridate compound 12 in the presence of a strong base (Scheme 2). The nucleosides of the present invention typically contain an optionally substituted pyrimidine ($R^6$=A or B) or purine ($R^6$=C or D) and one of $R^9$ and $R^{10}$ is hydroxyl or acyloxy and the other of $R^9$ and $R^{10}$ is hydrogen. When $R^9$ is hydroxy, $R^8$ and $R^9$ are optionally part of a dioxolane ring. Examples of 4'-substituted nucleosides used to prepare compounds of the present invention can be found in Table 3, which is not intended to be limiting, and the scope of the nucleosides of the present invention can be found in the claims. The condensation can be carried out on the unprotected nucleoside (e.g., 13a-e; R. Devos et al. U.S. Pat. No. 6,784,166 filed Jun. 11, 2002; H. Ohrui et al. WO 2000069876 filed Nov. 11, 2000; E.-I. Kodama et al. *Antimicrob. Agents Chemother.* 2001 45(5): 1539-1546) or, alternatively, the 2',3'-hydroxy groups of the nucleoside can be protected as an acetonide (13f; J. A. Martin et al. US20040121980 filed Nov. 19, 2003) or other diol protecting group known in the art. Deprotection of a nucleoside after the condensation is carried out utilizing standard protocols for nucleic acid chemistry. General experimental procedures for the condensation are described in Examples 1 to 7.

Scheme 2

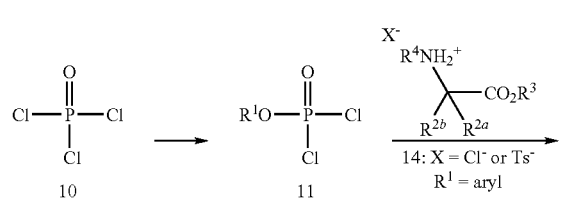

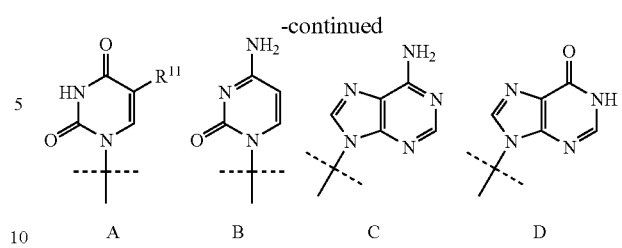

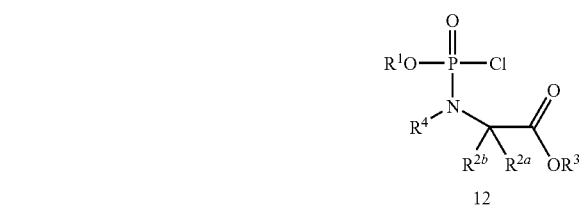

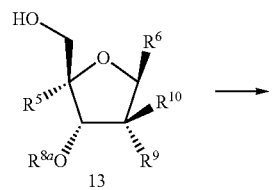

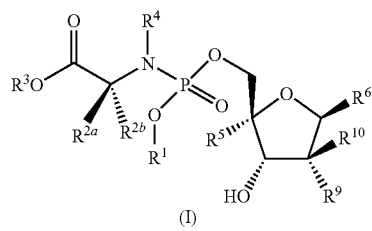

The requisite substituted phosphochloridate compounds 12 utilized to prepare compounds of the present invention are prepared by a two-step sequence comprising condensation of phosphorus oxychloride (10) with a suitably substituted phenol to afford an aryloxy phosphorodichloridates 11 (see Example 2) which are subsequently treated with a acid addition salt of an α-amino acid ester in the presence of TEA to afford an aryloxy phosphorochloridate 12 (for representative procedure see, e.g., D. Curley et al. *Antiviral Res.* 1990 14:345-356; C. McGuigan et al. *Antiviral Res.* 1992 17:311-321; McGuigan et al. *Antiviral Chem. Chemother* 1990 1(2): 107-113). Representative aryloxy phosphorodichloridates and aryloxy phosphorochloridates are listed in Tables 1 and 2 respectively.

TABLE 1

RO—P(=O)Cl$_2$

| Cpd. No. | R |
|---|---|
| 11a | $C_6H_5$— |
| 11b | 4-Cl—$C_6H_4$— |
| 11c | 3,4-$C_6H_3$— |
| 11d | 4-MeO—$C_6H_4$— |
| 11e | 4-Me—$C_6H_4$— |
| 11f | Br-2-naph[1] |
| 11g | 1-naph[2] |

[1] Br-2-naph = 1-bromo-naphth-2-yl
[2] 1-naph = naphth-1-yl

TABLE 2

| | $R^1$ | $R^{2a}$ | $R^{2b}$ | $R^3$ | $R^4$ | | X |
|---|---|---|---|---|---|---|---|
| 12a | $C_6H_5$— | H | H | $CH_2Ph$ | H | 14a | Cl$^-$ |
| 12b | $C_6H_5$— | H | H | Et | Me | 14b | |
| 12c | $C_6H_5$— | Me | H | Me | H | | |
| 12d | $C_6H_5$— | Me | H | Et | H | | |
| 12e | $C_6H_5$— | Me | H | i-Pr | H | | |
| 12f | $C_6H_5$— | Me | H | tert-Bu | H | 14f | Cl$^-$ |
| 12g | $C_6H_5$— | Me | H | CH(Et)Me | H | 14g | Cl$^-$ |
| 12h | $C_6H_5$— | H | Me | Et | H | | |
| 12i | $C_6H_5$— | H | Me | n-Bu | H | | |
| 12j | $C_6H_5$— | H | Me | t-Bu | H | 14j | Cl$^-$ |
| 12k | $C_6H_5$— | H | Me | CH(Me)Et | H | 14k | Tos$^-$ |
| 12l | $C_6H_5$— | H | Me | $C_{12}H_{25}$ | H | 14l | Tos$^-$ |
| 12m | $C_6H_5$— | H | Me | $CH_2Ph$ | H | 14m | Tos$^-$ |
| 12n | $C_6H_5$— | Me | Me | Et | H | 14n | Cl$^-$ |
| 12o | $C_6H_5$— | Me | Me | i-Pr | H | 14o | Cl$^-$ |
| 12p | $C_6H_5$— | Me | Me | $CH_2Ph$ | H | 14p | Cl$^-$ |
| 12q | $C_6H_5$— | $CH_2CHMe_2$ | H | Et | H | 14q | Cl$^-$ |
| 12r | $C_6H_5$— | $CH_2CHMe_2$ | H | i-Pr | H | | |

TABLE 2-continued

| | R¹ | R²ᵃ,R²ᵇ | | R³ | R⁴ | | |
|---|---|---|---|---|---|---|---|
| 12s | C₆H₅— | CH₂CHMe₂ | H | CH₂Ph | H | 14s | Tos⁻ |
| 12t | C₆H₅— | CH(Me)Et | H | Et | H | 14t | Cl⁻ |
| 12u | C₆H₅— | CH₂Ph | H | Et | H | 14u | Cl⁻ |
| 12v | C₆H₅— | CH₂Ph | H | i-Pr | H | 14v | Cl⁻ |
| 12w | C₆H₅— | CH₂Ph | H | CH₂Ph | H | | |
| 12x | C₆H₅— | (CH₂)₂SMe | H | Et | H | | |
| 12y | C₆H₅— | (CH₂)₂CO₂Et | H | Et | H | 14y | Cl⁻ |
| 12z | 4-Cl—C₆H₄— | Me | H | CH₂Ph | H | | |
| 12aa | 4-Cl—C₆H₄— | H | Me | CH₂Ph | H | | |
| 12ab | 4-Cl—C₆H₄— | CH₂CHMe₂ | H | Et | H | | |
| 12ac | 3,4-di-Cl—C₆H₃— | CH₂CHMe₂ | H | Et | H | | |
| 12ad | 3,4-di-Cl—C₆H₃— | H | Me | CH₂Ph | H | | |
| 12ae | 4-Me—C₆H₄— | Me | H | Et | H | | |
| 12af | 4-Me—C₆H₄— | Me | H | n-Bu | H | | |
| 12ag | 4-Me—C₆H₄— | CH₂CHMe₂ | H | Et | H | | |
| 12ah | 4-MeO—C₆H₄— | Me | H | CH₂Ph | H | | |
| 12ai | 4-MeO—C₆H₄— | CH₂CHMe₂ | H | Et | H | | |
| 12an | C₆H₅— | Me | H | CH₂Ph | H | | |
| 12ao | C₆H₅— | Me | Me | t-Bu | H | | |
| 12ap | C₆H₅— | H | Me | i-Pr | H | 14ap | Cl⁻ |
| 12aq | C₆H₅— | CHMe₂ | H | CH₂Ph | H | | |
| 12ar | Br-2-naph¹ | Me | H | CH₂Ph | H | | |
| 12as | 1-naph² | Me | H | CH₂Ph | H | | |

| | R¹ | R²ᵃ,R²ᵇ | R³ | R⁴ | | |
|---|---|---|---|---|---|---|
| 12aj | C₆H₅— | (CH₂)₄ | Et | H | 14aj | Cl⁻ |
| 12ak | C₆H₅— | (CH₂)₄ | i-Pr | H | | |
| 12al | C₆H₅— | (CH₂)₄ | CH₂Ph | H | 14al | Tos⁻ |

| | R¹ | R²ᵇ | R³ | R²ᵃ,R⁴ |
|---|---|---|---|---|
| 12am | C₆H₅— | H | Et | (CH₂)₃ |

¹Br-2-naph = 1-bromo-naphth-2-yl
²1-naph = naphth-1-yl

TABLE 3

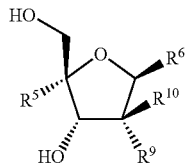

I

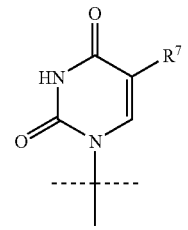

A

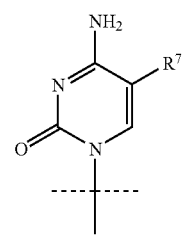

B

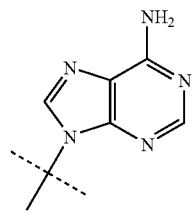

C

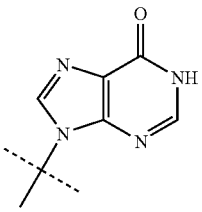

D

| Cpd. No. | R⁵ | R⁶ | R⁸ᵃ | R⁹ | R¹⁰ | R⁷ |
|---|---|---|---|---|---|---|
| 13a | —N₃ | A | H | HO | H | H |
| 13b | —N₃ | B | H | HO | H | H |
| 13c | —C≡CH | A | H | HO | H | H |
| 13d | —C≡CH | B | H | HO | H | H |
| 13e | (Z)—CH=CHCl | A | H | HO | H | H |
| 13f | —N₃ | B | —CMe₂O— | H | H | |
| 13g | —N₃ | B | H | H | HO | H |
| 13h | —N₃ | A | C(CH₂)₄ | H | H | |
| 13i | —N₃ | C | H | HO | H | — |
| 13j | —N₃ | D | H | HO | H | — |
| 13k | —N₃ | D | C(CH₂)₄ | H | — | |

Condensation of aryloxy phosphorochloridate 12 with a nucleoside 13 wherein $R^5$ is —$N_3$, —C≡CH or -(Z)-CH=CHCl, $R^6$ is optionally substituted uridine, cytidine, adenosine or inosine, $R^{8a}$ is hydrogen and one of $R^9$ and $R^{10}$ is hydroxyl and the other of $R^9$ and $R^{10}$ is hydrogen. When $R^{8a}$ is hydrogen and $R^9$ is hydroxyl the resulting 3',4'-diol can form an acetal or ketal protecting group. Treating a nucleoside with an aryloxy phosphoramidate in the presence of strong base affords the phosphoramidate derivatives of the invention (for representative procedures see, e.g. K. S. Gudmundsson, *Nucleosides, Nucleotides & Nucleic Acids* 2003 22(10):1953-1961). When $R^8$ and $R^9$ are protected hydroxyl groups, a subsequent deprotection step is required which steps are know in the art.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The term "amino acid" as used herein refers to naturally occurring αx amino carboxylic acids, as well as to optical isomers (enantiomers and diastereomers), synthetic analogs and derivatives thereof. α-Amino acids comprise a carbon atom bonded to a carboxyl group, an amino group, a hydrogen atom and a unique "side chain" group. The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. The side chains of naturally occurring amino acids include: hydrogen, methyl, iso-propyl, iso-butyl, sec-butyl, —$CH_2OH$, —CH(OH)$CH_3$, —$CH_2SH$, —$CH_2CH_2SMe$, —$(CH_2)_pCOR$ wherein R is —OH or —$NH_2$ and p is 1 or 2, —$(CH_2)_q$—$NH_2$ where q is 3 or 4, —$(CH_2)_3$—NHC(=NH)$NH_2$, —$CH_2C_6H_5$, —$CH_2$-p-$C_6H_4$—OH, (3-indolinyl)methylene, (4-imidazolyl)methylene.

Compounds of the present invention may have asymmetric centers located on the side chain of a carboxylic ester, amide or carbonate moiety that produce diastereomers when linked to the nucleoside. All stereoisomers of a side chain of compounds of the instant invention are contemplated, either in admixture or in pure or substantially pure form. The definition of the compounds according to the invention embraces all both isolated optical isomers enantiomers and their mixtures including the racemic form. The pure optical isomer can be prepared by stereospecific synthesis from α-D-ribose or the racemic form can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

Representative Compounds of the Invention

Examples of representative compounds encompassed by the present invention and within the scope of the invention are provided in Table I-IV. These examples and preparations which follow are provided to enable those skilled in the art to more clearly understand and to practice the present invention. They should not be considered as limiting the scope of the invention, but merely as being illustrative and representative thereof.

In general, the nomenclature used for the compounds in Table I-IV is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I

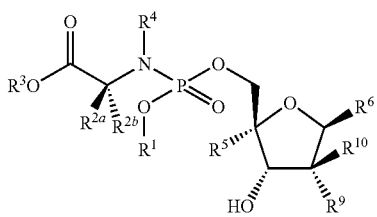

I

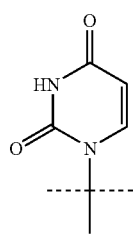

A

TABLE I-continued

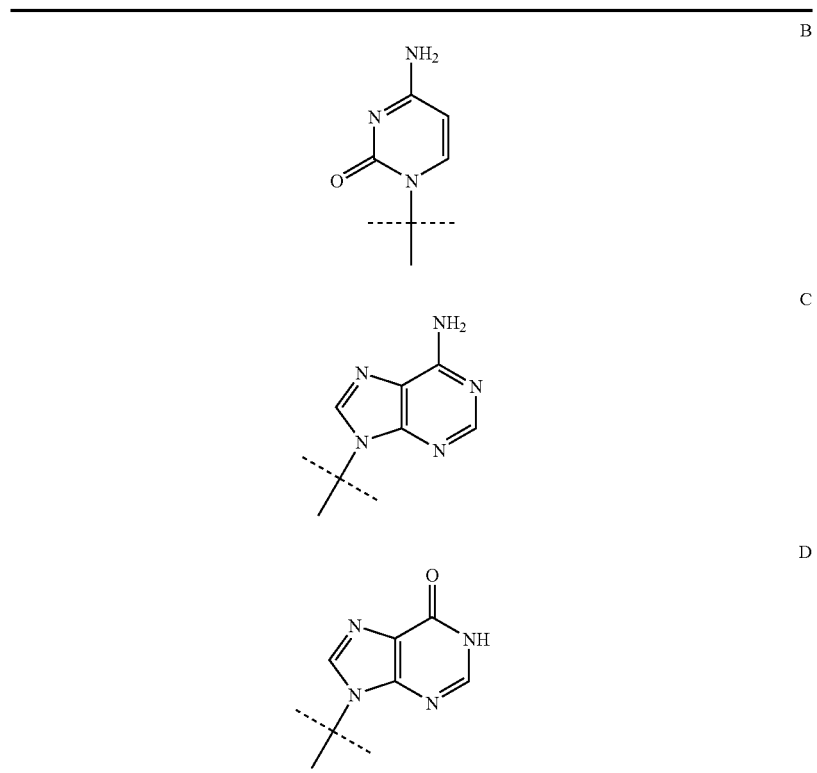

| No. | R$^1$ | R$^{2a}$ | R$^{2b}$ | I | R$^3$ | R$^4$ | R$^5$ | R$^6$ | R$^9$ | R$^{10}$ |
|---|---|---|---|---|---|---|---|---|---|---|
| I-1 | Ph | Me | H | S | Me | H | N$_3$ | B | OH | H |
| I-2 | Ph | CH$_2$Ph | H | S | Et | H | N$_3$ | B | OH | H |
| I-3 | Ph | Me | Me | — | CH$_2$Ph | H | N$_3$ | B | OH | H |
| I-4 | Ph | Me | Me | — | CH$_2$Ph | H | N$_3$ | A | OH | H |
| I-5 | Ph | CH$_2$CHMe$_2$ | H | S | Et | H | N$_3$ | A | OH | H |
| I-6 | Ph | Me | Me | — | Et | H | N$_3$ | A | OH | H |
| I-7 | Ph | CH$_2$Ph | H | S | CH$_2$Ph | H | N$_3$ | B | OH | H |
| I-8 | Ph | CH$_2$Ph | H | S | CH$_2$Ph | H | N$_3$ | A | OH | H |
| I-9 | Ph | CH$_2$Ph | H | S | i-Pr | H | N$_3$ | A | OH | H |
| I-10 | Ph | Me | Me | — | Et | H | N$_3$ | B | OH | H |
| I-11 | Ph | CH(Et)Me | H | S | Et | H | N$_3$ | B | OH | H |
| I-12 | Ph | Me | Me | — | i-Pr | H | N$_3$ | A | OH | H |
| I-13 | Pb | Me | H | S | CH$_2$Ph | H | N$_3$ | A | OH | H |
| I-14 | Ph | Me | H | S | i-Pr | H | N$_3$ | A | OH | H |
| I-15 | Ph | Me | Me | — | i-Pr | H | N$_3$ | B | OH | H |
| I-16 | 4-Cl-Ph | CH$_2$CHMe$_2$ | H | S | Et | H | N$_3$ | B | OH | H |
| I-17 | 3,4-di-Cl-Ph | CH$_2$CHMe$_2$ | H | S | Et | H | N$_3$ | B | OH | H |
| I-18 | Ph | CH$_2$Ph | H | S | i-Pr | H | N$_3$ | B | OH | H |
| I-19 | Ph | CH$_2$CHMe$_2$ | H | S | CH$_2$Ph | H | N$_3$ | B | OH | H |
| I-20 | Ph | Me | H | S | CH$_2$Ph | H | N$_3$ | B | OH | H |
| I-21 | Et$_3$NH$^+$ | Me | Me | — | Et | H | N$_3$ | B | OH | H |
| I-22 | Et$_3$NH$^+$ | Me | Me | — | Et$_3$NH$^+$ | H | N$_3$ | B | OH | H |
| I-23 | Ph | CH$_2$CO$_2$Et | H | S | Et | H | N$_3$ | B | OH | H |
| I-24 | Ph | Me | H | S | Et | H | N$_3$ | A | OH | H |
| I-25 | 4-Me-Ph | CH$_2$CHMe$_2$ | H | S | Et | H | N$_3$ | B | OH | H |
| I-26 | 4-MeO-Ph | CH$_2$CHMe$_2$ | H | S | Et | H | N$_3$ | B | OH | H |
| I-27 | Ph | CH$_2$CHMe$_2$ | H | S | Et | H | N$_3$ | B | OH | H |
| I-28 | Ph | Me | H | S | Me(Et)CH | H | N$_3$ | B | OH | H |
| I-29 | Ph | Me | H | S | tert-Bu | H | N$_3$ | B | OH | H |
| I-30 | 4-Cl-Ph | CH$_2$CHMe$_2$ | H | S | Et | H | N$_3$ | A | OH | H |
| I-31 | 3,4-di-Cl-Ph | CH$_2$CHMe$_2$ | H | S | Et | H | N$_3$ | A | OH | H |
| I-32 | Ph | H | Me | R | CH$_2$Ph | H | N$_3$ | B | OH | H |
| I-33 | Ph | H | H | — | CH$_2$Ph | H | N$_3$ | A | OH | H |
| I-34 | Ph | Me | H | S | Et | H | N$_3$ | B | OH | H |
| I-35 | Ph | Me | H | S | i-Pr | H | N$_3$ | B | OH | H |
| I-36 | Ph | CHMe$_2$ | H | S | CH$_2$Ph | H | N$_3$ | B | OH | H |
| I-37 | 4-Me-Ph | CH$_2$CHMe$_2$ | H | S | Et | H | N$_3$ | A | OH | H |
| I-38 | 4-MeO-Ph | CH$_2$CHMe$_2$ | H | S | Et | H | N$_3$ | A | OH | H |
| I-39 | Ph | Me | H | S | CH$_2$Ph | H | CH═CHCl | A | OH | H |
| I-40 | Ph | H | Me | R | CH$_2$Ph | H | N$_3$ | A | OH | H |

TABLE I-continued

| | | | | | | | | | | |
|---|---|---|---|---|---|---|---|---|---|---|
| I-41 | Ph | H | Me | R | CH$_2$Ph | H | C≡CH | A | OH | H |
| I-42 | Ph | Me | H | S | tert-Bu | H | C≡CH | A | OH | H |
| I-43 | Ph | H | Me | R | Et | H | N$_3$ | B | OH | H |
| I-44 | Et$_3$NH$^+$ | Me | H | S | Et$_3$NH$^+$ | H | N$_3$ | B | OH | H |
| I-45 | 4-Cl-Ph | Me | H | S | CH$_2$Ph | H | N$_3$ | A | OH | H |
| I-46 | Ph | CHMe$_2$ | H | S | CH$_2$Ph | H | N$_3$ | A | OH | H |
| I-47 | Ph | (CH$_2$)$_2$SMe | H | S | Et | H | N$_3$ | B | OH | H |
| I-48 | Ph | (CH$_2$)$_2$SMe | H | S | Et | H | N$_3$ | A | OH | H |
| I-49 | Ph | H | H | S | CH$_2$Ph | H | C≡CH | A | OH | H |
| I-50 | Ph | Me | H | S | tert-Bu | H | N$_3$ | A | OH | H |
| I-51 | 4-Cl-Ph | H | Me | R | CH$_2$Ph | H | N$_3$ | A | OH | H |
| I-52 | 3,4-di-Cl-Ph | H | Me | R | CH$_2$Ph | H | N$_3$ | A | OH | H |
| I-53 | Ph | H | Me | R | tert-Bu | H | N$_3$ | B | OH | H |
| I-54 | Ph | Me | H | S | Me | H | N$_3$ | A | OH | H |
| I-55 | Ph | Me | H | S | Me | H | N$_3$ | B | OH | H |
| I-56 | Ph | Me | H | S | CH$_2$Ph | H | C≡CH | A | OH | H |
| I-57 | Ph | CH$_2$CHMe$_2$ | H | S | i-Pr | H | N$_3$ | B | OH | H |
| I-58 | Ph | CH$_2$CHMe$_2$ | H | S | i-Pr | H | N$_3$ | A | OH | H |
| I-59 | Ph | CH$_2$Ph | H | S | H | H | N$_3$ | B | OH | H |
| I-60 | Ph | H | Me | R | i-Pr | H | N$_3$ | A | OH | H |
| I-61 | Ph | H | H | — | Et | Me | N$_3$ | A | OH | H |
| I-62 | Ph | H | Me | R | CH(Et)Me | H | N$_3$ | A | OH | H |
| I-63 | Ph | H | Me | R | C$_{12}$H$_{25}$ | H | N$_3$ | A | OH | H |
| I-64 | Ph | H | Me | R | C$_{12}$H$_{25}$ | H | N$_3$ | B | OH | H |
| I-65 | 4-MeO-Ph | Me | H | S | CH$_2$Ph | H | N$_3$ | A | OH | H |
| I-66 | 4-MeO-Ph | Me | H | S | CH$_2$Ph | H | N$_3$ | B | OH | H |
| I-67 | NH$_4^+$ | Me | Me | — | NH$_4^+$ | H | N$_3$ | A | OH | H |
| I-68 | NH$_4^+$ | H | Me | R | CH$_2$Ph | H | N$_3$ | B | OH | H |
| I-69 | NH$_4^+$ | Me | Me | — | NH$_4^+$ | H | N$_3$ | B | OH | H |
| I-70 | Ph | H | H | — | Et | Me | N$_3$ | B | OH | H |
| I-71 | NH$_4^+$ | CH$_2$Ph | H | S | Et | H | N$_3$ | A | OH | H |
| I-72 | NH$_4^+$ | CH$_2$Ph | H | S | NH$_4^+$ | H | N$_3$ | A | OH | H |
| I-73 | Ph | CH$_2$Ph | H | S | Et | H | N$_3$ | A | OH | H |
| I-74[2] | Ph | CH$_2$Ph | H | S | Et | H | N$_3$ | B | OH | H |
| I-75[3] | Ph | CH$_2$Ph | H | S | Et | H | N$_3$ | A | OH | H |
| I-76 | NH$_4^+$ | Me | H | S | NH$_4^+$ | H | N$_3$ | A | OH | H |
| I-77 | 4-Me-Ph | Me | H | S | Et | H | N$_3$ | A | OH | H |
| I-78 | Ph | (CH$_2$)$_2$CO$_2$Et | H | S | Et | H | N$_3$ | A | OH | H |
| I-79 | Ph | H | Me | R | n-Bu | H | N$_3$ | A | OH | H |
| I-80 | Ph | Me | H | S | n-Bu | H | N$_3$ | A | OH | H |
| I-81 | Ph | H | Me | R | n-Bu | H | N$_3$ | B | OH | H |
| I-82 | 4-Me-Ph | Me | H | S | n-Bu | H | N$_3$ | B | OH | H |
| I-83 | Ph | (CH$_2$)$_2$CO$_2$Et | H | S | Et | H | N$_3$ | B | OH | H |
| I-84 | NH$_4^+$ | CH$_2$Ph | H | S | Et | H | N$_3$ | B | OH | H |
| I-85 | NH$_4^+$ | CH$_2$Ph | H | S | NH$_4^+$ | H | N$_3$ | B | OH | H |
| I-86 | Br-2-naph[4] | Me | H | S | CH$_2$Ph | H | N$_3$ | A | OH | H |
| I-87 | 1-naph[5] | Me | H | S | CH$_2$Ph | H | N$_3$ | C | OH | H |
| I-88 | 1-naph | Me | H | S | CH$_2$Ph | H | N$_3$ | D | OH | H |
| I-89 | 1-naph | Me | H | S | CH$_2$CF$_3$ | H | N$_3$ | A | OH | H |
| I-90 | CF$_3$CH$_2$ | Me | H | S | CH$_2$Ph | H | N$_3$ | B | OH | H |
| I-91 | Pentanoic acid (2R,3R,4S,5R)-2-(4-amino-2-oxo-2H-pyrimidin-1-yl)-5-azido-5-[((S)-1-benzyloxycarbonyl-ethylamino)-phenoxy-phosphoryloxymethyl]-4-pentanoyloxy-tetrahydro-furan-3-yl ester | | | | | | | | | |

[1] Designates the stereochemistry of the alpha-amino carbon
[2] Trifluoroacetic acid salt
[3] Formic acid salt
[4] Br-2-napth = 6-bromo-naphth-2-yl
[5] 1-naph = naphtha-1-yl

TABLE II

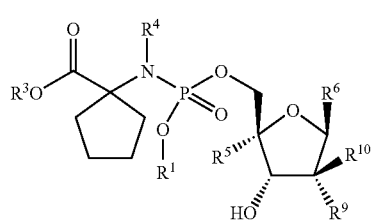

II

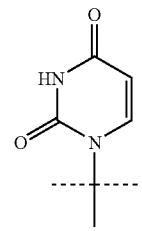

A

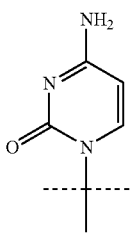

B

| No. | $R^1$ | $R^3$ | $R^5$ | $R^6$ | $R^9$ | $R^{10}$ |
|---|---|---|---|---|---|---|
| II-1 | Ph | Et | $N_3$ | B | HO | H |
| II-2 | Ph | i-Pr | $N_3$ | B | HO | H |
| II-3 | Ph | $CH_2Ph$ | $N_3$ | B | HO | H |
| II-4 | Ph | $CH_2Ph$ | $N_3$ | A | HO | H |
| II-5 | Ph | Et | $N_3$ | A | HO | H |
| II-6 | $Et_3NH^+$ | Et | $N_3$ | B | HO | H |
| II-7 | Ph | i-Pr | $N_3$ | A | HO | H |
| II-8 | H | i-Pr | $N_3$ | A | HO | H |

TABLES III AND IV

III

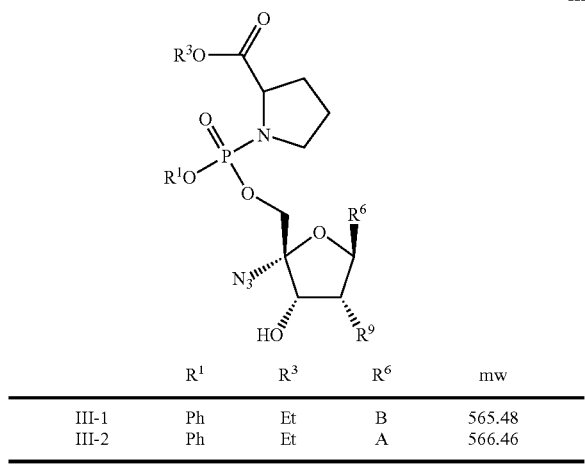

| | $R^1$ | $R^3$ | $R^6$ | mw |
|---|---|---|---|---|
| III-1 | Ph | Et | B | 565.48 |
| III-2 | Ph | Et | A | 566.46 |

A

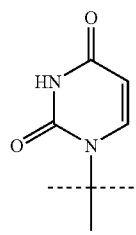

B

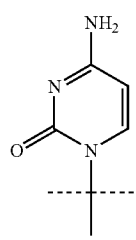

TABLES III AND IV-continued

IV

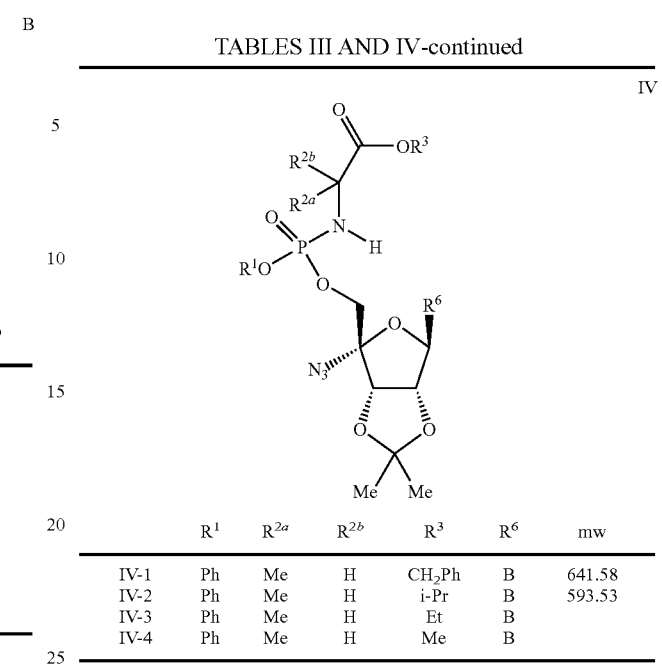

| | $R^1$ | $R^{2a}$ | $R^{2b}$ | $R^3$ | $R^6$ | mw |
|---|---|---|---|---|---|---|
| IV-1 | Ph | Me | H | $CH_2Ph$ | B | 641.58 |
| IV-2 | Ph | Me | H | i-Pr | B | 593.53 |
| IV-3 | Ph | Me | H | Et | B | |
| IV-4 | Ph | Me | H | Me | B | |

Dosage and Administration

The compounds of the present invention may be formulated in a wide variety of oral administration dosage forms and carriers. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-hlorobenzenesulfonic acid, 2-naphthalenesulfonic acid, 4-toluenesulfonic acid, camphorsulfonic acid, 4-ethylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HCV infection, as used herein, also includes treatment or prophylaxis of a disease or a condition associated with or mediated by HCV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

General Methodology

TLC was carried out on precoated, aluminium backed plates (60 F-54, 0.2 mm thickness; supplied by E. Merck A G, Darmstad, Germany) developed by ascending method. After solvent evaporation, compounds were detected by irradiation with an UV lamp at 254 nm or 366 nm observation of quenching of the fluorescence. Chromatography columns were slurry packed in the appropriate eluent under pressure, with silica gel, 60A, 40-60 µm, Phase Sep, UK). Samples were applied as a concentrated solution in the same eluent, or pre-adsorbed on silica gel. $^1$H and $^{13}$C NMR spectra were recorded on a Bruker Advance DPX300 spectrometer (300 MHz and 75 MHz respectively) and autocalibrated to the deuterated solvent reference peak. All $^{13}$C NMR were proton decoupled. The following abbreviations are used in the assignment of NMR signals: s (singlet), d (doublet), t (triplet), qu (quartet), q (quintet), m (multiplet), bs (broad signal), dd (double doublet), dt (double triplet). Low-resolution mass spectra were run on a VG Platform II Fisons instrument (atmospheric pressure ionization, electrospray mass spectrometry) in either negative or positive mode.

The solvents used were anhydrous and used as purchased from Aldrich. All glassware was oven dried at 130° C. for several hours and allowed to cool under a stream of dry nitrogen.

EXAMPLE 1

(A) General Procedure for Preparing amino acid benzyl ester hydrochloride Salts

The amino acid (1.0 mol eq.) was suspended in toluene (10 mol eq.), p-TsOH (1.1 mol eq.) and anhydrous benzyl alcohol (4.0 mol eq.) was added and the resulting mixture was heated at reflux with Dean-Stark trap for 6-24 h (the reaction was quenched when the appropriate amount of water was collected from the Dean-Stark trap). On cooling to RT, Et$_2$O was added and the mixture was left in ice bath for 1 h then filtered and washed with Et$_2$O. The solid was dissolved in DCM and washed with 10% K$_2$CO$_3$ and water. The organic layer was dried (MgSO$_4$), filtered and the solvent removed in vacuo. The resulting product was dissolved in acetone and the mixture was neutralized with 1 M HCl. The solvent was then evaporated and the solid was triturated with Et$_2$O to afford the amino benzyl ester hydrochloride salt as a white solid.

(B) General Procedure for Preparing amino acid ester hydrochloric Salts

Thionyl chloride (2.0 mol. equivalents) was added dropwise to a stirred solution of the appropriate anhydrous alcohol (10.0 mol equivalents) under argon atmosphere and cooled to 0° C. The mixture was stirred at 0° C. for 1 h and then slowly allowed to warm to RT. The appropriate amino acid (1.0 mol. equivalents) was added and the mixture was heated at reflux overnight. The solvent was removed under reduced pressure (last traces of solvent were removed by co-evaporation with increasingly more volatile solvents). The crude product was then triturated with $Et_2O$ to afford the pure amino acid ester hydrochloric salt.

(C) General Procedure for Preparing amino acid ester sulfonate Salts

A mixture of the appropriate amino acid (1.0 mol. equivalent), the appropriate alcohol (15 mol. equivalent) and para-toluene sulfonic acid (p-TSA) monohydrate (1.1 mol equivalent) in toluene was heated at reflux overnight, using Dean-Stark apparatus. The solvent was removed under reduced pressure (last traces of solvent removed by co-evaporation with increasingly volatile solvents) to give the crude product as the solid p-toluene sulfonate salt.

EXAMPLE 2

General Procedure for Preparation of phosphorodichloridates

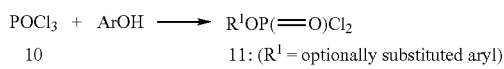

$POCl_3$ + ArOH → $R^1OP(=O)Cl_2$ 10                          11: ($R^1$ = optionally substituted aryl)

To a stirred solution of phosphorus oxychloride (1.0 mol. eq.) and the appropriate phenol (1.0 mol. eq.) in anhydrous ether cooled to −78° C. was added dropwise anhydrous TEA (1.0 mol. eq.), and the resultant stirred mixture allowed to reach RT overnight. The triethylamine salt was quickly removed with suction filtration and the filtrate concentrated in vacuo to dryness to afford 11 as an oil which was used without further purification.

EXAMPLE 3

General Procedure for Preparation of phosphorochloridates

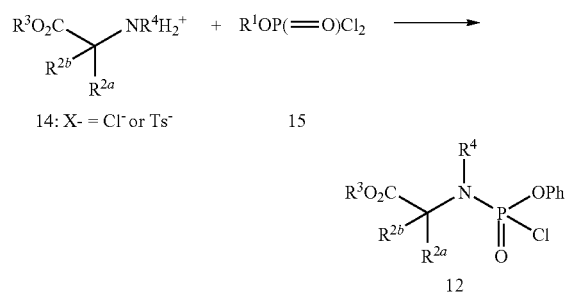

Aryloxy-phosphodichloridate (15, 1.0 mol. equivalents) and the appropriate amino ester (14, 1.0 mol. equivalents) were suspended in anhydrous DCM (123 mol. equivalent). The reaction was cooled to −78° C. and anhydrous TEA was added dropwise and after 30 to 60 min the reaction was allowed to warm to RT and stirred overnight. The formation of the corresponding phosphochloride was monitored by $^{31}P$ NMR. The solvent was removed in vacuo and the crude residue was purified by filtration through silica eluting with EtOAc/hexane (7:3). The fractions containing the product were then collected and the solvent evaporated under reduced pressure to afford the phosphorochloridates 12. All phosphorochloridates were used as solutions in dry THF in subsequent reactions.

EXAMPLE 4

General Procedures for phosphoramidate derivatives

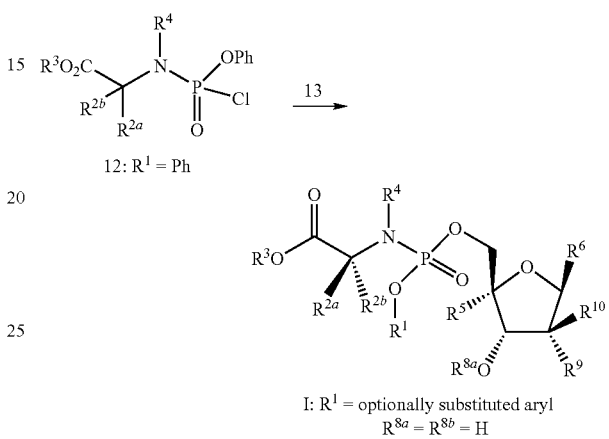

The nucleoside 13 (wherein $R^5$, $R^6$, $R^{8a}$, $R^9$ and $R^{10}$ are as defined in claim 1) was dried in under reduced pressure at 40° C. for 5 h before being used as in the reaction. t-BuMgCl (2.5 mol equivalents) was added to a solution/suspension of the nucleoside analogue (1.0 mol equivalents) in anhydrous THF and the reaction mixture was stirred for 15 min. A solution of the appropriate phosphorochloridate (12, 2.5 mol equivalents) in dry THF (0.5 M) was added dropwise and the reaction mixture was stirred overnight. A saturated solution of $NH_4Cl$ was added and the mixture was stirred for 30 min. The solvent was removed in vacuo and the crude was purified by column chromatography and/or preparative thin layer chromatography.

EXAMPLE 5

General Procedure for 5'-monophosphate Species

Phosphorus oxychloride (1.5 mol. equivalent) was added to a solution of the appropriate modified nucleoside (13, 1 mol equivalent) and DMAP (1.5 mol equivalent) in $(EtO)_3PO$ (0.5 mL) at 0° C. The solution was stirred for 30 min to 5 h, then $NH_4HCO_3$ was added to the solution. Triethyl phosphate was removed by extraction with $Et_2O$ and water. The aqueous layer was concentrated in vacuo under reduced pressure to afford a yellow solid.

EXAMPLE 6

General Procedure monobasic Salts

The appropriate amino acid ester (7 mol equivalent) was added to a solution of the nucleoside 5'-monophosphate species (1 mol equivalent) and DCC (5 mol. equivalent) in tert-BuOH (5 mL) and $H_2O$ (2 mL) and the resulting mixture was stirred and heated at reflux for 4 h. The solvent was removed in vacuo to afford the desired salt which was purified as described.

EXAMPLE 7

General Procedure for Deprotection of 2',3'-isopropylidene derivatives

The appropriate 4'-azido-2',3'-isopropylidenecytidine phosphoramidate was dissolved in a 60:40 HOAc/water mixture, and the solution heated to 90° C. overnight. TLC analysis showed the presence of three spots, in order of increasing polarity: unconsumed starting material, product and baseline material. The solvents were removed in vacuo and the resultant crude mixture purified by preparative TLC (9:1 DCM/MeOH) to yield a white solid. The same procedure can be used with other ketals used as 1,2-diol protecting groups.

EXAMPLE 8

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-3-phenyl-propionic acid ethyl ester (I-2)

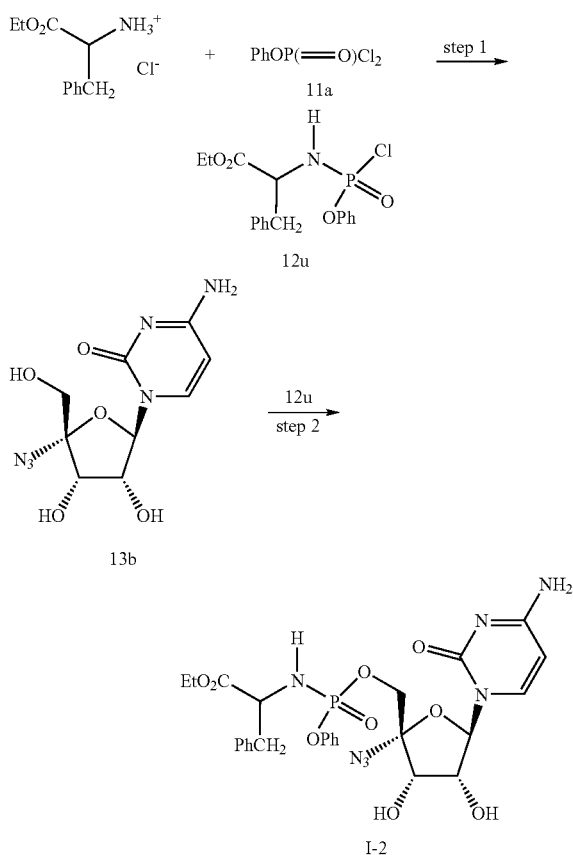

step 1—Phenyl-(ethoxy-L-phenylalaninyl)-phosphorochloridate (12u) was synthesised according to Example 3, using ethyl L-phenylalaninate hydrochloride salt (14u, X=Cl⁻; 1.5 g, 6.53 mmol), phenyl dichlorophosphate (11a, 0.98 mL, 6.53 mmol), and TEA (1.8 mL, 13.06 mmol) in DCM (40 mL) to yield 1.70 g (72%) of 12u.

$^{31}$P-NMR (CDCl$_3$, 121 MHz): δ 9.21, 9.25 $^1$H-NMR (CDCl$_3$; 300 MHz): δ 7.44-7.16 (5H, m, OPh), 4.50-4. (1H, m, CH-Phe), 4.27-4.18 (3H, m, OC$\underline{H}_2$CH$_3$ and NH), 3.22-3.16 (CH$_2$-Phe) 1.33-1.26 (3H, m, OCH$_2$C$\underline{H}_3$); $^{13}$C-NMR (CDCl$_3$; 75 MHz): δ 14.7, 14.9 ($\underline{C}$H$_3$CH$_2$O), 40.5, 40.6, 40.7, 40.8 (CH$_2$-Phe), 56.2, 56,7 (CH-Phe) 62.5, 62.5 (O$\underline{C}$H$_2$CH$_3$), 121.1, 121.2, 121.3, 126.6, 127.9, 128.0, 129.2, 130.3, 130.5, 130.6, 135.7, 135.8 (C-Ph), 150.3, 150.4, 150.5 ('ipso', O-Ph), 171.7, 171.8, 171.9, 172.0 (C=0).

step 2—The title compound was prepared as described in Example 4. 4'-azido-cytidine monohydrate (13b, 200 mg, 0.66 mmol) was dissolved in anhydrous pyridine (3 mL) and the solvent was evaporated. This procedure was repeated three times before using the nucleoside analogue as starting material. A solution of the nucleoside 13b and anhydrous THF (15 mL) was treated with tert-BuMgCl (1.65 mL of a 1M solution in THF, 1.65 mmol) and phenyl-(ethoxy-L-phenylalaninyl)-phosphorochloridate (12u; 364 mg dissolved in 1 mL of THF; 2.46 mmol). The reaction was monitored by TLC and developed with CHCl$_3$:MeOH (8:2). The crude was purified by a gradient column chromatography and eluted with a CHCl$_3$:MeOH gradient (10 to 20% MeOH). The recovered product was chromatographed twice using the same conditions and further purified by preparative TLC developed with CHCl$_3$:MeOH (85:15) to afford pure I-2 as a white solid (20.0 mg, yield 5%).

$^{31}$P-NMR (CD$_3$OD, 121 MHz): δ 4.24, 4.52; $^1$H-NMR (CD$_3$OD, 300 MHz): δ 7.66, 7.46 (1H, d, J=7.5 Hz H-6,), 7.45-7.14 (10H, m, Ph), 6.27-6.20 (1H, m, H-1'), 5.98, 5.91 (1H, d, J=7.5 Hz, H-5), 4.33-3.74 (7H, m, H-1', H-3', H-5', CH-Phe, OCH$_2$CH$_3$), 3.22-2.93 (2H, m, CH$_2$-Phe), 1.29-1.14 (3H, m, OCH$_2$C$\underline{H}_3$); $^{-C\text{-}NMR\ (CD}_3$OD; 75 MHz): δ 14.8, 14.8 (OCH$_2\underline{C}$H$_3$), 41.1, 41.3, 41.4 (CH$_2$-Phe), 58.2, 58.4 (CH-Phe), 62.8, 62.9 (O$\underline{C}$H$_2$CH$_3$), 68.6, 68.7, 68.8 (C-5'), 73.7, 74.7, 74.9 (C-2', C-3'), 93.4, 93.8 (C-1'), 9.72 (C-5), 98.7, 98.9, 99.0 (C-4'), 121.4, 121.5, 121.7, 121.8, 126.6, 126.7, 128.4, 128.4, 130.0, 130.9, 131.2, 138.5 (C-Ph), 143.0, 143.3 (C-6), 152.2, 152.3 ('C-ipso' O-Ph), 158.5 (C-2), 168.0 (C-4), 174.2, 174.3, 17.4 (C=O). MS (ES$^+$) m/e 638.3 (MNa$^+$). Accurate mass: C$_{26}$H$_{30}$N$_7$O$_9$NaP requires 638.1740; found 638.1734.

EXAMPLE 9

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-3-phenyl-propionic acid isopropyl ester (I-9)

step 1—phenylalanine iso-propyl ester phosphororchloridate (12v)

The title compound was prepared as described in Example 3 utilizing phenyl dichlorophosphate (0.36 mL, 2.4 mmol), L-phenylalanine iso-propyl ester hydrochloride (14v, 1.003 g, 2.4 mmol), dry TEA (0.67 mL, 4.8 mmol) and dry DCM (20 mL). The phosphorochloridate 12v was obtained as a yellow oil (1.50 g, yield 91%).

$^{31}$P NMR (CDCl$_3$): δ9.48, 9.69.

step 2—4'-Azido-5'-[phenyl-(iso-propoxy-L-phenylalaninyl)]-phosphate uridine (I-9)

The title compound was prepared as described in Example 4 utilizing 4'-azido-uridine (200 mg, 0.7 mmol), tert-BuMgCl (1.4 mL 1M solution in THF, 1.4 mmol), 12v (0.53 g, 1.4 mmol) and dry THF (10 mL). The crude was purified by column chromatography eluting with CHCl$_3$/MeOH (90:10) followed preparative TLC chromatography developed with CHCl$_3$/MeOH (85:15) which afforded I-9 as a colorless oil that dried to form a white foam (0.012 g, yield 3%).

$^{31}$P NMR (CD$_4$OD) δ4.22, 4.25; $^1$H NMR (CD$_4$OD): δ6.7-7.1 (10H, m, Ar—H), 6.28 (1H, dd, H1'), 5.68 (1H, dd, H5), 4.23 (1H, m, CO$_2$C$\underline{\text{H}}$(CH$_3$)$_2$), 3.91 (1H, t, NH—C$\underline{\text{H}}$—), 3.5-3.7 (2H, m, H2', H3'), 2.99 (C$\underline{\text{H}}_2$-Ph), 1.26-1.30 (6H, m, CO$_2$CH(C$\underline{\text{H}}_3$)$_2$).

EXAMPLE 10

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-3-phenyl-propionic acid isopropyl ester (I-18)

The title compound was prepared as described in Example 4 utilizing 4'-azido-cytidine (13b, 200 mg, 0.66 mmol), tert-BuMgCl (1.3 mL 1M solution in THF, 1.3 mmol), 12v (0.505 g, 1.3 mmol) and dry THF (10 mL). The crude was purified by two column chromatographies eluting with CHCl$_3$/MeOH (90:10) followed three preparative TLC chromatographies developed with CHCl$_3$/MeOH (85:15) which afforded I-18 as a white solid (0.04 g, yield 35%).

$^{31}$P NMR (CD$_4$OD): δ4.27, 4.54; $^1$H NMR (CD$_4$OD): δ$_H$7.91 (1H, s, H6), 7.0-7.37 (16H, m, Ar—H) 6.15 (1H, dd, H1'), 5.87 (1H, dd, H5), 4.19-4.31 (2H, m, H2', H3'), 3.86 (1H, t, NH—C$\underline{\text{H}}$), 3.4-3.7 (2H, m, H2', H3'), 3.04 (2H, C$\underline{\text{H}}_2$Ph), 1.18-1.27 (6H, m, CO$_2$CH(C$\underline{\text{H}}_3$)$_2$).

EXAMPLE 11

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-3-phenyl-propionic acid isopropyl ester (I-7)

The title compound was synthesized by the procedure in Example 4 utilizing 4'-azido-cytidine monohydrate (13a, 200.0 mg, 0.66 mmol) dissolved in anhydrous THF (10 mL), tert-BuMgCl (1.65 mL of solution 1 M in THF, 1.65 mmol) and 12w (1.65 mL of a 1.0 M solution in THF, 1.65 mmol). The crude was purified by two column chromatographies eluting a DCM/MeOH gradient (90: 10 to 80:20). The product was further purified by a preparative TLC developed with DCM/MeOH (90:10) to afford I-7 as a white solid (18 mg, yield 4%).

$^{31}$P NMR (121.5 MHz, d$_4$-MeOH): δ4.45, 4.19; $^1$H NMR (300 MHz, d$_4$-MeOH): δ7.61-7.54 (1H, m, H-6), 7.06-7.03 (13H, m, Ph-CH) 7.06-7.03 (2H, m, Ph-CH), 6.19-6.12 (1H, m, H-1'), 5.91-5.81 (1H, m, H-5), 5.14-5.09 (2H, m, Bn-CH$_2$), 4.65 (1H, br, H-2') 4.30-4.15 (3H, m, H-3' and H-5'), 3.89-3.80 (1H, m, Phe-CH), 3.16-3.06 (1H, m, Bn-CH$_2$), 3.02-2.84 (1H, m, Bn-CH$_2$),

EXAMPLE 12

2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-2-methyl-propionic acid benzyl ester (I-3)

step 1—Benzyl 2-amino-2-methylpropanoate hydrochloride salt (14p).

The title compound was prepared as described in Example 1 utilizing 2-amino-isobutyric acid (10.0 g, 0.097 mmol),p-TsOH (20.3 g, 0.107 mmol), benzyl alcohol (40.0 mL, 0.388 mmol) and toluene (200 mL). The benzyl ester (14p) was isolated as a white solid (13.0 g, yield 59%).

$^1$H-NMR (CDCl$_3$; 300 MHz): δ 9.04 (3H, bs, NH$_3$Cl), 7.42-7.38 (5H, m, Ph), 5.27 (2H, s, C$\underline{\text{H}}_2$Ph), 1.76 (6$\underline{\text{H}}$, s, [CH$_3$]$_2$C); $^{13}$C-NMR (CDCl$_3$; 75 MHz): δ 24.3 ([$\underline{\text{C}}$H$_3$]$_2$C), 58.0 ($\underline{\text{C}}$[CH$_3$]$_2$), 68.5 (CH$_2$Ph), 128.6, 129.0, 129.1 (C-Ph), 135.2 ('ipso', C-Ph), 171.65 (C═O).

step 2—Phenyl-(benzyloxy-2-amino-2-methylpropanoate) phosphorochloridate

The title compound was synthesized according to Example 3, using 2-aminoisobutyrate benzyl ester hydrochloride (14p, 2.00 g, 8.7 mmol), phenyl dichlorophosphate (1.3 mL, 8.7 mmol) and TEA (2.4 mL, 17.4 mmol) in DCM (50 mL) to afford 2.64 g (82%) of (12p) as an oil.

$^{31}$P-NMR (CDCl$_3$, 121 MHz): δ 6.76 (s); $^1$H-NMR (CDCl$_3$; 300 MHz): δ 7.48-7.27 (10H, m, Ph), 5.28 (2H, s, CH$_2$Ph), 4.79, 4.75 (1H, bs, NH), 1.78, 1.75 (6H, s, [CH$_3$]C); $^{13}$C-NMR (CDCl$_3$; 75 MHz): δ 26.9, 26.9, 27.3, 27.3 ([$\underline{\text{C}}$H$_3$]C), 58.9, 58.9 ($\underline{\text{C}}$[CH$_3$]$_2$), 68.4 (CH$_2$Ph), 121.0, 121.0, 126.3, 128.6, 129.0, 129.1, 130.3, 135.5 (C-Ph), 150.2, 150.3 ('ipso', OPh), 175.0, 175.1 (C═O).

step 3—4'-azido-5'-[phenyl-(benzyloxy-α,α-dimethylglycinyl)]-phosphate cytidine (I-3)

4'-azido-cytidine monohydrate (13b, 300 mg, 1.00 mmol) was dissolved in anhydrous pyridine (4 mL) and the solvent was evaporated. This procedure was repeated for three times. The nucleoside 13a was dissolved in a mixture of anhydrous THF (10 mL) and anhydrous pyridine (4 mL). tert-BuMgCl (2.0 mL of solution 1M in THF, 2.0 mmol) was added at 0° C. followed by phenyl-(benzyloxy-α,α-dimethylglycinyl)-phosphorochloridate (12p; 4 mL of a 0.5 M solution in THF, 2.00 mmol). The reaction was monitored by TLC (CHCl$_3$/MeOH 8:2). The crude was purified by column chromatography eluting with a CHCl$_3$:MeOH gradient (15 to 20% MeOH). The recovered product rechromatographed utilizing the same conditions and subsequently purified by preparative TLC and developed with CHCl$_3$/MeOH (85:15) to afford I-3 as a white solid (13.4 mg, yield 2%).

$^{31}$P-NMR (CD$_3$OD, 121 MHz): δ 3.04, 3.07; $^1$H-NMR (CD$_3$OD, 300 MHz): δ 7.64, 7.61 (1H, d, J=7.5 Hz H-6,), 7.36-7.16 (10H, m, Ph), 6.15-6.14 (1H, m, H-1'), 5.84, 5.83 (1H, d, J=7.5 Hz, H-5), 5.16-5.14 (2H, m, CH$_2$-Ph), 4.34-4.13 (4H, m, H-2', H-3', H-5'), 1.51-1.30 (6H, m, [CH$_3$]C); $^{13}$C-NMR (CD$_3$OD; 75 MHz): δ 27.9, 28.1, 28.2, 28.3 ([$\underline{\text{C}}$H$_3$]C), 58.6 ([CH$_3$]$\underline{\text{C}}$), 65.6, 68.7, 68.9, 69.1, 69.2 (C-5', $\underline{\text{C}}$H$_2$-Ph), 73.7, 73.8, 74.7, 74.9 (C-2', C-3'), 93.9, 94.1 (C-1'), 97.2 (C-5), 99.0, 99.1, 99.0 (C-4'), 121.8, 121.9, 122.0, 126.7, 128.4, 129.7, 130.0, 131.2, 137.7 (C-Ph), 143.3, 143.5 (C-6), 152.4, 152.5 ('C-ipso' O-Ph), 158.6 (C-2), 168.0 (C-4), 176.8, 176.8 (C═O). MS (ES$^+$) m/e 638.3 (MNa$^+$). Accurate mass: C$_{26}$H$_{30}$N$_7$O$_9$NaP requires 638.1740 found 638.1733.

EXAMPLE 13

2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-2-methyl-propionic acid benzyl ester (I-4)

The title compound was prepared according to Example 4 utilizing 4'-azido-uridine (13a; 290 mg, 1.01 mmol) dissolved in anhydrous THF (13 mL), tert-BuMgCl (1.5 mL of solution 1 M in THF, 1.5 mmol) and phenyl-(benzyloxy-α,α-dimethylglycinyl)-phosphorochloridate (12p, 3.0 mL of a 0.5 M solution in THF, 1.5 mmol). The reaction was monitored by TLC developed with CHCl$_3$:MeOH (9:1). After one additional hour, tert-buMgCl (0.5 mL of solution 1M in THF, 0.5 mmol) and 12p (1.0 mL of a 0.5 M solution in THF, 0.5 mmol) were added and the reaction was stirred overnight. The crude was purified by column chromatography and eluting with CHCl$_3$:MeOH (9:1). The recovered product was further purified by preparative TLC developed with CHCl$_3$:MeOH (9:1) to afford I-4 as a white solid (132.3 mg, yield 21%).

$^{31}$P-NMR (CD$_3$OD, 121 MHz): δ 3.11, 3.14; $^1$H-NMR (CD$_3$OD, 300 MHz): δ 7.66, 7.62 (1H, d, J=8.1 Hz H-6,), 7.41-7.19 (10H, m, Ph), 6.17-6.16 (1H, m, H-1'), 5.68, 5.66 (1H, d, J=8.1, H-5), 5.18-5.17 (2H, m, CH$_2$-Ph), 4.43-4.15 (4H, m, H-2', H-3', H-5'), 1.53-1.52 (6H, m, [CH$_3$]C); $^{13}$C-NMR (CD$_3$OD; 75 MHz): δ 27.9, 28.1, 28.2, 28.3 ([CH$_3$]C), 58.7 ([CH$_3$]C), 68.7, 69.1, 68.9, 69.2 (C-5', CH$_2$-Ph), 74.2 (C-2', C-3'), 92.5, 92.7 (C-1'), 99.0, 99.1, 99.2 (C-4'), 104.0 (C-5), 121.8, 121.9, 121.9, 122.0, 126.7, 129.7, 129.7, 130.0, 130.6, 131.2, 137.7 (C-Ph), 143.0, 143.1 (C-6), 152.3, 152.4, 152.6 (C-2, 'C-ipso' O-Ph), 166.0 (C-4), 176.8, 176.9 (C=O). MS (ES$^+$) m/e 639.3 (MNa$^+$). Accurate mass: C$_{26}$H$_{29}$N$_6$O$_{10}$NaP requires 639.1580 found 639.1581

EXAMPLE 14

2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-2-methyl-propionic acid ethyl ester (I-10) and 2-{[(2R,3S,5R)-5-(4-Amino-2-oxo-2H-pyrimidin-1-yl)-2-azido-3,4-dihydroxy-tetrahydro-furan-2-ylmethoxy]-hydroxy-phosphorylamino}-2-methyl-propionic acid; compound with ammonia (I-69)

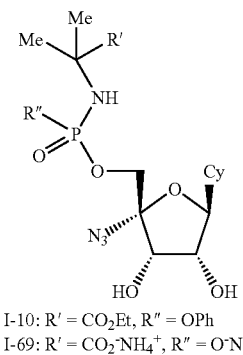

I-10: R' = CO$_2$Et, R'' = OPh
I-69: R' = CO$_2^-$NH$_4^+$, R'' = O$^-$NH$_4^+$ step 1—Ethyl 2-amino-2-methylpropanoate hydrochloride salt The title compound was prepared according to Example 1 (A) utilizing 2-amino-isobutyric acid (8.0 g, 77.6 mmol), thionyl chloride (11.3 mL, 155.2 mmol) and anhydrous EtOH (45.5 mL, 776.0 mmol). The product 14n was isolated as a white solid (9.12 g, yield 70%).

$^1$H-NMR (CDCl$_3$; 300 MHz): δ 8.93 (3H, bs, NH$_3$Cl), 4.25 (2H, q, J=7.1 Hz, OCH$_2$CH$_3$), 1.72 (6H, s, [CH$_3$]$_2$C), 1.30 (3H, t, J=7.1 Hz, OCH$_2$CH$_3$); $^{13}$C-NMR (CDCl$_3$; 75 MHz): δ 14.4 (OCH$_2$CH$_3$), 24.3 ([CH$_3$]$_2$C), 57.8 (C[CH$_3$]$_2$), 63.0 (OCH$_2$CH$_3$), 171.5 (C=O).

step 2—phenyl-(ethyl-2-amino-2-methylpropanoate)phosphorochloridate

The title compound was synthesized by the procedure in Example 3 utilizing 14n (2.50 g, 10.9 mmol), phenyl dichlorophosphate (11a, 1.6 mL, 10.9 mmol) and TEA (3.0 mL, 21.8 mmol) in DCM (60 mL) to afford 3.18 g (80%) of pure 12n as an oil.

$^{31}$P-NMR (CDCl$_3$, 121 MHz): δ 6.84 (s); $^1$H-NMR (CDCl$_3$; 300 MHz): δ 7.43-7.23 (5H, m, Ph), 4.78, 4.75 (1H, bs, NH), 4.27 (2H, q, J=7.1 Hz, OCH$_2$CH$_3$), 1.73, 1.70 (6H, s, [CH$_3$]$_2$C), 1.33 (3H, t, J=7.1 Hz, OCH$_2$CH$_3$); $^{13}$C-NMR (CDCl$_3$; 75 MHz): δ 14.5, 14.6 (CH$_3$CH$_2$O), 26.9, 27.0, 27.3, 27.3 ([CH$_3$]$_2$C), 58.7, 58.8 (C[CH$_3$]$_2$), 62.8 (OCH$_2$CH$_3$), 121.0, 121.1, 126.3, 126.3, 130.3 (Ph), 150.2, 150.4 ('ipso', OPh), 175.1, 175.3 (C=O).

step 3—azido-5'-[phenyl-(ethyloxy-α,α-dimethylglycinyl)]-phosphate cytidine

The title compound was synthesized by the procedure in Example 4 utilizing 4'-azido-cytidine monohydrate (13b, 1.00 g, 3.31 mmol) dissolved in a mixture of anhydrous THF (10 mL) and anhydrous pyridine (4 mL), tert-BuMgCl (8.3 mL of solution 1M in THF, 8.3 mmol) and 12n (16.6 mL of a 0.5M solution in THF, 8.3 mmol). The reaction was monitored by TLC developed with CHCl$_3$:MeOH (8:2). The crude was purified by column chromatography eluting with a CHCl$_3$:MeOH gradient (15 to 20% MeOH). The recovered product rechromatographed using the same conditions and further purified by preparative TLC developed with CHCl$_3$:MeOH (85:15) to afford I-10 as a white solid (136.4 mg, yield 7%).

$^{31}$P-NMR (CD$_3$OD, 121 MHz): δ 3.12, 3.15; $^1$H-NMR (CD$_3$OD, 300 MHz): 6 7.68, 7.64 (1H, d, J=7.5 Hz H-6,), 7.41-7.17 (5H, m, Ph), 6.17-6.16 (1H, m, H-1'), 5.88, 5.86 (1H, d, J=7.5Hz, H-5), 4.40-4.12 (6H, m, H-2', H-3', H-5', OCH$_2$CH$_3$), 1.49-1.47 (6H, m, [CH$_3$]C), 1.26, 1.25 (3H, t, J=7.1 Hz, OCH$_2$CH$_3$); $^{13}$C-NMR (CD$_3$OD; 75 MHz): δ 14.8 (OCH$_2$CH$_3$), 27.9, 28.1, 28.2 ([CH$_3$]C), 58.6 ([CH$_3$]C), 63.0 OCH$_2$CH$_3$), 69.0 (C-5'), 73.8, 73.9, 74.8 (C-2', C-3'), 94.0, 94.2 (C-1'), 97.2 (C-5), 99.0, 99.1 (C-4'), 121.8, 121.9, 122.0, 126.7, 131.2 (C-Ph), 143.4, 143.6 (C-6), 152.4 ('C-ipso' O-Ph), 158.6 (C-2), 168.0 (C-4), 177.1, 177.1 (C=O). MS (ES$^+$) m/e 576.1 (MNa$^+$). Accurate mass: C$_{21}$H$_{28}$N$_7$O$_9$NaP requires 576.1584 found 576.1587.

The phosphoramidate I-10 (223.4 mg, 0.40 mmol) was dissolved in a mixture of TEA/H$_2$O (4/1) (6 mL) and the reaction mixture was stirred at RT for 7 days. The solvent was removed in vacuo and the crude product was purified by a flash chromatography and eluted with a i-PrOH/NH$_3$/H$_2$O gradient (9:0.3:0.7 to 8:0.7:1.3) to afford I-69 as a white solid (29.5 mg, yield 16%).

$^{31}$P-NMR (D$_2$O, 121 MHz): δ 6.14; $^1$H-NMR (D$_2$O, 300 MHz): δ 7.80 (1H, d, J=7.6Hz H-6), 6.12 (1H, d, J=3.5 Hz H-1'), 6.01 (1H, d, J=7.6 Hz, H-5), 4.39-4.31 (2H, m, H-2', H-3'), 4.00-3.72 (2H, m, H-5'), 1.30 (6H, s, [CH$_e$]C).

EXAMPLE 15

2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-2-methyl-propionic acid ethyl ester (I-6) and 2-{[(2R, 3S,4R,5R)-2-Azido-5-(2,4-dioxo-3,4-dihydro-2H-pyrimidin-1-yl)-3,4-dihydroxy-tetrahydro-furan-2-ylmethoxy]-hydroxy-phosphorylamino}-2-methyl-propionic acid; compound with ammonia (I-67)

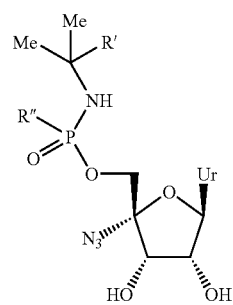

I-6: R' = CO$_2$Et, R'' = OPh
I-67: R' = CO$_2^-$NH$_4^+$, R'' = O$^-$NH$_4^+$

The title compound I-6 was prepared according to Example 4 utilizing 4'-azido-uridine (13a; 400 mg, 1.40 mmol) dissolved in anhydrous THF (15 mL), tert-BuMgCl (2.8 mL of solution 1 M in THF, 1.5 mmol) and 12n (5.6 mL of a 0.5 M solution in THF, 2.8 mmol). The reaction was monitored by TLC developed with CHCl$_3$:MeOH (9:1). The crude was purified by column chromatography and eluted with CHCl$_3$:MeOH (9:1). The recovered product was further purified by preparative TLC and developed with CHCl$_3$:MeOH (9:1) to afford I-6 as a white solid (203.5 mg, yield 26%).

$^{31}$P-NMR (CD$_3$OD, 121 MHz): δ 3.17, 3.20; $^1$H-NMR (CD$_3$OD, 300 MHz): δ 7.68, 7.64 (1H, d, J=8.1 Hz H-6,), 7.42-7.18 (5H, m, Ph), 6.16-6.14 (1H, m, H-1'), 5.69, 5.66 (1H, d, J=8.1Hz, H-5), 4.42-4.11 (6H, m, H-2', H-3', H-5', OCH$_2$CH$_3$), 1.49-1.48 (6H, m, [CH$_3$]C), 1.26, 1.24 (3H, t, J=7.1 Hz, OCH$_2$CH$_3$); $^{13}$C-NMR (CD$_3$OD; 75 MHz): δ 14.8 (OCH$_2$CH$_3$), 27.9, 28.1, 28.2 ([CH$_3$]C), 58.6 ([CH$_3$]C), 63.1 (OCH$_2$CH$_3$), 69.2 (C-5'), 74.1 (C-2', C-3'), 92.5 (C-1'), 99.2 (C-5), 103.9, 104.0 (C-4'), 121.9, 121.9, 122.0, 126.7, 131.2 (C-Ph), 143.0, 143.1 (C-6), 152.4, 152.6 (C-'ipso' O-Ph, C-2), 166.3 (C-4), 177.1 (C=O). MS(ES$^+$) m/e 577.0 (MNa$^+$). Accurate mass: C$_{21}$H$_{27}$N$_6$O$_{10}$NaP requires 577.1424 found 577.1431.

The bis-ammonium salt I-67 was prepared by hydrolysis of I-6 (154.5 mg, 0.28 mmol) in a mixture of TEA/H$_2$O (4/1, 7.5 mL) and the reaction mixture was stirred at RT for 4 days. The solvent was removed in vacuo and the crude was purified by a flash chromatography and eluted with iPrOH/NH$_3$/H$_2$O (8:0.7:1.3) to afford I-67 as a white solid (55.2 mg, yield 41%).

$^{31}$P-NMR (D$_2$O, 121 MHz): δ 6.07; $^1$H-NMR (D$_2$O, 300 MHz): δ 7.69 (1H, d, J=8.1Hz H-6), 5.93 (1H, d, J=3.9 Hz H-1'), 5.71 (1H, d, J=8.1 Hz, H-5), 4.28-4.22 (2H, m, H-2', H-3'), 3.82-3.68 (2H, m, H-5'), 1.15 (6H, s, [CH$_3$]C); $^{13}$C-NMR (D$_2$O; 75 MHz): δ 27.2 ([CH$_3$]C), 57.4 ([CH$_3$]C), 65.3 (C-5'), 7.14, 73.0 (C-2', C-3'), 90.6 (C-1'), 98.2, 98.4 (C-4'), 103.1 (C-4'), 142.2 (C-6), 151.0 (C-2), 166.4 (C-4), 184.7 (C=O). MS (ES$^-$) m/e 449.0 (M$^-$).

EXAMPLE 16

2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-2-methyl-propionic acid isopropyl ester (I-15)

step 1—iso-propyl 2-amino-2-methylpropanoate hydrochloride salt (14o)

The title compound was synthesised according to Example 1(A) utilizing 2-amino-isobutyric acid (8.0 g, 77.6 mmol), thionyl chloride (11.3 mL, 155.2 mmol) and anhydrous IPA (8.0 g, 77.6 mmol). The ester 14o was isolated as a white solid (9.12 g, yield 70%). The crude product was triturated with Et$_2$O, however, the solid retained traces of i-PrOH, the compound was dissolved in MeOH and the solvent removed under reduced pressure. The product was then triturated with Et$_2$O and recovered as a white solid (10.23 g, yield 72%).

$^1$H-NMR (CDCl$_3$; 300 MHz): δ 8.97 (3H, bs, NH$_3$Cl), 5.13 (1H, sept, J=6.2 Hz, CH-iPr), 1.75 (6H, s, [CH$_3$]$_2$C), 1.34 (6H, d, J=6.2 Hz, CH$_3$-iPr); $^{13}$C-NMR (CDCl$_3$; 75 MHz): δ 21.9, 24.2 ([DH$_3$]$_2$C, CH$_3$-iPr), 57.8 (C[CH$_3$]$_2$), 71.1 (CH-iPr), 171.0 (C=O).

step 2—Phenyl (ethyl-2-amino-2-methylpropanoate)phosphorochloridate (12o)

The title compound was synthesized by the procedure in Example 3 utilizing 14o (1.7 g, 9.36 mmol), phenyl dichlo-rophosphate (11a, 1.4 mL, 9.36 mmol) and TEA (2.60 mL, 18.72 mmol) in DCM (40 mL) to afford 1.58 g (53%) of 12o as an oil.

$^{31}$P-NMR (CDCl$_3$, 121 MHz): δ 6.94 (s); $^1$H-NMR (CDCl$_3$; 300 MHz): δ 7.45-7.23 (5H, m, Ph), 5.13 (1H, sept, J=6.2 Hz, CH-iPr), 4.83, 4.79 (1H, bs, NH), 1.74, 1.71 (6H, s, [CH$_3$]$_2$C), 1.34, 1.33 (6H, d, J=6.2 Hz, CH$_3$-iPr); $^{13}$C-NMR (CDCl$_3$; 75 MHz): δ 22.0 (CH$_3$-iPr), 26.9, 27.3 ([CH$_3$]$_2$C), 58.7, 58.8 (C[CH$_3$]$_2$), 70.5 (CH-iPr), 115.8, 120.6, 121.0, 121, 126.3, 127.0, 129.9, 130.3, 130.3, 130.5 (C-Ph), 150.2, 150.3 ('ipso', OPh), 174.6, 174.8 (C=O).

step 3—4'-azido-5'-[phenyl-(iso-propyloxy-α,α-dimethylglycinyl)]-phosphate cytidine (I-15)

The title compound was synthesized by the procedure in Example 4 utilizing 4'-azido-cytidine monohydrate (13b, 350.0 mg, 1.16 mmol) dissolved in anhydrous THF (15 mL), tert-BuMgCl (2.9 mL of solution 1M in THF, 2.9 mmol) and 12o (5.8 mL of a 0.5M solution in THF, 2.9 mmol). The reaction was monitored by TLC (8:2 CHCl$_3$:MeOH). The crude was purified by column chromatography eluting with a CHCl$_3$:MeOH gradient (15 to 20% MeOH). The recovered product rechromatographed with same conditions and further purified by preparative TLC developed with CHCl$_3$:MeOH (85:15) to afford I-15 as a white solid (89.24 mg, yield 13%).

$^{31}$P-NMR (CD$_3$OD, 121 MHz): δ 3.11, 3.16; $^1$H-NMR (CD$_3$OD, 300 MHz): δ 7.67, 7.64 (1H, d, J=7.5 Hz H-6,), 7.41-7.17 (5H, m, Ph), 6.17-6.16 (1H, m, H-1'), 5.88, 5.85 (1H, d, J=7.5 Hz, H-5) 5.51-4.94 (1H, m, H-iPr), 4.41-4.20 (4H, m, H-2', H-3', H-5'), 1.48-1.47 (6H, s, [CH$_3$]C), 1.25, 1.24 (6H, d, J=6.2 Hz, CH$_3$-iPr); $^{13}$C-NMR (CD$_3$OD; 75 MHz): δ 22.3 (CH$_3$-iPr), 27.8, 27.9, 28.1, 28.2 ([CH$_3$]C), 58.6 ([CH$_3$]C), 69.1 (C-5'), 70.8, 73.8, 73.8, 74.8 (C-2', C-3'CH-iPr), 94.0, 94.1 (C-1'), 97.3 (C-5), 99.1, 99.2 (C-4'), 121.9, 122.0, 122.0, 126.7, 131.2 (C-Ph), 143.4, 143.6 (C-6), 152.5 ('C-ipso' O-Ph), 158.6 (C-2), 168.0 (C-4), 176.6 (C=O).

EXAMPLE 17

2-{[(2R,3S,4R,5R)-2-Azido-5-(2,4-dioxo-3,4-dihydro-2H-pyrimidin-1-yl)-3,4dihydroxy-tetrahydro-furan-2-ylmethoxy]-phenoxy-phosphorylamino}-2-methyl-propionic acid isopropyl ester (I-12)

The title compound was prepared according to Example 4 utilizing 4'-azido-uridine (13a, 212.4 mg, 0.75 mmol) dissolved in anhydrous THF (13 mL) tert-BuMgCl (1.5 mL of solution 1 M in THF, 1.5 mmol) and 12o (3.0 mL of a 0.5 M solution in THF, 1.5 mmol). The reaction was monitored by TLC developed with CHCl$_3$:MeOH (9:1). The crude was purified by column chromatography and eluted with CHCl$_3$:MeOH (9:1). The recovered product was further purified by preparative TLC developed with CHCl$_3$:MeOH (9:1) to afford I-12 as a white solid (114.0 mg, yield 26%).

$^{31}$P-NMR (CD$_3$OD, 121 MHz): δ 3.18, 3.21; $^1$H-NMR (CD$_3$OD, 300 MHz): δ 7.67, 7.63 (1H, d, J=8.1 Hz H-6,), 7.41-7.19 (5H, m, Ph), 6.16-6.14 (1H, m, H-1'), 5.68, 5.65 (1H, d, J=8.1 Hz, H-5), 5.02-4.97 (1H, m, H-iPr), 4.40-4.20 (4H, m, H-2', H-3', H-5'), 1.48-1.47 (6H, s, [CH$_3$]C), 1.25, 1.24 (6H, d, J=6.2 Hz, CH$_3$-iPr); $^{13}$C-NMR (CD$_3$OD; 75 MHz): δ 22.3 (CH$_3$-iPr), 27.8, 27.9, 28.1, 28.2, 28.2 ([CH$_3$]C), 58.6 ([CH$_3$]C), 69.2 (C-5'), 70.8, 74.2 (C-2', C-3', CH-iPr), 92.5, 92.8 (C-1'), 99.1, 99.1, 99.2, 99.2 (C-5), 104.0, 104.1 (C-4'), 121.9, 121.9, 122.0, 126.7, 131.3 (C-Ph), 143.0, 143.2 (C-6), 152.4, 152.5, 152.6 ('C-ipso' O-Ph, C-2), 166.3 (C-4), 176.6, 176.6 (C=O). MS (ES$^+$) m/e 591.1 (MNa$^+$). Accurate mass: C$_{22}$H$_{29}$N$_{10}$NaP requires 591.1580 found 591.1589.

EXAMPLE 18

2-{[(2R,3S,4R,5R)-5-(4-Amino-2-oxo-2H-pyrimidin-1-yl)-2-azido-3,4-dihydroxy-tetrahydro-furan-2-ylmethoxy]-hydroxy-phosphorylamino}-2-methyl-propionate; triethylamine (I-22)

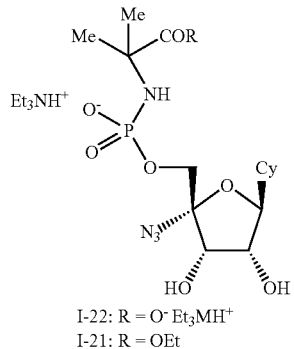

I-22: R = O⁻ Et₃NH⁺
I-21: R = OEt

4'-azido-5'-[phenyl-(ethyl-α,α-dimethylglycinyl)]-phosphate cytidine (I-10, 90.0 mg, 0.16 mmol) was dissolved in 5 mL of TEA/H₂O (4/1) and the reaction mixture was stirred at RT for 4 days. The solvent was removed in vacuo and the crude was purified by flash column chromatography and eluted with a CHCl₃:MeOH gradient (8:2 to 5:5) to afford I-22 as a white solid (21.0 mg, yield 15%).

³¹P-NMR (D₂O, 121 MHz): δ 6.11; ¹H-NMR (D₂O, 300 MHz): δ 7.76 (1H, d, J=7.5 Hz H-6), 6.05 (1H, d, J=3.5 Hz H-1'), 5.95 (1H, d, J=7.5 Hz, H-5), 4.32-4.24 (2H, m, H-2', H-3'), 4.32-4.24 (2H, m, H-5'), 3.05 (12H, q, J=7.3 Hz, CH₂-Et₃NH⁺), 1.23 (6H, s, [CH₃]C), 1.13 (18H, t, J=7.3 Hz, CH₃-Et₃NH⁺).

4'-azido-5'-(ethyloxy-α,α-dimethylglycinyl)-phosphate cytidine (I-21) also was isolated from the chromatography as a byproduct.

³¹P-NMR (D₂O, 121 MHz): δ 5.51; ¹H-NMR (D₂0, 300 MHz): δ 7.71 (1H, d, J=7.5 Hz H-6), 6.05 (1H, m, J=3.1 Hz, H-1'), 5.97 (1H, d, J=7.5 Hz, H-5), 4.35-4.29 (2H, m, H-2', H-3'), 4.04 (H-5', J=7.1 Hz, OCH₂CH₃) 3.97-3.81 (2H, m, H-5'), 3.06 (6H, q, J=7.3 Hz, CH₂-Et₃NH⁺), 1.30 (6H, s, [CH₃]C), 1.18-1.13 (12H, m, CH₃-Et₃NH⁺, OCH₂CH₃). MS (ES⁻) m/e 476.3 (M⁻). Accurate mass: C₁₅H₂₃N₇O₉P requires 476.1295 found 476.1301.

EXAMPLE 19

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid sec-butyl ester (I-28)

step 1—2-butyloxy-L-alanine hydrochloride salt (14g)

The title compound was synthesised as described in Example 1 (A) utilizing L-alanine (8.0 g, 89.8 mmol), thionyl chloride (11.3 mL, 180 mmol), anhydrous 2-(R,S)-butanol (82 mL, 98 mmol) and toluene (200 mL). The 2-butyl ester (14 g) was isolated as a yellow foam (13.92 g, yield 85%) which was used in the next step without additional purification.

¹H-NMR (CDCl₃; 300 MHz): δ 8.59 (3H, bs, NH₃Cl), 4.89-4.83 (1H, m, CH-2-butyl), 4.17 (1H, bs, CH-Ala), 1.65 (3H, d, J=5.5 Hz, CH₃-Ala), 1.60-1.50 (2H, m, CH₂-2-butyl), 1.19-1.16 (3H, m, CH₃-2-butyl), 0.86-0.81 (3H, m, CH₃-2-butyl); ¹³C-NMR (CDCl₃; 75 MHz): δ 20.8 (CH₃-Ala), 27.3 (CH₃-2-butyl), 30.4, 30.5 (CH₃-2-butyl), 39.8 (CH₂-2-butyl), 60.6, 60.7 (CH-Ala), 86.1 (CH-2-butyl), 181.0 (C=O). MS (ES⁺) m/e 146 (MH⁺).

step 2—phenyl (benzyloxy-L-alaninyl)-phosphorochloridate (12g)

The title compound was synthesized by the procedure in Example 3 utilizing 14g (2.0 g, 9.36 11.0 mmol), phenyl dichlorophosphate (11a, 1.6 mL, 11.0 mmol), and TEA (3.1 mL, 22.0 mmol) in DCM (40 mL) to afford 2.33 g (66%) of 12g as an oil.

³¹P-NMR (CDCl₃, 121 MHz): δ 9.00, 9.35; ¹H-NMR (CDCl₃; 300 MHz): δ 7.45-7.22 (5H, m, Ph), 5.02-4.94 (1H, m, CH-2-butyl), 4.46, 4.36 (1H, bs, NH), 4.27-4.13 (CH-Ala), 1.73-1.48 (5H, m, CH₂-2-butyl, CH₃-Ala), 1.39-1.27 (3H, m, CH₃-2-butyl), 0.99-0.94 (3H, m, CH₃-2-butyl); ¹³C-NMR (CDCl₃; 75 MHz): δ 10.0 (CH₃-Ala), 19.7, 19.8 (CH₃-2-butyl), 21.1 (CH₃-2-butyl), 29.1 (CH₂-2-butyl), 5.10, 51.3 (CH-Ala), 74.8, 74.9 (CH-2-butyl), 120.9, 121.0, 126.4, 130.1, 130.4 (C-Ph), 150.1, 150.2 ('ipso', OPh), 172.6 (C=O).

step 3—4'-azido-5'-[phenyl-(2-butyloxy-L-alaninyl)]-phosphate cytidine (I-28)

The title compound was synthesized by the procedure in Example 4 utilizing 4'-azido-cytidine monohydrate (13b, 400.0 mg, 1.32 mmol) dissolved in anhydrous THF (15 mL), tert-BuMgCl (3.3 mL of solution 1M in THF, 2.9 mmol) and 12g (6.6 mL of a 0.5M solution in THF, 3.3 mmol). The reaction was monitored by TLC developed with CHCl₃:MeOH (8:2). The crude was purified by column chromatography and eluted with CHCl₃:MeOH (85:15). The recovered product was further purified by preparative TLC developed with CHCl₃:MeOH (85:15) to afford I-28 as a white solid (23.1 mg, yield 3%).

³¹P-NMR (CD₃OD, 121 MHz): δ 4.77, 4.61; ¹H-NMR (CD₃OD, 300 MHz): δ 7.68, 7.64 (1H, d, J=7.5 Hz, H-6), 7.41-7.19 (5H, m, Ph), 6.20-6.16 (1H, d, J=4.7 Hz, H-1'), 5.92, 5.87 (1H, d, J=7.5 Hz, H-5), 4.86-4.79 (1H, m, CH-2-butyl), 4.62-4.15 (4H, m, H-2', H-3', H-5'), 4.01-3.90 (CH-Ala), 1.66-1.53 (5H, m, CH₂-2-bl), 1.38-1.30 (CH₃-Ala), 1.23-1.19 (3H, m, CH₃-2-butyl), 0.91, 0.90 (3H, t, J=7.5 Hz, CH₃-2-butyl). MS (ES⁺) m/e 590.1 (MNa⁺). Accurate mass: C₂₂H₃₀N₇O₉NaP requires 590.1740 found 590.1754.

EXAMPLE 20

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid isopropyl ester (I-35)

step 1—4'-Azido-2',3'-isopropylidenecytidine-5'-O-[phenyl-(isopropoxy-L-alaninyl)]-phosphate (IV-2)

The title compound was prepared according to Example 4 utilizing 4'-azido-2',3'-isopropylidenecytidine (13f, 500 mg, 1.54 mmol), tert-BuMgCl (3.85 mL, 1 M solution in THF, 3.85 mmol) and phenyl-(isopropoxy-L-alaninyl)-phosphorochloridate (12e, 3.85 mmol, 3.85 mL, 1 M solution in THF) in dry THF (10 mL). The crude was purified by column chromatography eluting with a MeOH/DCM gradient (10 to 20% MeOH). The product was further purified by preparative TLC developed with MeOH/DCM (10:90) which afforded IV-2 as a white solid (300 mg, 30%).

³¹P NMR (121.5 MHz, d₄-MeOH): δ4.37, 4.25; ¹H NMR (300 MHz, d₄-MeOH): δ7.65 (1H, dd, J=7.8, 4.5 Hz, H-6), 7.36 (2H, m, Ph-CH), 7.28 (3H, m, Ph-CH), 5.89 (2H, m, H-1' and H-5), 5.18 (1H, dd, J=1.7, 6.4 Hz, H-2'), 5.09 (1H, m, H-3'), 4.35 (1H, m, ⁱPr—CH), 4.19-4.10 (2H, m, H-5'), 4.00

(1H, m, Ala-CH), 1.65 (3H, s, CH$_3$), 1.38 (6H, s, Ala-CH$_3$ and CH$_3$), 1.23 (6 H, m, $^i$Pr—CH$_3$); $^{13}$C NMR (75.5 MHz, d$_4$-MeOH): δ175.46, 175.40, 175.33, 175.25 (C=O), 168.47 (C-4), 158.06, 158.02 (C-2), 152.07, 152.48, 152.42, 152.38 (Ph-C), 146.17, 145.75 (C-6), 131.22 (Ar—C), 126.7 (Ar—C), 121.96, 121.91, 121.90, 121.84 ((Ar—C), 116.97, 116.92 (C(CH$_3$)$_2$), 100.99, 100.85 (C-5), 97.01, 96.61 (C-4'), 86.03, 85.95 (C-2'), 84.73, 84.75 (C-3'), 70.27, 70.21 (C-5'), 62.87 (I—Pr—CH), 26.57, 26.50 (CH$_3$), 25.65, 25.62 (CH$_3$), 21.02, 20.94, 20.86, 20.77 (Ala—CH$_3$), 14.93 (i-Pr—(CH$_3$)$_2$).

step 2—The title compound was prepared according to Example 7 utilizing 4'-azido-2',3'-isopropylidenecytidine-5'-[phenyl-(isopropoxy-L-alaninyl)]-phosphate (IV-2, 76 mg, 0.128 mmol) dissolved in a 60/40 HOAc/water mixture, and heated to 90° C. Removal of the solvents in vacuo and purification by preparative TLC purification developed with DCM/MeOH (9:1) afforded I-35 as a white solid (21 mg, 30%).

$^{31}$P NMR (121.5 MHz, d$_4$-MeOH): δ3.25, 3.06; $^1$H NMR (300 MHz, d$_4$-MeOH): 67.67-7.59 (1H, m, H-6), 7.39-7.33 (2H, m, Ph-CH), 7.27-7.17 (3H, m, Ph-CH), 6.19-6.13 (1H, dd, J=3.7 and 13.5 Hz, H-1'), 5.89-5.83 (1H, m, H-5), 4.97 (1H, m, H-2'), 4.35 (1H, m, H-3'), 4.29-4.16 (3H, m, i-Pr—CH and H-5'), 3.90 (1H, m, Ala—CH), 1.38-1.32 (3H, m, Ala—CH$_3$), 1.29-1.23 (6H, m, i-Pr—CH$_3$).

EXAMPLE 21

(R)-2-{[(2R,3S,4R,5R)-5-(4-Amino-2-oxo-2H-pyrimidin-1-yl)-2-azido-3,4dihydroxy-tetrahydro-furan-2-ylmethoxy]-phenoxy-phosphorylamino}-ropionic acid ethyl ester (1-43)

4-Amino-1-(6-azido-6-hydroxymethyl-2,2-dimethyl-tetrahydro-furo[3,4-d][1,3]dioxol-4-yl)-1H-pyrimidin-2-one (13f) was prepared from 4'azido-cytidine by standard methodology (see, e.g. T. W. Greene and P. G. M. Wuts; *Protecting Groups in Organic Synthesis, 3$^{rd}$* Ed., J. T. Wiley & Sons: New York, N.Y., 1999, pp. 207-215). 2-{[6-(4-Amino-2-oxo-2H-pyrimidin-1-yl)-4-azido-2,2-dimethyl-tetrahydro-furo[3,4-d][1,3]dioxol-4-ylmethoxy]-phenoxy-phosphorylamino}-propionic acid ethyl ester was prepared by condensing 13f and 12h as described in Example 4.

The title compound was prepared according to Example 7 by dissolving 2-{[6-(4-amino-2-oxo-2H-pyrimidin-1-yl)-4-azido-2,2-dimethyl-tetrahydro-furo[3,4-d][1,3]dioxol-4-ylmethoxy]-phenoxy-phosphorylamino}-propionic acid ethyl ester (40 mg, 0.07 mmol) in a 60/40 HOAc/water mixture and heating to 90° C. Removal of the solvents in vacuo and purification by preparative TLC purification developed with DCM/MeOH (9:1) afforded I-43 as a white solid (12 mg, 32%).

$^{31}$P NMR (121.5 MHz, d$_4$-MeOH): δ4.86, 4.33; $^1$H NMR (300 MHz, d$_4$-MeOH): δ7.69-7.62 (1H, m, H-6), 7.41-7.35 (2H, m, Ph-CH), 7.29-7.19 (3H, m, Ph-CH), 6.21-6.15 (m, 1H, H-1'), 5.92-5.86 (m, 1H, H-5), 4.47-4.06 (6H, m, H-2', H-3', H-5' and CH$_2$CH$_3$), 3.99-3.86 (m, 1H, Ala-CH), 1.38-1.28 (m, 3H, Ala-CH$_3$), 1.26-1.23 (m, 3H, CH$_2$CH$_3$).

EXAMPLE 22

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid benzyl ester (I-20)

The title compound was synthesized by the procedure in Example 4 utilizing 4'-azido-cytidine monohydrate (13b, 500.0 mg, 1.643 mmol) dissolved in anhydrous THF (13 mL), tert-BuMgCl (4.11 mL of solution 1M in THF, 4.11 mmol) and 12an (4.11 mL of a 1.0 M solution in THF, 4.11 mmol). The crude was purified by two column chromatographies eluting a DCM/MeOH gradient (10 to 20% MeOH). The product was further purified by a preparative TLC developed with DCM/MeOH (90:10) to afford I-20 as a white solid (49 mg, yield 5%).

$^{31}$P NMR (121.5 MHz, d$_4$-MeOH): δ4.70, 4.49; $^1$H NMR (300 MHz, d$_4$-MeOH): δ7.65-7.58 (1H, m, H-6), 7.36-7.34 (7H, m, Ph-CH), 7.26-7.19 (3H, m, Ph-CH), 6.20-6.13 (1H, dd, J=4.7 and 14.3 Hz, H-1'), 5.92-5.85 (1H, m, H-5), 5.20 (2H, s, Ph-CH$_2$), 4.37-4.29 (2H, m, H-2' and H-3'), 4.23-4.11 (2H, m, H-5'), 4.01 (1H, m, Ala-CH), 1.41-1.25 (3H, m, Ala-CH$_3$). $^{13}$C NMR (75.5 MHz, d$_4$-MeOH): δ174.94, 174.88, 174.62, 174.56 (C=O), 167.62 (C-4), 158.34 (C-2), 152.05, 151.97 (Ph-C), 143.12, 142.93 (C-6), 137.41, 137.25 (Ar—C), 130.96, 130.17, 130.31, 130.171 (Ar—C), 129.66, 129.59, 129.41, 129.36, 129.29 (Ar—C), 126.44 (Ar—C), 124.34 (Ar—C), 123.92 (Ar—C) 121.66, 121.60, 121.47, 121.41 (Ar—C), 121.28, 121.22 (Ar—C), 98.83, 98.72, 98.60 (C-5), 97.04 (C-4'), 93.87, 93.42 (C-1'), 74.57, 74.37 (C-3'), 73.50 (C-2'), 68.82, 68.75 (Bn-CH$_2$), 68.12, 67.74 (Ala-CH), 20.52, 20.43, 20.30, 20.20 (Ala-CH$_3$).

EXAMPLE 23

(S)-2-{[(3aS,4R,6R,6aR)-6-(4-Amino-2-oxo-2H-pyrimidin-1-yl)-4-azido-2,2-dimethyl-tetrahydro-furo[3,4-d][1,3]dioxol-4-ylmethoxy]-phenoxy-phosphorylamino}-propionic acid benzyl ester (IV-1)

The title compound was synthesized by the procedure in Example 4 utilizing 4'-azido-2',3'-isopropylidenecytidine (13f, 200 mg, 0.62 mmol) dissolved in anhydrous THF (10 mL), tert-BuMgCl (1.54 mL of solution 1M in THF, 1.54 mmol) and 12an (1.54 mL of a 1.0 M solution in THF, 1.54 mmol). The crude was purified by column chromatography eluting a DCM/MeOH gradient (90:10 to 80:20). The product was further purified by a preparative TLC developed with DCM/MeOH (90:10) to afford IV-1 as a white solid (170 mg, yield 67%).

$^{31}$P NMR (121.5 MHz, d$_4$-MeOH): δ4.31, 4.19; $^1$H NMR (300 MHz, d$_4$-MeOH): δ7.65-7.60 (1H, m, H-6), 7.32-7.21 (7H, m, Ph-CH), 7.32-7.21 (3H, m, Ph-CH), 5.88 (2H, m, H-1' and H-5), 5.15 (2H, m, H-2' and Bn-CH$_2$), 5.05 (2H, m, H-3' and Bn-CH$_2$), 4.29 (2H, m, H-5'), 4.06 (1H, m, Ala-CH), 1.66 (3H, s, CH$_3$), 1.38 (6H, m, CH$_3$ and Ala-CH$_3$).

EXAMPLE 24

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid tert-butyl ester (I-29)

step 1—Phenyl-(t-butyloxy-L-alaninyl)-phosphorochloridate (12f)

The title compound was synthesized by the procedure in Example 3 utilizing tert-butyloxy-L-alanine hydrochloride (14f, 1.30 g, 7.16 mmol), phenyl dichlorophosphate (11a, 1.1 mL, 7.16 mmol), and TEA (2.0 mL, 14.32 mmol) in DCM (40 mL) to afford 1.48 g (66%) of 12f as an oil.

$^{31}$P-NMR (CDCl$_3$, 121 MHz): δ 9.17, 9.54; $^1$H-NMR (CDCl$_3$; 300 MHz): δ 7.52-7.26 (5H, m, Ph), 4.53, 4.41 (1H, bs, NH), 4.18-4.05 (1H, m, CH-Ala), 1.55, 1.54 (3H, s, CH$_3$-t-butyl); $^{13}$C-NMR (CDCl$_3$; 75 MHz): δ20.9, 21.0 (CH$_3$-

Ala), 28.3 (CH₃-t-butyl), 51.3, 51.7 (CH-Ala), 83.0, 83.1 (C[CH₃]₃), 120.9, 121.0, 126.3, 130.3, 130.7 (C-Ph), 150.1, 150.2, 150.2, 150.3 ('ipso', OPh), 172.1, 172.2, 172.3 (C=O).

step 2—4'-azido-5'-[phenyl-(t-butyloxy-L-alaninyl)]-phosphate cytidine (I-29)

The title compound was synthesized by the procedure in Example 4 utilizing 4'-azido-cytidine monohydrate (13b, 350.0 mg, 1.15 mmol) dissolved in anhydrous THF (13 mL), tert-BuMgCl (2.9 mL of solution 1M in THF, 2.9 mmol) and 12f (5.8 mL of a 0.5M solution in THF, 2.9 mmol). The reaction was monitored by TLC (8:2 CHCl₃:MeOH). The crude was purified by column chromatography eluting with a CHCl₃:MeOH (85:15). The recovered product was further purified by preparative TLC (85:15 CHCl₃:MeOH) to afford I-29 as a white solid (18.6 mg, yield 3%).

$^{31}$P-NMR (CD₃OD, 121 MHz): δ 3.15, 3.25; $^1$H-NMR (CD₃OD, 300 MHz): δ 7.64, 7.61 (1H, d, J=7.5 Hz, H-6), 7.39-7.17 (5H, m, Ph), 6.17, 6.13 (1H, d, J=4.8 Hz, H-1'), 5.88, 5.86 (1H, d, J=7.5 Hz, H-5), 4.36-4.11 (4H, m, H-2', H-3', H-5'), 3.89-3.78 (1H, m, CH-Ala), 1.43 (3H, s, CH₃-t-butyl), 1.32-1.28 (3H, m, CH₃-Ala). MS (ES⁺) m/e 590.0 (MNa⁺). Accurate mass: C₂₂H₃₀N₇O₉NaP requires 590.1740 found 590.1751.

EXAMPLE 25

{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-acetic acid benzyl ester (I-33)

step 1—phenyl (benzyloxy-glycinyl)-phosphorochloridate (12a)

The title compound was synthesized by the procedure in Example 3 utilizing benzyl glycinate hydrochloride (14a, 2.00 g, 9.91 mmol), phenyl dichlorophosphate (11a, 1.5 mL, 9.91 mmol) and TEA (2.8 mL, 19.8 mmol) in DCM (50 mL) to afford 2.42 g (72%) of 12a as an oil.

$^{31}$P-NMR (CDCl₃, 121 MHz): δ 9.95; $^1$H-NMR (CDCl₃; 300 MHz): δ 7.50-7.24 (5H, m, Ph), 5.29 (2H, s, OCH₂-Ph), 4.40, 4.33 (1H, bs, NH), 4.04-3.97 (2H, m, CH₂-Gly); $^{13}$C-NMR (CDCl₃; 75 MHz): δ 43.6 (CH₂-Gly), 68.2 (CH₂-Ph), 120.9, 121.0, 121.1, 126.5, 126.5, 129.0, 129.1, 129.2, 130.4, 135.2 (C-Ph), 150.1, 150.2 ('ipso', OPh), 169.7, 169.8 (C=O).

step 2—4'-azido-5'-[phenyl (benzyloxy-glycinyl)]-phosphate uridine (I-33)

The title compound was synthesized by the procedure in Example 4 utilizing 4'-azido-uridine (13a 300.0 mg, 1.05 mmol) dissolved in anhydrous THF (13 mL), tert-BuMgCl (2.1 mL of solution 1M in THF, 2.10 mmol) and 12a (4.2 mL of a 0.5M solution in THF, 2.10 mmol). The reaction was monitored by TLC (9:1 CHCl₃:MeOH). The crude was purified by column chromatography eluting with a CHCl₃:MeOH (9:1). The recovered product was further purified by preparative TLC (9:1 CHCl₃:Me OH) to afford I-33 as a white solid (78.2 mg, yield 13%).

$^{31}$P-NMR (CD₃OD, 121 MHz): δ 4.23, 4.44; $^1$H-NMR (CD₃OD, 300 MHz): δ 7.63, 7.61 (1H, d, J=8.1 Hz, H-6), 7.37-7.15 (10H, m, Ph), 6.14-6.12 (1H, m, H-1'), 5.68, 5.63 (1H, d, J=8.1 Hz, H-5), 5.16 (2H, s, OCH₂-Ph), 4.37-4.16 (4H, m, H-2', H-3', H-5'), 3.83-3.78 (2H, m, CH₂-Gly). MS (ES⁺) m/e 611.0 (MNa⁺). Accurate mass: C₂₄H₂₅N₆O₁₀NaP requires 611.1267 found 611.1254.

EXAMPLE 26

({[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphoryl}-methyl-amino)-acetic acid ethyl ester (I-61)

The title compound was prepared as described in Example 4 utilizing 4'-azido-uridine (13a, 200 mg, 0.7 mmol), tert-BuMgCl (1.8 mL 1M solution in THF, 1.8 mmol), 12b (0.51 g, 1.75 mmol) and dry THF (10 mL). The crude was purified by two column chromatographies eluting with CHCl₃/MeOH (90:10) followed by two preparative TLC chromatographies developed with CHCl₃/MeOH (90:10) which afforded I-61 as a white solid (0.02 g, yield 5.4%).

$^{31}$P NMR (CD₄OD): δ4.39, 4.64; $^1$H NMR (CD₄OD): δ7.99 (1H, d, H6), 6.98-7.21 (5H, m, Ar—H), 6.21 (1H, dd, H1'), 5.83 (1H, dd, H5), 4.31-4.42 (2H, m, H2', H3'), 4.21 (2H, s, DH₂-CO₂Et), 4.11 (2H, q, O—CH₂—CH₃), 2.8 (3H, bs, N—CH₃), 1.46 (3H, t, O—CH₂—CH₃).

EXAMPLE 27

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid tert-butyl ester (I-50)

The title compound was synthesized by the procedure in Example 4 utilizing 4'-azido-uridine (13a, 200.0 mg, 0.70 mmol) dissolved in anhydrous THF (10 mL), tert-BuMgCl (1.4 mL of solution 1M in THF, 1.40 mmol) and 12f (2.8 mL of a 0.5M solution in THF, 1.40 mmol). The reaction was monitored by TLC (9:1 CHCl₃:MeOH). The crude was purified by column chromatography eluting with a CHCl₃:MeOH (9:1). The recovered product was further purified by preparative TLC and eluted with CHCl₃:MeOH (9:1) to afford I-50 as a white solid (45.2 mg, yield 11%).

$^{31}$P-NMR (CD₃OD, 121 MHz): δ 4.99, 4.73; $^1$H-NMR (CD₃OD, 300 MHz): δ 7.67, 7.64 (1H, d, J=8.1 Hz, H-6,), 7.37-7.15 (5H, m, Ph), 6.20-6.15 (1H, m, H-1'), 5.75, 5.68 (1H, d, J=8.1 Hz, H-5), 4.24-4.14 (4H, m, H-2', H-3', H-5'), 3.91-3.84 (1H, m, CH-Ala), 1.48 (3H, s, CH₃-t-butyl),1.46-1.32 (3H, ,m Ch₃-Ala). $^{13}$C-NMR (CD₃OD; 75 MHz): δ 21.1, 21.2 (CH₃-Ala), 28.6 (C[CH₃]₃) 52.5, 52.7 (CH-Ala), 69.2, 69.3 (C-5'), 74.0, 74.2 (C-2', C-3'), 83.1, 83.2 (C[CH₃]₃), 92.3, 92.8 (C-1'), 99.0, 99.1 (C-5), 104.0, 104.1 (C-4'), 121.7, 121.8, 126.8, 131.3, (C-Ph), 142.9, 143.0 (C-6), 152.4, 152.6 ('C-ipso' O-Ph, C-2), 166.2 (C-4), 174.4, 174.3 (C=O).

EXAMPLE 28

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid ethyl ester (I-34)

The title compound was synthesized by the procedure in Example 7. 4'-Azido-2',3'-isopropylidenecytidine-5'-[phenyl-(ethoxy-L-alaninyl)]-phosphate (IV-3, 95 mg, 0.159 mmol) was dissolved in a 60/40 HOAc/water (5 mL), and heated to 90° C. After removal of the solvents in vacuo the crude product was purified by preparative TLC purification (9:1 DCM/MeOH) which afforded I-34 as a white solid (40 mg, 45%).

$^{31}$P NMR (121.5 MHz, d₄-MeOH): δ4.75, 4.60; $^1$H NMR (300 MHz, d₄-MeOH): δ7.69-7.62 (1H, m, H-6), 7.41-7.35

(2H, m, Ph-CH), 7.29-7.19 (3H, m, Ph-CH), 6.21-6.15 (1H, m, H-1'), 5.92-5.86 (1H, m, H-5), 4.63-4.11 (6H, m, H'-2, H-3', H-5' and $CH_2CH_3$), 3.96 (m, 1H, Ala-CH), 1.38-1.28 (m, 3H, Ala-$CH_3$), 1.26-1.23 (m, 3H, $CH_2CH_3$); $^{13}C$ NMR (75.5 MHz, $d_4$-MeOH): δ175.56, 175.51, 175.29, 175.23 (C=O), 168.07 (C-4), 152.38, 152.30 (Ar—C), 143.52, 143.35 (C-6), 131.30 (Ar—C), 126.81 (Ar—C), 121.81, 121.74 (Ar—C), 99.13, 99.00, 98.89 (C-5), 97.34 (C-4'), 94.26, 93.87 (C-1'), 74.87, 74.70 (C-3'), 73.85 (C-2'), 69.22, 69.08, 69.02 (C-5'), 62.93 ($CH_2CH_3$), 52.15, 51.98 (Ala-CH, q).

EXAMPLE 29

(S)-2-{[(2R,3S,4R,5R)-5-(2,4-Dioxo-3,4-dihydro-2H-pyrimidin-1-yl)-2-ethynyl-3,4-dihydroxy-tetrahydro-furan-2-ylmethoxy]-phenoxy-phosphorylamino}-propionic acid tert-butyl ester (I-42)

The title compound was synthesized by the procedure in Example 4 utilizing 4'-ethynyl-uridine (13c 150.0 mg, 0.56 mmol) dissolved in anhydrous THF (10 mL), tert-BuMgCl (1.1 mL of solution 1M in THF, 1.10 mmol) and 12f (2.2 mL of a 0.5M solution in THF, 1.12 mmol). The reaction was monitored by TLC (9:1 $CHCl_3$:MeOH). The crude was purified by column chromatography eluting with a $CHCl_3$:MeOH (9:1). The recovered product was further purified twice by preparative thin layer chromatography. The first plate was developed with a $CHCl_3$:MeOH (9:1) and the second plate with a $CHCl_3$:MeOH (95:5) to afford I-42 as a white solid (43.9 mg, yield 14%).
$^{31}$P-NMR ($CD_3OD$, 121 MHz): δ 4.73, 4.58; $^1$H-NMR ($CD_3OD$, 300 MHz): δ 7.63, 7.60 (1H, d, J=8.1 Hz, H-6,), 7.40-7.21 (5H, m, Ph), 6.03-6.00 (1H, m, H-1'), 5.69, 5.65 (1H, d, J=8.1 Hz, H-5), 4.34-4.20 (4H, m, H-2', H-3', H-5'), 3.89-3.83 (1H, m, CH-Ala), 3.33-3.32 (1H, m, ≡CH), 1.46 (3H, s, $CH_3$-t-butyl), 1.36-1.33 (3H, m, $CH_3$-Ala). $^{13}$C-NMR ($CD_3OD$; 75 MHz): δ 20.3, 20.4, 20.5, 20.6 ($CH_3$-Ala), 28.1, 28.3 (C[$CH_3$]$_3$) 52.0, 52.2 (CH-Ala), 69.5, 69.6, 69.7, 69.7 (C-5'), 71.8, 73.9, 74.0 (C-2', C-3'), 78.6, 79.0, 79.4, 80.1, 82.6, 82.7, 82.9, 83.1, 83.2 (C≡CH, C≡CH, C-4', C[$CH_3$]$_3$), 91.0, 91.1 (C-1'), 103.3, 103.4 (C-5), 121.3, 121.4, 126.2, 130.7, (C-Ph), 142.5, 142.6 (C-6), 151.9, 152.0, 152.1, 152.2 ('C-ipso' O-Ph, C-2), 165.8 (C-4), 173.8, 173.9, 174.0, 174.2 (C=O). MS (ES$^+$) m/e 574.1 (MNa$^+$). Accurate mass: $C_{24}H_{30}N_3O_{10}NaP$ requires 574.1567 found 574.1575.

EXAMPLE 30

{[(2R,3S,4R,5R)-5-(2,4-Dioxo-3,4-dihydro-2H-pyrimidin-1-yl)-2-ethynyl-3,4-dihydroxy-tetrahydro-furan-2-ylmethoxy]-phenoxy-phosphorylamino}-acetic acid benzyl ester (I-49)

The title compound was synthesized by the procedure in Example 4 utilizing 4'-ethynyl-uridine (13a, 106.7 mg, 0.40 mmol) dissolved in anhydrous THF (10 mL), tert-BuMgCl (0.80 mL of solution 1M in THF, 0.80 mmol) and 12a (1.6 mL of a 0.5M solution in THF, 0.80 mmol). The reaction was monitored by TLC developed with $CHCl_3$:MeOH (9:1). The crude was purified by column chromatography eluting with a $CHCl_3$:MeOH (95:5). The recovered product was further purified twice by preparative thin layer chromatography. The first plate was developed two times with $CHCl_3$:MeOH (95:5), and the second plate was developed four times with $CHCl_3$:MeOH (95:5), to afford I-49 as a white solid (25.2 mg, yield 11%).

$^{31}$P-NMR ($CD_3OD$, 121 MHz): δ 5.89, 5.60; $^1$H-NMR ($CD_3OD$, 300 MHz): δ 7.53, 7.48 (1H, d, J=8.1 Hz, H-6), 7.32-7.10 (10H, m, Ph), 5.96-5.92 (1H, m, H-1'), 5.59, 5.54 (1H, d, J=8.1 Hz, H-5), 5.43 (2H, s, $OCH_2$,-Ph), 4.34-4.09 (4H, m, H-2', H-3', H-5'), 3.78-3.71 (2H, m, $CH_2$-Gly), 3.33 (1H, m, "CH).

EXAMPLE 31

(S)-2-{[(2R,3S,4R,5R)-5-(2,4-Dioxo-3,4-dihydro-2H-pyrimidin-1-yl)-2-ethynyl-3,4-dihydroxy-tetrahydro-furan-2-ylmethoxy]-phenoxy-phosphorylamino}-propionic acid benzyl ester (I-56)

The title compound was prepared as described in Example 4 utilizing 4'-ethynyl-uridine (13c, 150 mg, 0.56 mmol), tert-BuMgCl (1.2 mL 1M solution in THF, 1.2 mmol), phenyl-(benzyloxy-L-alaninyl)-phosphorochloridate (12an 1.2 mL of a 1M solution in THF, 1.2 mmol) and dry THF (10 mL). The crude was purified by column chromatography eluting with a $CHCl_3$/MeOH gradient (10 to 20% MeOH). The product was further purified by preparative TLC and developed with $CHCl_3$/MeOH (90:10) which afforded I-56 as a white solid (40 mg, yield 12%).
$^{31}$P NMR (121.5 MHz, $d_4$-MeOH): δ4.64, 4.42; $^1$H NMR (300 MHz, $d_4$-MeOH): δ7.61-7.54 (1H, dd, J=8.2, 12.2 Hz, H-6), 7.39-7.29 (7H, m, Ph-CH), 7.26-7.08 (3H, m, Ph-CH), 6.02-5.99 (1H, m, H-1'), 5.70-5.60 (1H, dd, J=19.7, 8.0 Hz, H-5), 5.16 (2H, m, Bn-$CH_2$), 4.33-4.19 (4H, m, H-2', H-3' and H-5'), 4.33-3.99 (1H, m, Ala-CH), 3.20 (1H, m, C≡C—H), 1.39-1.31 (3H, m, Ala-$CH_3$); $^{13}$C NMR (75.5 MHz, $d_4$-MeOH): δ174.93 (C=O), 166.34 (C-4), 152.36 (C-2 and Ph-C), 143.04 (C-6), 137.60 (Ar—C), 131.27 (Ar—C), 130.01, 129.72 (Ar—C), 126.71 (Ar—C), 121.85, 121.78 (Ar—C), 103.84 (C-5), 91.65, 91.55 (C-1'), 83.57, 83.45 (C≡C), 74.53, 74.43 (C-2'), 72.34, 72.29 (C-3'), 70.19 (C≡C), 68.45 (C-5' and Bn-$CH_2$), 52.01 (Ala-CH), 20.86, 20.78 (Ala-$CH_3$).

EXAMPLE 32

(R)-2-{[(2R,3S,4R,5R)-5-(2,4-Dioxo-3,4-dihydro-2H-pyrimidin-1-yl)-2-ethynyl-3,4-dihydroxy-tetrahydro-furan-2-ylmethoxy]-phenoxy-phosphorylamino}-propionic acid benzyl ester (I-41)

The title compound was synthesized by the procedure in Example 4 utilizing 4'-ethynyl-uridine (13c, 150 mg, 0.559 mmol), tert-BuMgCl (1.1 mL of solution 1M in THF, 1.119 mmol) and phenyl (benzyloxy-D-alaninyl)phosphorochloridate (12m, 1.1 mL of solution 1M in THF, 1.119 mmol)). The crude was purified by column chromatography eluting with a $CHCl_3$:MeOH (90:10). The recovered product was further purified by preparative silica gel thin layer chromatography developed with $CHCl_3$/MeOH (9:1) which afforded I-41 as a white solid (100 mg, 0.1723 mmol, yield 17%).
$^{31}$P NMR ($d_4$-$CH_3OH$): δ4.80, 4.14; $^1$H NMR ($d_4$-$CH_3OH$): δ7.55 (1H, m, H6-uridine), 7.35 (7H, m, CH-phenyl), 7.23 (3H, m, CH-phenyl), 6.00 (1H, m, H1'-uridine), 5.65 (1H, m, H2-uridine), 5.16 (2H, s, $CH_2$-benzyl), 4.32 (1H, m, H3'-cytidine), 4.28 (1H, m, H2'-cytidine), 4.15 (2H, m, H5'-cytidine), 4.05 (1H, m, CHα), 3.18 (1H, CH-ethynyl), 1.36 (3H, m, $CH_3$-alanine); $^{13}$C NMR ($d_4$-$CH_3OH$): δ6175.33, 175.28, 175.01 (1C, C=O ester), 166.37 (1C, C4-uridine), 152.68, 152.58, 152.39, 152.32 (1C, C2-uridine), 143.13, 143.06 (1C, C6-uridine), 137.62, 137.55 (1C, C-phenyl), 131.30, 131.27 (2C, CH-phenyl), 130.01 (2C, CH-phenyl), 129.78, 129.76, 129.71 (2C, CH-phenyl), 127.42 (1C, C-ethynyl), 126.77 (1C, CH-phenyl), 121.91, 121.85, 121.77, 121.70 (2C, CH-phenyl), 103.87, 103.82 (lC, C5-uridine), 99.11, 98.98 (1C, C4'-uridine), 91.97, 91.41 (1C, C1'-uridine), 74.55, 74.44 (1C, C3'-uridine), 72.40, 71.99 (1C, C2'-uridine), 70.32, 70.25 (1C, CH-ethynyl), 69.62, 69.56 (1C, CH$_2$-benzyl), 68.53, 68.45 (1C, C5'-uridine), 52.17, 51.89 (1C, CHα), 20.87, 20.78, 20.68 (1C, CH$_3$-lateral chain); MS (ES) m/e: 608.1 (MNa$^+$, 100%); Accurate mass: C$_{27}$H$_{28}$N$_3$O$_{10}$NaP required 608.1410, found 608.1402.

EXAMPLE 33

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-3-phenyl-propionic acid ethyl ester (I-73)

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-hydroxy-phosphorylamino}-3-phenyl-propionic acid; compound with ammonia (I-72) and (S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-hydroxy-phosphorylamino}-3-phenyl-propionic acid ethyl ester; compound with ammonia (I-71)

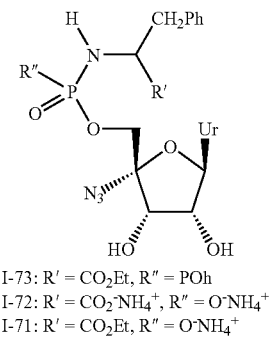

I-73: R' = CO$_2$Et, R" = POh
I-72: R' = CO$_2^-$NH$_4^+$, R" = O$^-$NH$_4^+$
I-71: R' = CO$_2$Et, R" = O$^-$NH$_4^+$

The title compound I-71 was synthesized by the procedure in Example 4 utilizing 4'-azido-uridine (13a, 300 mg, 1.05 mmol) dissolved in anhydrous THF (13 mL), tert-BuMgCl (2.1 mL of solution 1M in THF, 2.1 mmol) and 12u (4.2 mL of a 0.5M solution in THF, 2.1 mmol). The reaction was monitored by TLC (9:1 CHCl$_3$:MeOH). PS-Trisamine resin (1.5 g, 6.16 mmol) was added and the reaction mixture was stirred for 1 h. The resin was filtered and the solvent removed in vacuo to afford a crude product which was purified by column chromatography and eluted with CHCl$_3$:MeOH (9:1). The recovered product was further purified by column chromatography and eluted with CHCl$_3$:MeOH (93:7) to afford I-73 as a white solid (73.7 mg, yield 11%).

$^{31}$P-NMR (CD$_3$OD, 121 MHz): δ 4.54, 4.31; $^1$H-NMR (CD$_3$OD, 300 MHz): δ 7.58, 7.55 (1H, d, J=8.0 Hz, H-6,), 7.38-7.07 (10H, m, Ph), 6.17, 6.11 (1H, d, J=5.3Hz, H-1'), 5.74, 5.64 (1H, d, J=8.0 Hz, H-5), 4.33-3.74 (7H, m, H-2', H-3', H-5', CH-Phe, OC$\underline{\text{H}}_2$CH$_3$), 3.55-2.86 (2H, m, CH$_2$-Phe), 1.24-1.16 (3H, m, OCH$_2$C$\underline{\text{H}}_3$); $^{13}$C-NMR (CD$_3$OD; 75 MHz): δ 14.8, 14.9 (OCH$_2$$\underline{\text{C}}$H$_3$), 41.3, 41.4 (CH$_2$-Phe), 58.2, 58.4 (CH-Phe), 62.8, 62.9 (O$\underline{\text{C}}$H$_2$CH$_3$), 68.8 (C-5'), 74.0, 74.2 (C-2', C-3'), 92.5 (C-1'), 98.7, 98.9 (C-5), 104.0, 104.1 (C-4'), 121.4, 121.5, 121.7, 121.8, 126.7, 128.4, 130.0, 130.9, 131.3, 138.5 (C-Ph), 142.6, 143.0 (C-6), 152.2, 152.3, 152.6 ('C-ipso' O-Ph, C-2), 166.2 (C-4), 174.2, 174.3 (C=O).

I-73 (54.4 mg, 0.089 mmol) was dissolved in a 4:1 TEA/H$_2$O (2.5 mL) solution and the reaction mixture was stirred at RT for 2 days. The solvent was removed in vacuo and the crude was purified by a flash chromatography and eluted with i-PrOH/NH$_3$/H$_2$O (9:0.3:0.7) to afford I-72 as a white solid (15.8 mg, yield 32%).

$^{31}$P-NMR (D$_2$O, 121 MHz): δ 7.33; $^1$H-NMR (D$_2$O, 300 MHz): δ 7.65 (1H, d, J=8.1 Hz H-6), 7.21-7.10 (5H, m, H-Ph), 5.99 (1H, d, J=4.5 Hz H-1'), 5.78 (1H, d, J=8.1 Hz, H-5), 4.30-4.18 (2H, m, H-2', H-3'), 3.65-3.53 (3H, m, H-5', CH-Phe), 2.80-2.77 (2H, m, CH$_2$-Phe).

I-71 also was isolated from the hydrolysis of I-73 as a white solid (20.8 mg, yield 42%).

$^{31}$P-NMR (D$_2$O, 121 MHz): δ 6.56; $^1$H-NMR (D$_2$O, 300 MHz): δ 7.70 (1H, d, J=8.1 Hz H-6), 7.29-7.16 (5H, m, H-Ph), 6.09 (1H, d, J=4.1 Hz H-1'), 5.84 (1H, d, J=8.1 Hz, H-5), 4.69-4.62 (2H, m, H-2', H-3'), 4.40-3.64 (7H, m, H-5', CH-Phe, OC$\underline{\text{H}}_2$CH$_3$), 3.19-3.12 (2H, m, CH$_2$-Phe), 1.14-1.02 (3H, m, OCH$_2$C$\underline{\text{H}}_3$).

EXAMPLE 34

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-3-phenyl-propionic acid benzyl ester (I-8)

The title compound was prepared as described in Example 4 utilizing 4'-azido-uridine (13a, 200 mg, 0.701 mmol), tert-BuMgCl (1.75 mL 1M solution in THF, 1.75 mmol), dry THF (10 mL), dry THF (10 mL) and 12w (1.75 mL 1M solution of THF, 1.75 mmol). The crude was purified by column chromatography and eluted with a CHCl$_3$/MeOH gradient (10 to 20% MeOH) followed by a preparative TLC developed with CHCl$_3$/MeOH (90:10) which afforded I-8 as a white solid (20 mg, yield 15%).

$^{31}$P NMR (121.5 MHz, CDCl$_3$): δ4.56, 4.47; $^1$H NMR (300 MHz, d$_4$-MeOH): δ7.55 (1H, m, H-6), 7.33-7.01 (15H, m, Ph-CH), 6.15-6.08 (1H, m, H-1'), 5.69-5.58 (1H, m, H-5), 5.08 (2H, m, Bn-CH$_2$), 4.50 (1H, br, H-2') 4.29-4.06 (2H, m, H-5'), 3.99-3.66 (2H, m, H-3' and Phe-CH), 3.15-3.00 (1H, m, Bn-CH$_2$), 2.91-2.84 (1H, m, Bn-CH$_2$).

EXAMPLE 35

1-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-cyclopentanecarboxylic acid benzyl ester (II-3)

step 1—cyclopentylglycine benzyl ester p-toluene sulfonate salt

Cyclopentylglycine benzyl ester p-toluene sulfonate salt was prepared by the procedure in Example 1(C) from cyclopentylglycine (5.0 g, 39.0 mmol), TsOH monohydrate (8.159 g, 42.9 mmol), benzyl alcohol (20.4 mL, 194 mmol) and toluene (50 mL). The product 14al was isolated as white solid (9.15 g, 23.4 mmol, 60%).

δ$_H$ (d$_4$-CH$_3$OH): 8.56 (3H, s, NH$_3^+$-amino acid ester), 7.72 (2H, d, tosylate, J=9.0 Hz), 7.4 (2H, m, CH-phenyl), 7.35-7.30 (5H, m, CH-phenyl), 7.25 (2H, d, CH-phenyl-tosylate, J=9.0 Hz), 5.28 (2H, s, CH$_2$-benzyl), 2.37 (3H, s, CH$_3$-tosylate), 2.33 (2H, m, CH$_2$-cyclopentyl), 1.93 (2H, m, CH$_2$-cylopentyl), 1.89 (2H, m, CH$_2$-cyclopentyl).

step 2—phenyl-(benzyloxy-cyclopentylglycinyl)phosphorochloridate

The title compound was prepared as described in Example 3 utilizing phenyl dichlorophosphate (11a, 1.56 mL, 7.67 mmol), 14al (3.0 g, 7.67 mmol), dry TEA (2.138 mL, 15.34 mmol) and dry DCM (15 mL). The product 12al was obtained as a clear yellow oil (2.57 g, 6.54 mmol, 85%).

$^{31}$P NMR (CDCl$_3$): δ7.90; $^1$H NMR (CDCl$_3$): δ7.96 (2H, d, CH-phenyl, J=8.4 Hz),7.44 (2H, m, CH-phenyl), 7.39 (4H, m, CH-phenyl), 7.27 (2H, d, CH-phenyl, J=8.4 Hz), 5.24 (2H, s, CH$_2$-benzyl), 4.65 (1H, s, NH), 2.43 (4H, m, CH$_2$-cyclopentyl), 1.98 (4H, CH$_2$-cyclopentyl).

step 3—azido-cytidine 5'-O-[phenyl(benzyloxy-cyclopentylglycinyl)] phosphate (II-3)

The title compound was prepared as described in Example 4 utilizing 4'-azido-cytidine (13b, 300 mg, 0.986 mmol), tert-BuMgCl (2.46 mL, 1M solution in THF, 2.46 mmol) and phenyl-(benzyloxy-cyclopentylglycinyl)phosphorochloridate (12al, 2.46 mL of solution 1M in THF, 2.46 mmol). The crude was purified twice by column chromatography, using CHCl$_3$/MeOH (95:5) as eluent for the first column and CHCl$_3$/MeOH (80:20) for the second column. The product from the second chromatography was further purified by preparative silica TLC developed with CHCl$_3$/MeOH (9:1) to afford II-3 a white solid (30 mg, 0.047 mmol, 5%).

$^{31}$P NMR (d$_4$-CH$_3$OH): δ$_P$ 3.70, 3.67; $^1$H NMR (d$_4$-CH$_3$OH): δ$_H$ 7.55 (1H, m, H6-cytidine, J=7.3 Hz), 7.24 (7H, m, CH-phenyl), 7.13 (3H, m, CH-phenyl), 6.07 (1H, m, H1'-cytidine), 5.75 (1H, m, H5-cytidine, J=7.3 Hz), 5.05 (2H, s, CH$_2$-benzyl), 4.23 (1H, m, H2'-cytidine), 4.15 (1H, m, H3'-cytidine), 4.10 (2H, m, H5'-cytidine), 2.00 (2H, m, CH$_2$-cyclopentyl), 1.92 (2H, m, CH$_2$-cyclopentyl), 1.63 (2H, m, CH$_2$-cyclopentyl), 1.55 (2H, m, CH$_2$-cyclopentyl); $^{13}$C NMR (d$_4$-CH$_3$OH): δ$_C$ 176.82 (1C, C=O ester), 167.99 (1C, C4-cytidine), 158.56 (1C, C2-cytidine), 152.49, 152.42 (1C, C-phenyl), 143.48, 143.36 (1C, C6-cytidine), 137.74, 137.73 (1C, C-phenyl), 131.73, 131.55, 131.20 (2C, CH-phenyl), 130.20, 129.98 (1C, CH-phenyl), 129.73, 129.71, 129.71, 129.69 (2C, CH-phenyl), 129.59, 129.45 (1C, CH-phenyl), 127.37, 126.70 (1C, CH-phenyl), 122.05, 121.99, 121.92 (1C, phenyl), 99.16, 99.04, 99.02 (1C, C5-cytidine), 97.24 (1C, C4'-cytidine), 93.87, 93.75 (1C, C1'-cytidine), 74.88, 74.84 (1C, C3'-cytidine), 73.79, 73.70 (1C, C2'-cytidine), 69.16, 69.07, 68.99, 68.76 (1C, C5'-cytidine), 68.72 (1C, C-cyclopentyl), 68.61 (1C, CH$_2$-benzyl), 40.34, 40.23, 40.16, 40.05 (1C, CH$_2$-cyclopentyl), 39.62, 39.56, 39.50 (1C, CH$_2$-cyclopentyl), 25.10, 25.00 (1C, CH$_2$-cyclopentyl), 24.98 (1C, CH$_2$-cyclopentyl).

EXAMPLE 36

1-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-cyclopentanecarboxylic acid ethyl ester (II-1)

step 1—cyclopentylglycine ethyl ester hydrochloride salt

Cyclopentylglycine ethyl ester hydrochloride salt was prepared by the procedure in Example 1(B) utilizing cyclopentylglycine (5.0 g, 38.7 mmol), thionyl chloride (6.0 mL, 77.4 mmol) and EtOH (34.10 mL, 58.1 mmol). The ethyl ester 14aj was obtained as a white solid (2.25 g, 10.86 mmol, 56%).

$^1$H NMR (d$_6$-DMSO): δ$_H$ 8.82 (3H, s, NH$_3^+$-amino acid ester), 4.19 (2H, m, CH$_2$-ethyl, J=7.1 Hz), 2.08 (2H, m, CH$_2$-cyclopentyl), 1.96 (2H, m, CH$_2$-cyclopentyl), 1.89 (2H, m, CH$_2$-cyclopentyl), 1.72 (2H, m, CH$_2$-cyclopentyl), 1.23 (3H, t, CH$_3$-ethyl, J=7.1 Hz).

step 2—phenyl-(ethoxy-cyclopentylglycinyl)phosphorochloridate

The title compound was prepared as described in Example 3 utilizing phenyl dichlorophosphate (11a, 2.64 mL, 12.9 mmol), 14aj (2.5 g, 12.9 mmol), dry TEA (3.60 mL, 25.8 mmol) and dry DCM (15 mL). The phosphorochloridate 12aj was obtained as a clear white solid (3.37 g, 10.19 mmol, 79%).

$^{31}$P NMR (CDCl$_3$): δ$_P$ 8.09; $^1$H NMR (CDCl$_3$): δ$_H$ 7.47 (1H, m, CH-phenyl), 7.34 (2H, m, CH-phenyl, 7.30 (2H, m, CH-phenyl), 4.74 (1H, s, NH), 4.27 (2H, m, CH$_2$-ethyl, J=6.7 Hz), 2.30 (4H, m, CH$_2$-cyclopentyl), 1.92 (2H, m, CH$_2$-cyclopentyl), 1.87 (2H, m, CH$_2$-cyclopentyl), 1.35 (3H, t, CH$_3$-ethyl, J=6.7 Hz).

step 3—azido-cytidine 5'-O-[phenyl(ethoxy-cyclopentylglycinyl)phosphate (II-1)

The title compound was prepared as described in Example 4 utilizing 4'-azido-cytidine (13b, 300 mg, 0.986 mmol), tert-BuMgCl (2.46 mL 1M solution in THF, 2.46 mmol) and 12aj (2.46 mL 1M solution of THF, 2.46 mmol). The crude was purified by column chromatography and eluted with CHCl$_3$/MeOH (95:5) followed by a preparative TLC developed with CHCl$_3$/MeOH (85:15) which afforded II-1 as a white solid (100 mg, 0.172 mmol, 18%).

$^{31}$P NMR (d$_4$-CH$_3$OH): δ$_P$ 3.74; 1H NMR (d$_4$-CH$_3$OH): δ$_H$ 7.70 (1H, m, H6-cytidine, J=7.6 Hz), 7.38 (2H, m, CH-phenyl), 7.36 (1H, m, CH-phenyl), 7.25 (2H, m, CH-phenyl), 6.19 (1H, m, H1'-cytidine), 5.87 (1H, m, H2-cytidine, J=7.6 Hz), 4.37 (1H, m, CH$_2$-ethyl), 4.28 (1H, m, H2'-cytidine), 4.26 (1H, m, H3'-cytidine), 4.15 (2H, m, H5'-cytidine), 2.00 (2H, m, CH$_2$-cyclopentyl), 1.92 (2H, m, CH$_2$-cyclopentyl), 1.63 (2H, m, CH$_2$-cyclopentyl), 1.55 (2H, m, CH$_2$-cyclopentyl), 1.25 (3H, m, CH$_3$-ethyl); 13C NMR (d$_4$-CH$_3$OH): δ$_C$ 177.05 (1C, C=O ester), 168.05 (1C, C4-cytidine), 158.62 (1C, C2-cytidine), 152.52, 152.43 (1C, C-phenyl), 143.51, 143.43 (1C, C6-cytidine), 131.00 (2C, CH-phenyl), 126.70 (1C, CH-phenyl), 122.07, 122.00, 121.93 (2C, CH-phenyl), 99.22, 99.19, 99.09, 99.05 (1C, C5-cytidine), 97.21 (1C, C4'-cytidine), 93.86, 93.79 (1C, C1'-cytidine), 74.86 (1C, C3'-cytidine), 73.87, 73.79 (1C, C2'-cytidine), 69.20, 69.12, 69.05 (1C, C5'-cytidine), 68.72, 68.69 (1C, C-cyclopentyl), 62.93 (1C, CH$_2$-ethyl), 40.35, 40.23 (1C, CH$_2$-cyclopentyl), 40.10, 39.54 (1C, CH$_2$-cyclopentyl), 25.11, 25.00 (1C, CH$_2$-cyclopentyl), 24.98 (1C, CH$_2$-cyclopentyl), 14.86 (1C, CH$_3$-ethyl).

EXAMPLE 37

1-{[(2R,3S,4R,5R)-5-(4-Amino-2-oxo-2H-pyrimidin-1-yl)-2-azido-3,4-dihydroxy-tetrahydro-furan-2-ylmethoxy]-hydroxy-phosphorylamino}-cyclopentanecarboxylic acid ethyl ester; triethyl-amine (II-6)

To a stirring solution of TEA (2 mL, 0.014 mmol) and water (8 mL, 0.444 mmol) was added azido-cytidine 5'-O-[phenyl(ethoxy-cyclopentylglycinyl)phosphate (II-1, (240 mg, 0.414 mmol). The reaction was stirred for three days. The solvent was removed in vacuo to give a white solid that was crystallized from acetone to afford II-6 as a white solid precipitate (5.6 mg, 0.0096 mmol, 2%).

$^{31}$P NMR (D$_2$O): δ4.67; $^1$H NMR (D$_2$O): δ7.73 (1H, d, H6-cytidine, J=7.6 Hz), 6.05 (1H, d, H1'-cytidine), 5.98 (1H, d, H5-cytidine, J=7.6 Hz), 4.35 (2H, s, H2'-cytidine, H3'-cytidine), 4.05 (2H, m, CH$_2$-ethyl, J=7.1 Hz), 3.90 (2H, m, H5'-cytidine), 3.08 (6H, m, CH$_2$-NH$^+$-triethylamonium salt), 1.90 (2H, m, CH$_2$-cyclopentyl), 1.78 (2H, m, CH$_2$-cyclopentyl), 1.60 (2H, m, CH$_2$-cyclopentyl), 1.55 (2H, m, CH$_2$-cyclopentyl), 1.18 (3H, m, CH$_3$-ethyl, J=7.1 Hz), 1.14 (9H, m, CH$_3$- NH$^+$-Et$_3$NH salt).

EXAMPLE 38

1-{[(2R,3S,4R,5R)-2-Azido-5-(2,4-dioxo-3,4-dihydro-2H-pyrimidin-1-yl)-3,4-dihydroxy-tetrahydrofuran-2-ylmethoxy]-phenoxy-phosphorylamino}-cyclopentanecarboxylic acid benzyl ester (II-4)

The title compound was prepared as described in Example 4 utilizing 4'-azido-uridine (13a, 300 mg, 1.052 mmol), tert-BuMgCl (2.10 mL 1M solution in THF, 2.10 mmol) and phenyl(benzyloxy-cyclopentylglycinyl)phosphorochloridate (12al, 2.10 mL 1M solution of THF, 2.10 mmol). The crude was purified by column chromatography and eluted with CHCl$_3$/MeOH (95:5) followed by a silica gel preparative TLC developed with CHCl$_3$/MeOH (9:1) which afforded II-4 as a white solid (130 mg, 0.202 mmol, 20%).

$^{31}$P NMR (d$_4$-CH$_3$OH): δ3.77, 3.74; $^1$H NMR (d$_4$-CH$_3$OH): δ7.58 (1H, m, H6-uridine, J=8.13 Hz), 7.28 (7H, m, 5 CH-phenyl, 2 CH-benzyl), 7.15 (3H, m, CH-benzyl), 6.09 (1H, m, H1'-uridine), 5.55 (1H, m, H5-uridine, J=8.13 Hz), 5.08 (2H, s, CH$_2$-phenyl), 4.29 (1H, m, H2'-uridine), 4.24 (1H, m, H3'-uridine), 4.09 (2H, m, H5'-uridine), 2.04 (2H, m, CH$_2$-cyclopentyl), 1.98 (2H, m, CH$_2$-cyclopentyl), 1.64 (2H, m, CH$_2$-cyclopentyl), 1.55 (2H, m, CH$_2$-cyclopentyl); $^{13}$C NMR (d$_4$-CH$_3$OH): δ176.83 (1C, C=O ester), 166.20 (1C, C4-uridine), 152.62, 152.48, 152.39 (1C, C2-uridine), 143.00, 142.88 (1C, C6-uridine), 137.75, 137.73 (1C, C-phenyl), 131.22 (2C, CH-phenyl), 129.98 (1C, C-benzyl), 129.73 (2C, CH-phenyl), 129.69 (1C, CH-phenyl), 126.74 (2C, CH-benzyl), 122.00 (1C, Ch-benzyl), 121.98, 121.93 (2C, CH-benzyl), 103.99, 103.96 (1C, C5-uridine), 99.23, 99.20, 99.06 (1C, C4'-uridine), 92.32, 92.13 (1C, C1'-uridine), 74.86 (1C, C3'-uridine), 69.32 (1C, C2'-uridine), 69.25, 68.79, (1C, C5'-uridine), 68.75, 68.62 (2C, CH$_2$-benzyl), 40.35, 40.24 (1C, CH$_2$-cyclopentyl), 40.07, 39.55 (1C, CH$_2$-cyclopentyl), 25.10 (1C, CH$_2$-cyclopentyl), 24.99 (1C, CH$_2$-cyclopentyl).

EXAMPLE 39

1-{[(2R,3S,4R,5R)-2-Azido-5-(2,4-dioxo-3,4-dihydro-2H-pyrimidin-1-yl)-3,4-dihydroxy-tetrahydrofuran-2-ylmethoxy]-phenoxy-phosphorylamino}-cyclopentanecarboxylic acid ethyl ester (II-5)

The title compound was prepared as described in Example 4 utilizing 4'-azido-uridine (13a, 300 mg, 1.052 mmol), tert-BuMgCl (2.10 mL 1M solution in THF, 2.10 mmol) and phenyl-(ethoxy-cyclopentylglycinyl)phosphorochloridate (12aj, 2.10 mL 1 M solution of THF, 2.10 mmol). The crude was purified by column chromatography and eluted with CHCl$_3$/MeOH (95:5) followed by silica gel preparative TLC developed with CHCl$_3$/MeOH (9:1) which afforded II-5 as a white solid (100 mg, 0.1723 mmol, 16%).

$^{31}$P NMR (d$_4$-CH$_3$OH): δ3.85, 3.83; $^1$H NMR (d$_4$-CH$_3$OH): δ7.69 (1H, m, H6-uridine, J=8.1 Hz), 7.38 (2H, m, CH-phenyl), 7.27 (1H, m, CH-phenyl), 7.23 (2H, m, CH-phenyl), 6.18 (1H, m, H1'-uridine), 5.87 (1H, m, H5-uridine, J=8.1 Hz), 4.40 (2H, m, CH$_2$-ethyl) 4.35 (1H, m, H2'-uridine), 4.22 (1H, m, H3'-uridine), 4.17 (2H, m, H5'-uridine), 2.11 (2H, m, CH$_2$-cyclopentyl), 1.97 (2H, m, CH$_2$-cyclopentyl), 1.73 (2H, m, CH$_2$-cyclopentyl), 1.64 (2H, m, CH$_2$-cyclopentyl), 1.25 (3H, m, CH$_3$-ethyl); $^{13}$C NMR (d$_4$-CH$_3$OH): δ177.05 (1C, C=O ester), 166.22 (1C, C4-uridine), 152.63, 152.51, 152.42 (1C, C2-uridine), 143.06, 142.94 (1C, C6-uridine), 131.23 (2C, CH-phenyl), 126.75 (1C, CH-phenyl), 122.05, 121.99, 121.93 (2C, CH-phenyl), 103.94 (1C, C5-uridine), 99.29, 99.24, 99.15, 99.10 (1C, C4'-uridine), 92.23, 92.14 (1C, C1'-uridine), 74.30, 74.24 (1C, C3'-uridine), 69.34 (1C, C2'-uridine), 68.75 (1C, C5'-uridine), 62.95 (1C, C-cyclopentyl), 55.20 (1C, CH$_2$-ethyl), 40.37, 40.25 (1C, CH$_2$-cyclopentyl), 40.12, 39.52, 39.47 (1C, CH$_2$-cyclopentyl), 25.10, (1C, CH$_2$-cyclopentyl), 24.99 (1C, CH$_2$-cyclopentyl), 14.85 (1C, CH$_3$-ethyl).

EXAMPLE 40

1-{[(2R,3S,4R,5R)-2-Azido-5-(2,4-dioxo-3,4-dihydro-2H-pyrimidin-1-yl)-3,4-dihydroxy-tetrahydrofuran-2-ylmethoxy]-phenoxy-phosphorylamino}-cyclopentanecarboxylic acid isopropyl ester (II-7)

The title compound was prepared as described in Example 4 utilizing 4'-azido-uridine (13a, 300 mg, 1.052 mmol), tert-BuMgCl (2.10 mL 1M solution in THF, 2.10 mmol) and phenyl-(ethoxy-cyclopentylglycinyl)phosphorochloridate (12ak, 2.10 mL 1M solution of THF, 2.10 mmol). The crude was purified by column chromatography and eluted with CHCl$_3$/MeOH (95:5) followed by silica gel preparative TLC developed with CHCl$_3$/MeOH (9: 1) which afforded II-7 as a white solid (110 mg, 0.1995 mmol, 12%).

$^{31}$P NMR (d$_4$-CH$_3$OH): δ3.87, 3.83; $^1$H NMR (d$_4$-CH$_3$OH): δ7.69 (1H, m, H6-uridine, J=8.1 Hz), 7.37 (2H, m, CH-phenyl), 7.27 (1H, m, CH-phenyl), 7.24 (2H, m, CH-phenyl), 6.18 (1H, m, H1'-uridine), 5.66 (1H, m, H5-uridine, J=8.1 Hz), 5.01 (1H, m, CH-isopropyl, J=3.4 Hz), 4.40 (1H, m, H2'-uridine), 4.35 (1H, m, H3'-uridine), 4.24 (2H, m, H5'-uridine), 2.10 (2H, m, CH$_2$-cyclopentyl), 2.02 (2H, m, CH$_2$-cyclopentyl), 1.73 (2H, m, CH$_2$-cyclopentyl), 1.67 (2H, m, CH$_2$-cyclopentyl), 1.24 (6H, d, 2 CH$_3$-isopropyl, J=3.4 Hz); $^{13}$C NMR (d$_4$-CH$_3$OH): δ176.58 (1C, C=O ester), 166.20 (1C, C4-uridine), 152.64 (1C, C2-uridine), 152.52, 152.43 (1C, C4-uridine), 143.10, 142.95 (1C, C6-uridine), 131.26 (1C, CH-phenyl), 126.76 (1C, C-phenyl), 122.07, 122.08, 121.95 (1C, C-phenyl), 104.00, 103.95 (1C, C5-uridine), 99.26, 99.17, 99.12 (1C, C4'-uridine), 92.35, 92.15 (1C, C1'-uridine), 74.86 (1C, C3'-uridine), 70.65 (1C, C2'-uridine), 69.37, 69.30, 68.76 (1C, C5'-uridine), 67.31 (1C, C-cyclopentyl), 40.35, 40.24 (1C, CH$_2$-cyclopentyl), 39.51 (1C, CH$_2$-cyclopentyl), 25.19 (1C, CH$_2$-cyclopentyl), 25.10 (1C, CH$_2$-cyclopentyl), 22.35 (2C, 2 CH$_3$-isopropyl).

EXAMPLE 41

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-4-methyl-pentanoic acid ethyl ester (I-5)

step 1—leucine ethyl ester phosphororchloridate (12q)

The title compound was prepared as described in Example 3 utilizing phenyl dichlorophosphate (0.76 mL, 5.1 mmol), L-leucine ethyl ester hydrochloride (14q, 1.000 g, 5.1 mmol), dry TEA (1.1 mL, 7.6 mmol) and dry DCM (20 mL). The phosphorochloridate 12q was obtained as a yellow oil (1.58 g, yield 93%).

$^{31}$P NMR (CDCl$_3$): δ9.50, 9.72.

step 2—Azido-uridine 5'-O-[phenyl(ethoxy-L-leucinyl) phosphate (I-5)

The title compound was prepared as described in Example 4 utilizing 4'-azido-uridine (13a, 200 mg, 0.7 mmol), tert-BuMgCl (1.4 mL 1M solution in THF, 1.4 mmol), 12q (2.5 mL of a 0.27/g/mL THF solution, 2.1 mmol) and dry THF (10 mL). The crude was purified by two column chromatographies eluting with CHCl$_3$/MeOH (90:10) followed by a preparative TLC developed with CHCl₃/MeOH (85:15) which afforded I-5 as a clear, colorless oil, which solidified to a white foam (0.01 g, yield 35%).

$^{31}$P NMR (CD₄OD): δ4.22, 4.25; $^1$H NMR (CD₄OD): δ8.32 (1H, d, H6), 6.9-7.2(5H, m, Ar—H), 6.27 (1H, dd, H1'), 5.68 (1H, dd, H5), 4.3-4.5 (2H, m, H2', H3'), 4.06 (2H, q, CH₃—CH₂), 3.45 (1H, t, NH—CH—CO₂Et)), 1.9 (3H, m, CH₂—CH(CH₃)₂), 1.24 (3H, t, CH₃—CH₂) 0.97-1.00 (6H, m, CH₂—CH(CH₃)₂); $^{13}$C NMR (CD₄OD): δ173.2, 165.8, 156.7, 153.2, 142.1, 130.0, 128.7, 121.3, 118.1, 111.1, 87.2, 82.2, 63,2, 58.3, 43.2, 42.8, 34.7, 25.8, 23.2, 22.9, 22.1, 11.1.

EXAMPLE 42

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-4-methyl-pentanoic acid ethyl ester (I-27)

The title compound was prepared as described in Example 4 utilizing 4'-azido-cytidine (13b, 400 mg, 1.32 mmol), tert-BuMgCl (3.3 mL 1M solution in THF, 3.3 mmol), 12q (1.05 g mL, 3.31 mmol) and dry THF (10 mL). The crude was purified by two column chromatographies eluting with CHCl₃/MeOH (90:10) followed by a preparative TLC developed with CHCl₃/MeOH (85:15) which afforded I-27 as a clear, colorless oil, which solidified to a white foam (0.01 g, yield 35%).

$^{31}$P NMR (CD₄OD): δ3.22, 3.53; $^1$H NMR (CD₄OD): δ8.10 (1H, d, H6), 6.9-7.2 (5H, m, Ar—H), 6.24 (1H, dd, H1'), 5.85 (1H, dd, H5), 4.2-4.3 (2H, m, H2', H3'), 3.96 (2H, q, CH₃—CH₂), 3.74 (1H, t, NH—CH—CO₂Et)), 1.6-1.8 (3H, m, CH₂—CH(CH₃)₂), 1.43 (3H, t, CH₃—CH₂) 0.96-1.00 (6H, m, CH₂—CH(CH₃)₂); $^{13}$CNMR (CD₄OD); δ168, 158, 143, 131.3, 126.7, 121.7, 121.6, 98.9, 97.2, 94.0, 74.8, 73.9, 62.7, 54.9, 31.1, 26.0, 23.5, 22.3, 14.8.

EXAMPLE 43

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-4-methyl-pentanoic acid isopropyl ester (I-57)

The title compound was prepared as described in Example 4 utilizing 4'-azido-cytidine (13b, 400 mg, 1.32 mmol), tert-BuMgCl (3.3 mL 1M solution in THF, 3.3 mmol), 12r (1.05 g mL, 3.31 mmol) and dry THF (10 mL). The crude was purified by two column chromatographies eluting with CHCl₃/MeOH (85:15) followed by a preparative TLC developed with CHCl₃/MeOH (90:10) which afforded I-57 as a white solid (0.024 g, yield 3%).

$^{31}$P NMR (CD₄OD): δ4.35, 4.51; $^1$H NMR (CD₄OD): δ8.18 (1H, d, H6), 6.72-7.05 (5H, m, Ar—H), 6.32 (1H, dd, H1'), 5.76 (1H, dd, H5), 4.15-4.36 (2H, m, H2', H3'), 4.29 (1H, m, O—CH—(CH₃)₂), 3.56 (1H, t, NH—CH—CO₂Et)), 1.79 (2H, m, CH₂—CH(CH₃)₂), 1.35-1.48 (6H, m, O—CH—(CH₃)₂),) 0.95-1.1 (6H, m, CH₂—CH(CH₃)₂).

EXAMPLE 44

{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-acetic acid benzyl ester (I-58)

The title compound was prepared as described in Example 4 utilizing 4'-azido-uridine (13a, 400 mg, 1.32 mmol), tert-BuMgCl (3.3 mL 1M solution in THF, 3.3 mmol), 12r (1.26 g mL, 3.33 mmol) and dry THF (10 mL). The crude was purified by column chromatography eluting with CHCl₃/MeOH (90:10) followed by a three preparative TLC chromatographies developed with CHCl₃/MeOH (90:10) which afforded I-58 as a white solid (0.06 g, yield 8%).

$^{31}$P NMR (CD₄OD): δ4.11, 4.34; $^1$H NMR (CD₄OD): δ$_H$ 8.42 (1H, d, H6), 6.72-7.05 (5H, m, Ar—H), 6.32 (1H, dd, H1'), 5.76 (1H, dd, H5), 4.15-4.36 (2H, m, H2', H3'), 4.29 (1H, m, O—CH—(CH₃)₂), 3.56 (1H, t, NH—CH—CO₂Et)), 1.79 (2H, m, CH₂—CH(CH₃)₂), 1.35-1.48 (6H, m, O—CH—(CH₃)₂),) 0.95-1.1 (6H, m, CH₂—Ch(CH₃)₂);

EXAMPLE 45

(S)-2-{[(2R,3S,4R, 5R)-5-(4-Amino-2-oxo-2H-pyrimidin- 1-yl)-2-azido-3,4-dihydroxy-tetrahydro-furan-2-ylmethoxy]-phenoxy-phosphorylamino}-4-methyl-pentanoic acid benzyl ester (I-19)

step 1—leucine benzyl ester phosphororchloridate

The title compound was prepared as described in Example B utilizing phenyl dichlorophosphate (11a, 0.55 mL, 3.7 mmol), L-leucine benzyl ester toluenesulfonate (14s 1.01 g, 3.7 mmol), dry TEA (1.0 mL, 7.4 mmol) and dry DCM (20 mL). The phosphorochloridate 12s was obtained as a yellow oil (1.50 g, yield 91%).

$^{31}$P NMR (CDCl₃): δ9.36, 9.60.

step 2—Azido-cytidine 5'-O-[phenyl(benzyloxy-L-leucinyl) phosphate (I-19)

The title compound was prepared as described in Example 4 utilizing 4'-azido-cytidine (13b, 400 mg, 1.32 mmol), tert-BuMgCl (3.3 mL 1M solution in THF, 3.3 mmol), 12s (1.41 g, 3.3 mmol) and dry THF (10 mL). The crude was purified by two column chromatographies eluting with CHCl₃/MeOH (90:10) followed by three preparative TLC chromatographies developed with CHCl₃/MeOH (85:15) which afforded I-19 as a white solid (0.04 g, yield 35%).

$^{31}$P NMR (CD₄OD): δ4.66, 5.00; $^1$H NMR (CD₄OD): δ7.82 (5H, m, Ar—H, 7.35 (1H, s, H6) 7.28 (5H, m, Ar—H), 6.31 (1H, dd, H1'), 5.79 (1H, dd, H5), 5.19 (2H, s, CH₂-Ph), 4.1-4.3 (2H, m, H2', H3'), 4.1 (1H, t, NH—CH—CO₂Et)), 3.91 (2H, q, CH₃—CH₂), 1.5-1.7 (3H, m,CH₂—CH(CH₃)₂), 0.98 (6H, m, CH₂—CH(CH₃)₂) 171.8, 154.5, 131.33, 131.27, 130.72, 130.42, 129.8, 126.9, 126.8, 124.8, 121.9, 121.8, 121.7, 121.63, 121.57, 26.0, 25.8, 23.6, 23.5, 22.3, 21.9, 14.9, 14.86, 9.6.

EXAMPLE 46

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-3-methyl-butyric acid benzyl ester (I-36)

step 1—valine benzyl ester phosphororchloridate (12aq)

The title compound was prepared as described in Example 3 utilizing phenyl dichlorophosphate (11a, 1.22 mL, 8.2 mmol), L-valine benzyl ester hydrochloride (2.000 g, 8.2 mmol), dry TEA (2.3 mL, 16.4 mmol) and dry DCM (20 mL). The phosphorochloridate 12aq was obtained as a yellow oil (2.97 g, yield 95%).

$^{31}$P NMR (CDCl₃): δ10.30, 10.87 step 2—The title compound was prepared as described in Example 4 utilizing 4'-azido-cytidine (13b, 400 mg, 1.32 mmol), tert-BuMgCl (3.3 mL 1M solution in THF, 3.3 mmol), 12aq (1.26 g, 3.3 mmol) and dry THF (10 mL). The crude was purified by column chromatography eluting with CHCl₃/MeOH (90:10) followed by a three preparative TLC chromatographies developed with CHCl₃/MeOH (85:15) which afforded I-36 as a white solid (0.08 g, yield 10%).

$^{31}$P NMR (CD₄OD): δ5.36, 5.66; $^1$H NMR (CD₄OD): 68.12 (1 H, s, H6), 7.31 (5H, m, Ar—H), 6.24 (1H, m, H1'), 5.89 (1H, m, H5), 5.21 (2H, s, CH₂-Ph), 4.3-4.4 (2H, m, H2', H3'), 3.52 (CH13 CH(CH₃)₂), 2.10 (1H, m, —CH(CH₃)₂), 0.7-1.0 (m, 6H, —CH(CH₃)₂),).

EXAMPLE 47

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-3-methyl-butyric acid benzyl ester (I-46)

The title compound was prepared as described in Example 4 Cl utilizing 4'-azido-uridine (13a, 200 mg, 0.70 mmol), tert-BuMgCl (1.8 mL 1M solution in THF, 1.8 mmol), 12aq (0.669 g, 1.75 mmol) and dry THF (10 mL). The crude was purified twice by column chromatography eluting with CHCl₃/MeOH (90:10) followed by a preparative TLC chromatography developed with CHCl₃/MeOH (88:12) which afforded I-46 as a white solid (0.055 g, yield 15%).

$^{31}$P NMR (CD₄OD): δ5.21, 5.40; $^1$H NMR (CD₄OD): 68.20 (1H, s, H6), 7.3-7.4 (5H, m, Ar—H), 7.1-7.35 (5H, m, Ar—H), 6.10 (1H, m, H1'), 5.81 (1H, m, H5), 5.27 (2H, s, CH₂-Ph), 4.1-4.4 (2H, m, H2', H3'), 3.62 (CH—CH(CH₃)₂), 2.1-2.2 (1H, m, —CH(CH₃)₂), 0.7-1.0 (m, 6H, —CH(CH₃)₂),).

EXAMPLE 48

(2S,3S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-3-methyl-pentanoic acid ethyl ester (I-11)

step 1—L-isoleucine ethyl ester hydrochloride salt

L-isoleucine ethyl ester hydrochloride salt was prepared by the procedure in Example 1(B) utilizing L-isoleucine (5.0 g, 38.1 mmol), thionyl chloride (8.3 mL, 11.44 mmol) and EtOH (33.54 mL, 57.15 mmol). The ethyl ester 14t was obtained as a colorless oil (2.5 g, 14.91 mmol, 39%).

$^1$H NMR (CDCl₃): δ8.71 (3H, s, NH₃-amino acid ester), 4.21 (2H, m, CH₂-ethyl), 3.97 (1H, m, CHα), 2.15 (1H, m, CH-lateral chain), 1.48 (2H, m, CH₂-lateral chain) 1.25 (3H, s, CH₃-ethyl), 1.04 (3H, s, CH₃-lateral chain), 0.90 (3H, s, CH₃-lateral chain).

step 2—phenyl-(ethoxy-L-isoleucinyl)phosphorochloridate (12t)

The title compound was prepared as described in Example 3 utilizing phenyl dichlorophosphate (11a, 1.00 mL, 6.76 mmol), 14t (1.4 g, 6.76 mmol), dry TEA (1.88 mL, 13.52 mmol) and dry DCM (15 mL). The phosphorochloridate 12t was obtained as a clear white solid (1.6 g, 4.8 mmol, 71%).

$^{31}$P NMR (CDCl₃): δ10.64, 10.01; $^1$H NMR (CDCl₃): δ7.26 (1H, m, CH-phenyl), 7.19 (2H, m, CH-phenyl), 7.16 (2H, m, CH-phenyl), 7.28 (1H, m, CH-phenyl), 4.76 (1H, m, NH), 4.15 (2H, m, CH₂-ethyl, J=7.08 Hz), 3.89 (1H, m, CHα), 1.82 (1H, m, CH-lateral chain), 1.43 (2H, m, CH₂-lateral chain), 1.16 (3H, m, CH₃-ethyl), 0.87-0.86 (6H, 2 CH₃-lateral chain).

step 3—azido-cytidine 5'-O-[phenyl(ethoxy-L-iso-leucinyl) phosphate (I-11)

The title compound was prepared as described in Example 4 utilizing 4'-azido-cytidine (13b, 300 mg, 0.986 mmol), tert-BuMgCl (2.46 mL 1M solution in THF, 2.46 mmol) and 12t (2.46 mL 1M solution of THF, 2.46 mmol). The crude was purified by column chromatography and eluted with CHCl₃/MeOH (95:5) followed by a preparative TLC developed with CHCl₃/MeOH (85:15) which afforded I-11 as a white solid (20 mg, 0.034 mmol, 3%).

$^{31}$P NMR (d₄-CH₃OH): δ5.55, 5.30; $^1$H NMR (d₄-CH₃OH): δ7.62 (1H, m, H6-cytidine, J=7.7 Hz), 7.34 (2H, m, CH-phenyl), 7.23 (1H, m, CH-phenyl), 7.17 (2H, m, CH-phenyl), 6.14 (1H, m, H1'-cytidine, J=9.51 Hz), 5.83 (1H, m, H5-cytidine, J=7.7 Hz), 4.31 (2H, m, CH₂-ethyl), 4.19 (1H, m, H2'-cytidine), 4.13 (1H, m, H3'-cytidine), 4.08 (2H, m, H5'-cytidine), 3.71 (1H, m, CHα), 1.74 (1H, m, CH-lateral chain), 1.45 (2H, m, CH₂-lateral chain) 1.15 (3H, m, CH₃-ethyl), 0.85-0.82 (6H, m, 2 CH₃-lateral chain).

EXAMPLE 49

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid methyl ester (I-1)

The title compound was prepared according to Example 7 utilizing 4'-azido-2',3'-isopropylidenecytidine-5'-[phenyl-(methoxy-L-alaninyl)]-phosphate (IV-4, 140 mg, 0.248 mmol) dissolved in a 60/40 acetic acid/water mixture, and heated to 90° C. Removal of the solvents in vacuo and purification by preparative TLC purification developed with DCM/MeOH (9:1) afforded I-1 as a white solid (37 mg, 22%).

$^{31}$P NMR (121.5 MHz, d₄-MeOH): δ4.71, 4.54; $^{H NMR}$ (300 MHz, d₄-MeOH): δ7.71-7.63 (1H, m, H-6), 7.39-7.35 (2H, m, Ph-CH), 7.28-7.20 (3H, m, Ph-CH), 6.20-6.14 (1H, dd, J=4.5 and 14.5 Hz, H-1'), 5.94-5.87 (1H, m, H-5), 4.40-4.19 (4H, m, H-2', H-3' and H-5'), 4.02-3.97 (1H, m, Ala-CH), 3.71 (3H, m, —OCH₃), 1.37-1.33 (3H, m, Ala-CH₃); $^{13}$C NMR (75.5 MHz, d₄-MeOH): δ175.09, 175.04, 174.81, 174.75 (C=O), 167.17 (C-2), 157.72 (C-4), 151.53, 151.44, 151.43 (Ph-C), 142.62, 142.48 (C-6), 130.41 (Ar—C), 125.92 (Ar—C), 120.94, 120.88 (Ar—C), 98.27, 98.16, 98.14, 98.03 (C-5), 96.46 (C-4'), 93.36, 92.94 (C-1'), 74.00, 73.83 (C-3'), 72.99 (C-2'), 68.31, 68.24, 68.19, 68.12 (C-5'), 52.40 (OCH₃), 51.16, 51.01 (Ala-CH), 20.02, 19.93, 19.79, 19.69 (Ala-CH₃)

EXAMPLE 50

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid methyl ester (I-54)

The title compound was prepared as described in Example 4 utilizing 4'-azido-uridine (13a, 200 mg, 0.701 mmol), tert-BuMgCl (1.4 mL 1M solution in THF, 1.4 mmol), dry THF (10 mL) and 12c (1.4 mL 1M solution of THF, 1.4 mmol). The crude was purified by column chromatography and eluted with a CHCl₃/MeOH gradient (90:10 to 80:20) followed by a preparative TLC developed with CHCl₃/MeOH (90:10) which afforded I-54 as a white solid (29 mg, yield 10%).

$^{31}$P NMR (121.5 MHz, d₄-MeOH): δ4.78, 4.57; $^1$H NMR (300 MHz, d₄-MeOH): δ7.68-7.61 (1H, m, H-6), 7.42-7.36 (2H, m, Ph-CH), 7.28-7.20 (3H, m, Ph-CH), 6.18-6.11 (1H, m, H-1'), 5.75-5.66 (1H, m, H-5), 4.42-4.35 (2H, m, H-2' and H-3'), 4.23-4.16 (2H, m, H-5'), 4.06-3.95 (1H, m, Ala-CH), 3.70 (3H, m, —OCH₃), 1.38-1.33 (3H, m, Ala-CH₃); $^{31}$C NMR (75.5 MHz, d₄-MeOH): δ176.01, 175.96, 175.70 (C=O), 166.25 (C-2), 152.66, 152.59, 152.40, 152.31 (Ph-C), 143.12 (C-6), 131.32 (Ar—C), 126.82 (Ar—C), 121.80, 121.73 (Ar—C), 104.09, 104.01 (C-5), 99.19, 99.05, 98.92 (C-4'), 92.83, 92.44 (C-1'), 74.00, 73.84 (C-3'), 74.20, 74.15, 74.04 (C-2'), 69.28, 69.21, 69.13, 69.06 (C-5'), 53.30 (—OCH₃), 52.03, 51.87 (Ala-CH), 20.91, 20.83, 20.68, 20.58 (Ala-CH₃).

EXAMPLE 51

(R)-2-{[(2R,3S,4R,5R)-5-(4-Amino-2-oxo-2H-pyrimidin-1-yl)-2-azido-3,4-dihydroxy-tetrahydro=furan-2-ylmethoxy]-phenoxy-phosphorylamino}-propionic acid benzyl ester (I-32)

step 1—phenyl-(benzyloxy-D-alaninyl)phosphorochloridate (12m)

The title compound was prepared as described in Example 3 utilizing phenyl dichlorophosphate (11a, 0.637 mL, 4.27 mmol), D-alanine benzyl ester sulfonate salt (14m, 0.9 g, 4.27 mmol), dry TEA (1.19 mL, 8.54 mmol) and dry DCM (15 mL). The phosphorochloridate 12m was obtained as a clear oil (1.15 g, 3.25 mmol, 76%).

$^{31}$P NMR (CDCl₃): δ9.29, 9.05; $^{1}$H NMR (CDCl₃): δ7.41 (6H, m, 5 CH-phenyl, 1 CH-benzyl), 7.32-7.30 (4H, m, CH-benzyl), 5.26 (2H, d, CH₂-benzyl), 4.66 (1H, m, NH), 4.34 (1H, m, CHα), 1.57 (3H, m, CH₃-alanine).

step 2—azido-cytidine 5'-O-[phenyl(benzyloxy-D-alaninyl) phosphate

The title compound was prepared as described in Example 4 utilizing 4'-azido-cytidine (13b, 300 mg, 0.986 mmol), tert-BuMgCl (2.46 mL 1M solution in THF, 2.46 mmol) and 12m (2.46 mL 1M solution of THF, 2.46 mmol). The crude was purified by column chromatography and eluted with CHCl₃/MeOH (95:5) followed by a preparative TLC developed with CHCl₃/MeOH (85:15) which afforded I-31 as a white solid (20 mg, 0.033 mmol, 3%).

$^{31}$P NMR (d₄-CH₃OH): δ4.80, 4.26; $^{1}$H NMR (d₄-CH₃OH): δ7.63 (1H, m, H6-cytidine, J=7.6 Hz), 7.35 (6H, m, 5 CH-phenyl, 1 CH-benzyl), 7.23 (4H, m, CH-benzyl), 6.15 (1H, m, H1'-cytidine), 5.89 (1H, m, H5-cytidine, J=7.6 Hz), 5.16 (2H, s, CH₂-benzyl), 4.35 (2H, m, H5'-cytidine), 4.26 (1H, m, H2'-cytidine), 4.23 (1H, m, H3'-cytidine), 4.16 (1H, m, CHα), 1.34 (3H, m, CH₃-alanine).

EXAMPLE 52

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid ethyl ester (I-24)

The title compound was prepared as described in Example 4 utilizing 4'-azido-uridine (13a, 200 mg, 0.70 mmol), tert-BuMgCl (1.74 mL 1M solution in THF, 1.74 mmol) and 12d (1.74 mL 1 M solution of THF, 1.74 mmol). The crude was purified by column chromatography and eluted with a CHCl₃/MeOH gradient (90:10 to 80:20) followed by a preparative TLC developed with CHCl₃/MeOH (90:10) which afforded I-24 as a white solid (17 mg, yield 5%).

$^{31}$NMR (121.5 MHz, d₄-MeOH): δ4.84, 4.61; $^{1}$H NMR (300 MHz, d₄-MeOH): δ7.69-7.62 (1H, m, H-6), 7.42-7.36 (2H, m, Ph-CH), 7.29-7.20 (3H, m, Ph-CH), 6.19-6.11 (1H, m, H-1'), 5.75-5.66 (1H, m, H-5), 4.82 (1H, s, H-2'), 4.25 (1H, m, H-3'), 4.17-4.12 (2H, m, H-5'), 4.00-3.92 (1H, m, Ala-CH), 1.38-1.32 (3H, m, Ala-CH₃), 1.29-1.23 (3H, m, CH₂CH₃).

EXAMPLE 53

(R)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid tert-butyl ester (I-53)

step 1—phenyl-(tert-butoxy-D-alaninyl)phosphorochloridate

The title compound was prepared as described in Example 3 utilizing phenyl dichlorophosphate (11a, 1.640 mL, 11.00 mmol), D-alanine tert-butyl ester hydrochloride salt (14j, 2.00 g, 11.00 mmol), dry TEA (1.61 mL, 22.00 mmol) and dry DCM (15 mL). The phosphorochloridate 12j was obtained as a clear oil (1.43 g, 4.46 mmol, 41%).

$^{31}$P NMR (CDCl₃): δ9.48, 9.30; $^{1}$H NMR (CDCl₃): δ7.37-7.12 (5H, m, 5 CH-phenyl), 4.84 (1H, m, NH), 4.80 (1H, m, CHα), 1.93 (9H, s, CH₃-tert-butyl), 1.39 (3H, d, CH₃-alanine, J=4.2 Hz).

step 2—azido-cytidine 5'-O-[phenyl(tert-butoxy-D-alaninyl) phosphate

The title compound was prepared as described in Example 4 utilizing 4'-azido-cytidine (13b, 250 mg, 0.821 mmol), tert-BuMgCl (2.05 mL 1M solution in THF, 2.054 mmol) and 12j (2.05 mL 1M solution of THF, 2.054 mmol). The crude was purified by column chromatography and eluted with CHCl₃/MeOH (95:5) followed by a preparative TLC developed with CHCl₃/MeOH (85:15) which afforded I-53 as a white solid (3.5 mg, 0.033 mmol, 1%).

$^{31}$P NMR (d₄-CH₃OH): δ4.91, 4.45; $^{1}$H NMR (d₄-CH₃OH): δ7.67 (1H, m, H6-cytidine, J=7.5 Hz), 7.45 (5H, m, CH-phenyl), 6.17 (1H, m, H1'-cytidine), 5.92 (1H, m, H5-cytidine, J=7.5 Hz), 4.40-4.18 (2H, m, H2'-cytidine, H3'-cytidine, H5'-cytidine), 3.85 (1H, m, CHα), 1.45 (9, s, CH₃-tert-butyl), 1.37 (3H, m, CH₃-alanine); MS(ES) m/e: 590 (MNa⁺, 100%); Accurate mass: C₂₂H₃₀N₇O₉NaP required 590.1761, found 590.1740.

EXAMPLE 54

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid benzyl ester (I-13)

The title compound was prepared as described in Example 4 utilizing 4'-azido-uridine (13a, 200 mg, 0.701 mmol), tert-BuMgCl (1.75 mL 1M solution in THF, 1.75 mmol) and 12an (1.75 mL 1M solution of THF, 1.75 mmol). The crude was purified by column chromatography and eluted with a CHCl₃/MeOH gradient (90:10 to 80:20) followed by a preparative TLC developed with CHCl₃/MeOH (90:10) which afforded I-13 as a white solid (29 mg, yield 7%).

$^{31}$P NMR (121.5 MHz, d₄-MeOH): δ4.80, 4.54; H NMR (300 MHz, d₄-MeOH): δ7.65-7.58 (1H, m, H-6), 7.36-7.34 (7H, m, Ph-CH), 7.26-7.19 (3H, m, Ph-CH), 6.17-6.13 (1H, m, H-1'), 5.72-5.64 (1H, m, H-5), 5.16 (2H, s, Bn-CH₂), 4.35 (2H, m, H-2' and H-3'), 4.17-4.12 (2H, m, H-5'), 4.05 (1H, m, Ala-CH), 1.41-1.34 (3H, m, Ala-CH₃); $^{13}$C NMR (75.5 MHz, d₄-MeOH): δ176.98, 174.97, 174.89 (C=O), 166.34 (C-4), 152.66, 152.31 (Ph-C), 143.04, 142.82 (C-6), 137.77, 173.58 (Ar—C), 131.30 (Ar—C), 130.51, 130.00, 129.92, 129.70 (Ar—C), 126.77 (Ar—C), 124.25 (Ar—C), 122.02 (Ar—C), 121.96, 1221.82, 121.78, 121.72 (Ar—C), 104.10, 104.00 (C-5), 99.04, 98.91 (C-4'), 92.80, 92.33 (C-1'), 74.24, 74.14, 74.05 (C-2' and C-3'), 69.28 (C-5'), 68.46, 68.06 (Bn-CH$_2$), 52.20, 52.02 (Ala-CH), 21.89, 21.82, 20.87, 20.78 (Ala-CH$_3$).

EXAMPLE 55

(R)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid benzyl ester (I-40)

The title compound was prepared as described in Example 4 utilizing 4'-azido-uridine (13a, 200 mg, 0.701 mmol), tert-BuMgCl (1.4 mL 1M solution in THF, 1.402 mmol) and phenyl (benzyloxy-D-alaninyl)phosphorochloridate (12m, 2.10 mL of solution 1M in THF, 2.10 mmol). The crude was purified by column chromatography and eluted with CHCl$_3$/MeOH (95:5) followed by a preparative TLC developed with CHCl$_3$/MeOH (9:1) which afforded I-40 as a white solid (100 mg, 0.1723 mmol, 16%).

$^{31}$P NMR (d$_4$-CH$_3$OH): δ4.89, 4.29; $^1$H NMR (d$_4$-CH$_3$OH): δ7.61 (1H, m, H6-uridine), 7.36 (7H, m, CH-phenyl), 7.25 (3H, m, CH-phenyl), 6.15 (1H, m, H1-uridine), 5.68 (1H, m, H5-uridine), 5.17 (2H, s, CH$_2$-benzyl), 4.38 (1H, m, H3'-cytidine), 4.32 (1H, m, H2'-cytidine), 4.23 (2H, m, H5'-cytidine), 4.05 (1H, m, CHα), 1.36 (3H, m, CH$_3$-alanine); $^{13}$C NMR (d$_4$-CH$_{30}$H): δ175.34, 175.29, 175.07, 175.01 (1C, C=O ester), 166.22 (1C, C4-uridine), 152.65, 152.56, 152.40, 152.36, 152.31, 152.27 (1C, C2-uridine), 142.94, 142.86 (1C, C6-uridine), 137.60, 137.54 (1C, C-phenyl), 131.31 (2C, CH-phenyl), 130.00 (2C, CH-phenyl), 129.79, 129.76, 129.72 (2C, CH-phenyl), 126.79 (1C, CH-phenyl), 121.83, 121.77, 121.71, 121.64 (2C, CH-phenyl), 104.03, 103.99 (1C, C5-uridine), 99.11, 98.98 (1C, C4'-uridine), 92.69, 92.43 (1C, C1'-uridine), 74.22, 74.16 (1C, C3'-uridine), 74.13, 73.93 (1C, C2'-uridine), 69.28, 69.21 (1C, CH$_2$-benzyl), 68.71, 68.65, 68.54, 68.48 (1C, C5'-uridine), 52.17, 51.92 (1C, CHα), 20.80, 20.70, 20.59 (1C, CH$_3$-lateral chain): MS (ES) m/e: 625.1 (MNa$^+$, 100%); Accurate mass: C$_{25}$H$_{27}$N$_6$O$_{10}$NaP required 625.1424, found 625.1424.

EXAMPLE 56

(R)-2-{[(2R,3S,4R,5R)-2-Azido-5-(2,4-dioxo-3,4-dihydro-2H-pyrimidin-1-yl)-3,4=dihydroxy-tetrahydro-furan-2-ylmethoxy]-phenoxy-phosphorylamino}-propionic acid isopropyl ester (I-60)

step 1—D-alanine iso-propyl ester hydrochloride salt

D-alanine iso-propyl ester hydrochloride salt was prepared by the procedure in Example 1(B) utilizing D-alanine (7.0 g, 78.6 mmol), thionyl chloride (11.42 mL, 157.2 mmol) and IPA (90 mL, 1.178 mmol). The iso-propyl ester 14ap was obtained as a white solid (8.3 g, 49.70 mmol, 64%).

$^1$H NMR (d$_6$-DMSO): δ8.70 (3H, s, NH$_3^+$-amino acid ester), 4.87 (1H, m, CH-iso-propyl, J=6.3 Hz), 1.54 (3H, m, CH$_3$-alanine), 1.25 (6H, d, CH$_3$ iso-propyl, J=6.3 Hz).

step 2—phenyl-(isopropoxy-D-alaninyl)phosphorochloridate

The title compound was prepared as described in Example 3 utilizing phenyl dichlorophosphate (11a, 1.79 mL, 12.0 mmol), 14ap (2.0 g, 12.0 mmol), dry TEA (3.34 mL, 24.0 mmol) and dry DCM (25 mL). The phosphorochloridate 12ap was obtained as a clear yellow oil (0.77 g, 2.52 mmol, 21%).

$^{31}$P NMR (CDCl$_3$): δ9.41, 9.09; $^1$H NMR (CDCl$_3$): δ7.43 (2H, m, CH-phenyl), 7.25 (1H, m, CH-phenyl), 6.80 (2H, m, CH-phenyl), 5.00 (1H, m, NH), 4.97 (1H, m, CH-isopropyl), 1.48 (3H, m, CH$_3$-alanine), 1.27 (6H, m, CH$_3$-isopropyl).

step 3—azido-uridine 5'-O-[phenyl(isopropoxy-cyclopentylglycinyl)]phosphate (I-60)

The title compound was prepared as described in Example 4 utilizing 4'-azido-uridine (13a, 200 mg, 0.701 mmol), tert-BuMgCl (1.0 mL 1M solution in THF, 1.052 mmol) and 12ap (1.0 mL of solution 1M in THF, 1.052 mmol). The crude was purified by column chromatography and eluted with CHCl$_3$/MeOH (95:5) followed by a preparative TLC developed with CHCl$_3$/MeOH (9:1) which afforded I-60 as a white solid (19.7 mg, 0.0355 mmol, 4%).

$^{31}$P NMR (d$_4$-CH$_3$OH): δ4.97, 4.41; $^1$H NMR (d$_4$-CH$_3$OH): δ7.71 (1H, m, H6-uridine), 7.30 (2H, m, CH-phenyl), 7.27 (1H, m, CH-phenyl), 7.20 (2H, m, CH-phenyl), 6.18 (1H, m, H1'-uridine), 5.66 (1H, m, H5-uridine), 4.98 (1H, m, CH-isopropyl, J=3.4 Hz), 4.42 (1H, m, H2'-uridine), 4.37 (1H, m, H3'-uridine), 4.24 (2H, m, H5'-uridine), 1.45 (3H, m, CH$_3$-alanine), 1.24 (6H, d, 2 CH$_3$-isopropyl, J=3.4 Hz).

EXAMPLE 57

(S)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid isopropyl ester (I-14)

The title compound was prepared as described in Example 4 utilizing 4'-azido-uridine (13a, 100 mg, 0.35 mmol), tert-BuMgCl (0.87 mL 1M solution in THF, 0.87 mmol) and 12e (0.87 1M solution of THF, 0.87 mmol). The crude was purified by column chromatography and eluted with a CHCl$_3$/MeOH gradient (90:10 to 80:20) followed by a preparative TLC developed with CHCl$_3$/MeOH (90:10) which afforded I-14 as a white solid (33.6 mg, yield 17%).

$^{31}$P NMR (121.5 MHz, d$_4$-MeOH): δ4.87, 4.64; $^1$H NMR (300 MHz, d$_4$-MeOH): δ7.64 (1H, m, H-6), 7.39 (2H, m, Ph-CH), 7.29 (3H, m, Ph-CH), 6.15 (1H, m, H-1'), 5.66 (1H, m, H-5), 4.97 (1H, s, H-2'), 4.37 (2H, m, iso-Pr—CH and H-3'), 4.17-4.12 (2H, m, H-5'), 3.99-3.92 (1H, m, Ala-CH), 1.34 (3H, m, Ala-CH$_3$), 1.24 (6H, m, iso-Pr—CH$_3$).

EXAMPLE 58

(R)-2-{[(2R,3S,4R,5R)-2-Azido-5-(2,4-dioxo-3,4-dihydro-2H-pyrimidin- 1yl)-3,4-dihydroxy-tetrahydro-furan-2-ylmethoxy]-phenoxy-phosphorylamino}-propionic acid sec-butyl ester (I-62)

step 1—D-alanine 2-butyl ester p-toluenesulfonate salt

D-alanine 2-butyl ester p-toluenesulfonate salt was prepared by the procedure in Example 1(C) from D-alanine (5.0 g, 56.1 mmol), pTsOH monohydrate (11.747 g, 61.7 mmol), 2-butanol (26 mL, 280 mmol)) and toluene (50 mL). The product 14k was isolated as white solid (12.44 g, 39.2 mmol, 70%)

$^1$H NMR (d$_4$-CH$_3$OH): δ8.49 (3H, s, NH$_3^+$-amino acid ester), 1.85 (2H, d, tosylate, J=8.0 Hz), 7.15 (2H, d, CH-tosylate, J=8.0 Hz), 4.20-4.00 (2H, CHα, CH-2-butyl), 2.42 (3H, s, CH$_3$-tosylate), 1.49 (3H, d, CH$_3$-alanine, J=9.0 Hz), 1.24-1.20 (5H, m, CH$_2$-2-butyl, CH$_3$-2-butyl), 0.94 (3H, m, CH$_3$-2-butyl).

step 2—phenyl-(2-butoxy-D-alaninyl)phosphorochloridate

The title compound was prepared as described in Example 3 utilizing phenyl dichlorophosphate (11a, 1.40 mL, 9.45 mmol), 14k (3.0 g, 9.45 mmol), dry TEA (2.63 mL, 18.90 mmol) and dry DCM (15 mL). The phosphorochloridate 12k was obtained as a clear yellow oil (2.70 g, 8.44 mmol, 71.93%).

$^{31}$P NMR (CDCl$_3$): δ9.51, 9.32; $^1$H NMR (CDCl$_3$): δ7.37-7.12 (5H, m, 5 CH-phenyl), 4.96-4.76 (1H, m, NH, CHα), 4.05 (1H, m, CH-2-butyl), 1.41 (3H, d, CH$_3$-alanine), 1.24-1.19 (5H, m, CH$_2$-2-butyl, CH$_3$-2-butyl), 0.92 (3H, m, CH$_3$-2-butyl).

step 3—azido-uridine 5'-O-[phenyl(2-butoxy-D-alaninyl) phosphate (I-62)

The title compound was prepared as described in Example 4 utilizing 4'-azido-uridine (13a 200 mg, 0.701 mmol), tert-BuMgCl (1.4 mL 1M solution in THF, 1.402 mmol) and 12k (1.40 mL of solution 1M in THF, 1.402 mmol). The crude product was purified by column chromatography and eluted with CHCl$_3$/MeOH (85:15) followed by a preparative TLC developed with CHCl$_3$/MeOH (9:1) which afforded I-62 as a white solid (18.2 mg, 0.033 mmol, 5%).

$^{31}$P NMR (d$_4$-CH$_3$OH): δ4.97, 4.96, 4.45, 4.41; $^1$H NMR (d$_4$-CH$_3$OH): δ7.70 (1H, m, H6-cytidine, J=10.0 Hz), 7.42-7.21 (5H, m, CH-phenyl), 6.15 (1H, m, H1'-cytidine), 5.72 (1H, m, H5-cytidine, J=10.0 Hz), 4.40-4.15 (2H, m, H2'-cytidine, H3'-cytidine, H5'-cytidine), 3.91 (1H, m, CHα), 1.61 (3H, d, CH$_3$-alanine), 1.40-1.19 (5H, m, CH$_2$-2-butyl, CH$_3$-2-butyl), 0.91 (3H, m, CH$_3$-2-butyl); $^{13}$C NMR dept (d$_4$-CH$_3$OH): δ143.03, 142.94 (1C, C6-uridine), 131.32 (1C, CH-phenyl), 121.86, 121.79 (2C, CH-phenyl), 121.72, 121.66 (2C, CH-phenyl), 104.05 (1C, C5-cytidine), 92.60-92.43 (1C, C1'-uridine), 75.30, 74.84 (1C, C3'-uridine), 74.27, 74.15, 74.09, 74.04 (1C, C2'-uridine), 69.26 (1C, C5'-uridine), 68.86 (1C, CH-2-butyl), 52.01 (1C, CH-α), 30.20, 30.16 (1C, CH$_2$-2-butyl), 20.53, 20.47 (1C, CH$_3$-lateral chain), 20.18, 20.14 (1C, CH$_3$-2-butyl), 20.05, 19.97 (1C, CH$_3$-2-butyl).

EXAMPLE 59

(R)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-propionic acid dodecyl ester (I-64)

step 1—D-alanine dodecyl ester p-toluene sulfonate salt

D-alanine dodecyl ester p-toluene sulfonate salt (141) was prepared by the procedure in Example 1(C) from D-alanine (2.5 g, 28.0 mmol), TsOH monohydrate (5.87 g, 30.9 mmol), dodecyl alcohol (13.0 g, 280 mmol) and toluene (50 mL). The product was isolated as white solid (7.92 g, 18.48 mmol, 66%)

$^1$H NMR (d$_4$-CH$_3$OH): δ8.45 (3H, s, NH$_3$+-amino acid ester), 7.82 (2H, d, tosylate, J=8.1 Hz), 7.19 (2H, d, CH-tosylate, J=8.1 Hz), 4.16-4.00 (3H, CHα, CH$_2$-dodecyl), 2.40 (3H, s, CH$_3$-tosylate), 1.49 (3H, d, CH$_3$-alanine, J=7.2 Hz), 1.30 (22H, m, CH$_2$-dodecyl), 0.94 (3H, t, CH$_3$-dodecyl, J=6.3 Hz).

step 2—phenyl-(dodecyloxy-D-alaninyl)phosphorochloridate

The title compound was prepared as described in Example 3 utilizing phenyl dichlorophosphate (11a, 0.521 mL, 3.49 mmol), D-alanine dodecyl ester tosylate salt (141, 1.5 g, 3.49 mmol), dry TEA (0.959 mL, 6.88 mmol) and dry DCM (15 mL). The phosphorochloridate 121 was obtained as a clear oil (1.00 g, 2.34 mmol, 67%).

$^{31}$P NMR (CDCl$_3$): δ9.38, 9.15; $^1$H NMR (CDCl$_3$): 7.41-7.19 (5H, m, 5 CH-phenyl), 4.78 (1H, m, NH), 4.25-4.00 (3H, m, CHα, CH$_2$-dodecyl), 1.54 (3H, m, CH$_3$-alanine), 1.28 (22H, m, 11 CH$_2$-dodecyl), 0.91 (3H, t, CH$_3$-dodecyl, J=6.3 Hz).

step 3—azido-cytidine 5'-O-[phenyl(dodecyloxy-D-alaninyl)phosphate

The title compound was prepared as described in Example 4 utilizing 4'-azido-cytidine (13b, 200 mg, 0.657 mmol), tert-BuMgCl (1.64 mL 1M solution in THF, 1.640 mmol) and 121 (1.64 mL 1M solution of THF, 1.64 mmol). The crude was purified by column chromatography and eluted with CHCl$_3$/MeOH (85:15) followed by a preparative TLC developed with CHCl$_3$/MeOH (85:15) which afforded I-64 as a white solid (22.6 mg, 0.033 mmol, 5%).

$^{31}$p NMR (d$_4$-CH$_3$OH): δ4.80, 4.33; $^1$H NMR (d$_4$-CH$_3$OH): δ$_H$ 7.65 (1H, m, H6-cytidine, J=9.0 Hz), 7.42-7.18 (5H, m, 5H, CH-phenyl), 6.18 (1H, m, H1'-cytidine), 5.90 (1H, m, H5-cytidine), 4.40-3.95 (2H, m, H2'-cytidine, H3'-cytidine, H5'-cytidine, CHα, CH$_2$-dodecyl), 1.54 (3H, m, CH$_3$-alanine), 1.30 (22H, m, 11 CH$_2$-dodecyl), 0.92 (3H, t, CH$_3$-dodecyl, J=6.5 Hz).

EXAMPLE 60

(R)-2-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphorylamino}-propionic acid dodecyl ester (I-63)

The title compound was prepared as described in Example 4 utilizing 4'-azido-uridine (13a, 200 mg, 0.701 mmol), tert-BuMgCl (1.40 mL 1M solution in THF, 1.402 mmol) and phenyl (dodecyl-D-alaninyl)phosphorochloridate (121, 1.40 ml of solution 1M in THF, 1.402 mmol). The crude was purified by column chromatography and eluted with CHCl$_3$/MeOH (95:5) followed by a preparative TLC developed with CHCl$_3$/MeOH (85:15) which afforded I-63 as a white solid (18.2 mg, 0.033 mmol, 4%).

$^{31}$P NMR (d$_4$-CH$_3$OH): δ4.92, 4.38; $^1$H NMR (d$_4$-CH$_3$OH): δ7.67 (1H, m, H6-uridine, J=8.7 Hz), 7.42-7.22 (5H, m, 5H, CH-phenyl), 6.15 (1H, m, H1'-cytidine), 5.73 (1H, m, H5-cytidine, J=8.7 Hz), 4.40-3.95 (2H, m, H2'-cytidine, H3'-cytidine, H5'-cytidine, CHα, CH$_2$-dodecyl), 1.64 (3H, m, CH$_3$-alanine), 1.30 (22H, m, 11 CH$_2$-dodecyl), 0.92 (3H, t, CH$_3$-dodecyl).

EXAMPLE 61

(S)-2-{[(2R,3S,4R,5R)-2-Azido-5-(2,4-dioxo-3,4-dihydro-2H-pyrimidin-1-yl)-3,4-dihydroxy-tetrahydro-furan-2-yl methoxy]-phenoxy-phosphorylamino}-4-methylsulfanyl-butyric acid ethyl ester (I-48).

The title compound was prepared as described in Example 4 utilizing 4'-azido-uridine (13a, 200 mg, 0.70 mmol), tert-BuMgCl (1.80 mL 1M solution in THF, 1.8 mmol), phenyl (ethoxy-L-methinonyl)phosphorochloridate (12x, 0.615 g 1.75 mmol) and THF (10 mL). The crude was purified by column chromatography and eluted with CHCl$_3$/MeOH (90:10) followed by a preparative TLC developed with CHCl$_3$/MeOH (90:10) which afforded I-48 as a white solid (0.42 g, 0.07 mmol, 10%).

$^{31}$P NMR (CD$_4$OD): δ4.23, 4.35; $^1$H NMR (CD$_4$OD): δ8.21 (1H, d, H6), 6.7-7.1 (5H, m, Ar—H), 6.02 (1H, dd, H1'), 5.76 (1H, dd, H5), 4.08 (2H, q, O—$\underline{CH_2}$—CH$_3$), 3.6-3.9

(2H, m, H2', H3'), 3.29 (t, NH—C$\underline{H}$—CO$_2$Et)), 2.3-2.4 (4H, m, C$\underline{H_2}$—C$\underline{H_2}$—S—CH$_3$), 1.98 (3H, s, S—C$\underline{H_3}$) 1.28 (3H, t, OC$\underline{H_2}$—C$\underline{H_3}$)

EXAMPLE 62

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-4-methyl-sulfanyl-butyric acid ethyl ester (I-47)

The title compound was prepared as described in Example 4 utilizing 4'-azido-cytidine (13b, 400 mg, 1.32 mmol), tert-BuMgCl (3.3 mL 1M solution in THF, 3.3 mmol), phenyl (ethoxy-L-methinonyl)phosphorochloridate (12x, 1.16 g, 3.3 mmol) and THF (10 mL). The crude was purified by column chromatography and eluted with CHCl$_3$/MeOH (85:15) followed by a preparative TLC developed with CHCl$_3$/MeOH (90:10) which afforded I-47 as a white solid (0.23 g, 0.038 mmol, 3%).

$^{31}$P NMR (CD$_4$OD): δ4.01, 4.27; $^1$H NMR (CD$_4$OD): δ7.96 (1 H, d, H6), 6.5-7.1 (5H, m, Ar—H), 6.23 (1H, dd, H1'), 5.94 (1H, dd, H5), 4.15 (2H, q, O—C$\underline{H_2}$—CH$_3$), 3.7-3.9 (2H, m, H2', H3'), 3.39 (1H, t, NH—C$\underline{H}$—CO$_2$Et)), 2.2-2.45 (4H, m, C$\underline{H_2}$—C$\underline{H_2}$—S—CH$_3$), 2.07 (3H, s, S—C$\underline{H_3}$) 1.21 (3H, t, OC$\underline{H_2}$—C$\underline{H_3}$)

EXAMPLE 63

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphorylamino}-pentanedioic acid diethyl ester (I-83)

step 1—phenyl-(ethoxy-L-ethylaspartyl)phosphorochloridate

The title compound was prepared as described in Example 3 utilizing phenyl dichlorophosphate (11a, 0.670 mL, 4.49 mmol), L-ethylasparatate ethyl ester hydrochloride salt (14y, 1.0 g, 4.49 mmol), dry TEA (1.25 mL, 8.98 mmol) and dry DCM (15 mL). The phosphorochloridate 12y was obtained as a clear oil (1.137 g, 3.143 mmol, 70%).

$^{31}$P NMR (CDCl$_3$): δ9.78, 9.54; $^1$H NMR (CDCl$_3$): δ7.31-7.06 (5H, m, 5 CH-phenyl), 4.86 (1H, m, NH), 4.25-4.00 (5H, m, CHα, CH$_2$-ethyl, CH$_2$-ethyl lateral chain), 2.78 (2H, m, CH$_2$-lateral chain), 1.23 (6H, m, CH$_3$-ethyl, CH$_3$-ethyl lateral chain).

step 2—azido-cytidine 5'-O-[phenyl(ethoxy-L-ethylaspartyl) phosphate

The title compound was prepared as described in Example 4 utilizing 4'-azido-cytidine (13b, 300 mg, 0.986 mmol), tert-BuMgCl (1.97 mL 1M solution in THF, 1.972 mmol) and 12y (1.97 mL 1M solution of THF, 1.972 mmol). The crude was purified by column chromatography and eluted with CHCl$_3$/MeOH (85:15) which afforded I-83 as a white solid (30.15 mg, 0.0493 mmol, 5%).

$^{31}$P NMR (d$_4$-CH$_3$OH): δ4.67, 4.40; $^1$H NMR (d$_4$-CH$_3$OH): δ7.70 (1H, m, H6-cytidine), 7.40-7.16 (5H, m, CH-phenyl), 6.16 (1H, m, H1'-cytidine), 5.85 (1H, m, H5-cytidine), 4.40-4.00 (8H, m, H2'-cytidine, H3'-cytidine, H5'-cytidine, CHα, CH$_2$-ethyl, CH$_2$-ethyl lateral chain), 2.78 (2H, m, CH$_2$-lateral chain), 1.23 (6H, m, CH$_3$-ethyl, CH3-ethyl lateral chain); MS (ES) m/e: 634.1 (MNa$^+$, 100%); Accurate mass: C$_{23}$H$_{30}$N$_7$O$_{11}$NaP required 634.1639, found 634.1624.

EXAMPLE 64

(S)-1-{[(2R,3S,4R,5R)-5-(4-Amino-2-oxo-2H-pyrimidin-1-yl)-2-azido-3,4-dihydroxy-tetrahydro-furan-2-ylmethoxy]-phenoxy-phosphoryl}-pyrrolidine-2-carboxylic acid ethyl ester (III-1)

The title compound was prepared according to Example 7 from 4'-azido-2',3'-isopropylidenecytidine-5'-[phenyl-(ethoxy-L-prolinyl)]-phosphate (70 mg, 0.105 mmol) dissolved in a 60/40 acetic acid/water mixture, and heated to 90° C. Removal of the solvents in vacuo and purification by preparative TLC purification developed with DCM/MeOH (9:1) afforded III-1 as a white solid (14 mg, 35%).

$^{31}$P NMR (121.5 MHz, d$_4$-MeOH): δ2.79, 2.43; $^1$H NMR (300 MHz, d$_4$-MeOH): δ7.72-7.61 (1H, dd, J=7.1, 25.0 Hz, H-6), 7.42-7.36 (2H, m, Ph-CH), 7.31-7.20 (3H, m, Ph-CH), 6.21-6.02 (1H, dd, J=4.6, 50 Hz, H-1'), 5.93-5.86 (1H, dd, J=14.2, 8.1 Hz, H-5), 4.45-4.09 (6H, m, H-5', Pro-CH and Ala-CH), 3.46-3.34 (2H, m, CH$_2$CH$_3$), 2.28-2.14 (1H, m, Pro-CH), 2.05-1.82 (3H, m, Pro-CH), 1.33-1.20 (3H, m, CH$_2$CH$_3$).

EXAMPLE 65

(S)-1-{[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-phenoxy-phosphoryl}-pyrrolidine-2-carboxylic acid ethyl ester (III-2)

The title compound was prepared as described in Example 4 utilizing 4'-azido-uridine (13a, 200 mg, 0.701 mmol), tert-BuMgCl (1.440 mL 1M solution in THF, 1.40 mmol), dry THF (10 mL), dry THF (10 mL) and 12am (1.40 mL 1M solution of THF, 1.40 mmol). The crude was purified by column chromatography and eluted with a CHCl$_3$/MeOH gradient (90:10 to 80:20) followed by a preparative TLC developed with CHCl$_3$/MeOH (90:10) which afforded III-2 as a white solid (17 mg, yield 5%).

$^{31}$P NMR (121.5 MHz, d$_4$-MeOH): δ2.83, 2.46; $^1$H NMR (300 MHz, d$_4$-MeOH): δ7.71-7.61 (1H, dd, J=8.1, 19.0 Hz, H-6), 7.43-7.38 (2H, m, Ph-CH), 7.31-7.21 (3H, m, Ph-CH), 6.19-6.05 (1H, dd, J=5.4, 37 Hz, H-1'), 5.77-5.65 (1H, dd, J=25.1, 8.2 Hz, H-5), 4.43-4.27 (3H, m, H-5' and Pro-CH) 4.2-4.11 (4H, m, Pro-CH and Ala-CH), 3.34-3.31 (2H, m, CH$_2$CH$_3$), 2.29-2.17 (1H, m, Pro-CH), 2.04-1.85 (3H, m, Pro-CH), 1.32-1.22 (3H, m, CH$_2$CH$_3$); $^{13}$C NMR (75.5 MHz, d$_4$-MeOH): δ175.13 (C=O), 166.22 (C-4), 158.87 (C-2), 152.46 (Ph-C), 142.98, 142.77 (C-6), 131.46, 131.33 (Ar—C), 126.85 (Ar—C), 121.75, 121.69, 121.44, 121.38 (Ar—C), 103.90 (C-5), 98.97, 98.85 (C-4'), 92.83, 92.27 (C-1'), 74.25, 74.01, 73.83 (C-2' and C-3'), 69.57 (C-5'), 62.93, 62.78 (Pro-CH), 62.25, 62.16 (Pro-CH), 32.84, 32.72 (Pro-CH), 26.54, 26.42 (Pro-CH), 14.85 (CH$_2$CH$_3$).

EXAMPLE 66

(S)-2-[[(2R,3S,4R,5R)-5-(4-Amino-2-oxo-2H-pyrimidin-1-yl)-2-azido-3,4-dihydroxy-tetrahydro-furan-2-ylmethoxy]-(4-chloro-phenoxy)-phosphorylamino]-4-methyl-pentanoic acid ethyl ester (I-16)

step 1—p-chloro-phenyl dichlorophosphate p-Chloro-phenyl dichlorophosphate was prepared as described in Example 2 from p-chlorophenol (3.0 g, 0.023 mol), POCl$_3$ (2.17 mL, 0.023 mol) and TEA (3.25 mL, 0.023 mol) and dry Et$_2$O (25 mL). The dichlorophosphate 11b was obtained as a yellow clear oil (4.15 g, 0.0169 mol, 40%) and used without further purification.

$^{31}$P NMR (CDCl$_3$): δ5.00; $^1$H NMR (CDCl$_3$): δ7.44 (2H, m, CH-phenyl), 7.30 (2H, m, CH-phenyl).

step 2—p-chloro-phenyl-(ethoxy-L-leucinyl)phosphorochloridate (12ab)

The title compound was prepared as described in Example 3B utilizing p-chlorophenyl dichlorophosphate (11b, 1.88 mL, 7.66 mmol), L-leucine ethyl ester hydrochloride salt (14q, 1.5 g, 7.66 mmol), dry TEA (2.14 mL, 15.32 mmol) and dry DCM (15 mL). The phosphorochloridate 12ab was obtained as a clear oil (2.16 g, 5.87 mmol, 77%).

$^{31}$P NMR (CDCl$_3$): δ$_P$ 9.75, 9.73; $^1$H NMR (CDCl$_3$): δ$_H$ 7.23 (2H, m, CH-phenyl), 7.12 (2H, m, CH-phenyl), 4.37 (1H, m, NH), 4.13 (2H, m, CH$_2$-ethyl), 3.99 (1H, m, CH-α), 1.78 (1H, m, CH-lateral chain), 1.53 (2H, m, CH$_2$-lateral chain), 1.16 (6H, m, CH$_3$-lateral chain), 0.82 (3H, m, CH$_3$-ethyl).

step 3—azido-cytidine 5'-O-[p-chloro-phenyl(ethoxy-L-leucinyl)phosphate

The title compound was prepared as described in Example 4 utilizing 4'-azido-cytidine (13b, 350 mg, 1.15 mmol), tert-BuMgCl (2.87 mL 1M solution in THF, 2.876 mmol) and 12ab (1.06 g, 2.88 mmol). The crude was purified by column chromatography and eluted with CHCl$_3$/MeOH (90:10) which afforded I-16 as a white solid (100 mg, 0.162 mmol, 14%).

$^{31}$P NMR (d$_4$-CH$_3$OH): δ$_P$ 5.19, 4.92; $^1$H NMR (d$_4$-CH$_3$OH): δ7.74 (1H, m, H6-cytidine, J=7.4 Hz), 7.36 (2H, m, CH-phenyl), 7.24 (2H, m, CH-phenyl), 6.15 (1H, m, H1'cytidine), 5.96 (1H, m, H5-cytidine, J=7.4 Hz), 4.37 (1H, m, H2'-cytidine), 4.25 (1H, m, H3'-cytidine), 4.15 (2H, m, CH$_2$-ethyl), 4.13 (2H, m, H5'-cytidine), 3.88 (1H, m, CH-α), 1.73 (1H, m, CH-lateral chain), 1.55 (2H, m, CH$_2$-lateral chain), 1.25 (3H, m, CH$_3$-lateral chain), 1.19 (3H, m, CH$_3$-lateral chain), 0.90 (3H, m, CH$_3$-ethyl); MS (ES) m/e: 638.1 (MNa$^+$, 100%); Accurate mass: C$_{23}$H$_{31}$N$_7$O$_9$NaPCl required 638.1495, found 638.1507.

EXAMPLE 67

(S)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(4-chloro-phenoxy)-phosphorylamino]-4-methyl-pentanoic acid ethyl ester (I-30)

The title compound was prepared as described in Example 4 utilizing 4'-azido-uridine (13a, 250 mg, 0.876 mmol), tert-BuMgCl (1.75 mL 1M solution in THF, 1.753 mmol) and 12ab (0.644 g, 1.753 mmol). The crude was purified by column chromatography and eluted with CHCl$_3$/MeOH (90:10) which afforded I-30 as a white solid (100 mg, 0.162 mmol, 14%).

$^{31}$P NMR (d$_4$-CH$_3$OH): 3.76, 3.46; $^1$H NMR (d$_4$-CH$_3$OH): δ7.67 (1H, m, H6-cytidine, J=10.4 Hz), 7.38 (2H, d, CH-phenyl, J=9.0 Hz), 7.26 (2H, d, CH-phenyl, J=9.0 Hz), 6.15 (1H, m, H1'cytidine), 5.72 (1H, m, H5-cytidine, J=10.4 Hz), 4.38 (1H, m, H2'-cytidine), 4.36 (1H, m, H3'-cytidine), 4.17 (2H, m, CH$_2$-ethyl), 4.13 (2H, m, H5'-cytidine), 3.89 (1H, m, CH-α), 1.73 (1H, m, CH-lateral chain), 1.55 (2H, m, CH$_2$-lateral chain), 1.26 (3H, m, CH$_3$-lateral chain), 1.23 (3H, m, CH$_3$-lateral chain), 0.91 (3H, m, CH$_3$-ethyl); MS (ES) m/e: 639.1 (MNa$^+$, 100%); Accurate mass: C$_{23}$H31N$_7$O$_9$NaPCl required 639.1348, found 639.1347.

EXAMPLE 68

(S)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(4-chloro-phenoxy)-phosphorylamino]-propionic acid benzyl ester (I-45)

The title compound was prepared as described in Example 4 utilizing 4'-azido-uridine (13a, 200 mg, 0.701 mmol), tert-BuMgCl (1.4 mL 1M solution in THF, 1.4 mmol), dry THF (10 mL) and 12z (1.4 mL 1M solution of THF, 1.4 mmol). The crude was purified by column chromatography and eluted with a CHCl$_3$/MeOH gradient (90:10 to 80:20) followed by a preparative TLC developed with CHCl$_3$/MeOH (90:10) which afforded I-45 as a white solid (25 mg, yield 6%).

$^{31}$P NMR (121.5 MHz, d$_4$-MeOH): δ4.81, 4.67; $^1$H NMR (300 MHz, d$_4$-MeOH): δ7.57-7.49 (1H, m, H-6), 7.27-7.20 (7H, m, Ph-CH), 7.16-7.08 (2H, m, Ph-CH), 6.06-5.95 (1H, m, H-1'), 5.64-5.55 (1H, m, H-5), 5.05 (2H, m, Bn-CH$_2$), 4.28 (2H, m, H-5'), 4.15-4.03 (2H, m, H-2' and H-3'), 3.99-3.89 (1H, m, Ala-CH), 1.32-1.20 (3H, m, Ala-CH$_3$); $^{13}$C NMR (75.5 MHz, d$_4$-MeOH): δ173.19, 173.14, 172.90, 172.83 (C=O), 164.22 (C-2), 150.61, 150.53 (Ph-C), 145.80, 145.70 (C-6), 141.23, 141.01 (Ar—C), 135.54 (Ar—C), 129.98, 129.19, 128.59 (Ar—C), 127.99, 127.76, 127.21, 127.70 (Ar—C), 126.37 (Ar—C), 121.43, 121.36 (Ar—C), 116.05 (Ar—C), 102.04, 101.95 (C-5), 97.08, 96.96, 96.83 (C-4'), 91.21, 90.75 (C-1'), 72.09, 71.93 (C-3'), 67.38, 67.21, 67.15, 66.46 (C-2'), 66.46 (Bn-CH$_2$), 50.15, 50.00 (Ala-CH), 18.86, 18.77, 18.63, 18.52 (Ala-CH$_3$).

EXAMPLE 69

(R)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(4-chloro-phenoxy)-phosphorylamino]-propionic acid benzyl ester (I-51)

step 1—p-chloro-phenyl-(benzyloxy-D-alaninyl)phosphorochloridate

The title compound was prepared as described in Example 3 utilizing 5.7 mL of a solution 1M in DCM of p-chlorophenyl dichlorophosphate (11b, 1.40 mL, 5.69 mmol), D-alanine benzyl ester tosylate salt (14m, 2 g, 5.69 mmol), dry TEA (1.6 mL, 11.38 mmol) and dry DCM (15 mL). The phosphorochloridate 12aa was obtained as a clear oil (2.16 g, 5.87 mmol, 77%).

$^{31}$P NMR (CDCl$_3$): δ9.37, 9.11; $^1$H NMR δ$_H$ (CDCl$_3$): 7.39 (9H, m, CH-phenyl), 5.18 (2H, d, CH$_2$-benzyl), 4.52 (1H, m, NH), 4.18 (1H, m, CH-α), 1.45 (3H, m, CH$_3$-lateral chain).

step 2—azido-uridine 5'-O-[p-chloro-phenyl(benzyloxy-L-alaninyl)phosphate

The title compound was prepared as described in Example 4 utilizing 4'-azido-uridine (13a, 215 mg, 0.754 mmol), tert-BuMgCl (1.1 mL 1M solution in THF, 1.130 mmol) and 1.1 mL of a 1M solution of p-chloro-phenyl-(benzyloxy-D-alaninyl)phosphorochloridate (12aa, 0.400 g, 2.88 mmol). The crude was purified by column chromatography and eluted with CHCl$_3$/MeOH (90:10). The product was further purified by preparative tlc on silica gel and developed with CHCl$_3$/MeOH (90:10) which afforded I-51 as a white solid (10 mg, 0.162 mmol, 2%).

$^{31}$P NMR (d$_4$-CH$_3$OH): δ$_P$ 4.92, 4.43; $^1$H NMR $^1$H NMR (d$_4$-CH$_3$OH): δ7.62 (1H, m, H6-cytidine), 7.36 (6H, m, CH-phenyl), 7.24 (3H, m, CH-phenyl), 6.12 (1H, m, H1'cytidine), 5.70 (1H, t, H5-cytidine, J=7.41 Hz), 5.16 (2H, CH$_2$-benzyl), 4.39 (1H, m, H2'-cytidine), 4.22 (1H, m, H3'-cytidine), 4.15 (2H, m, CH$_2$-ethyl), 4.05 (2H, m, H5'-cytidine), 3.68 (1H, m, CH-α), 1.35 (3H, m, CH$_3$-lateral chain); ms (ES) m/e: 659.0 (MNa$^+$, 100%); Accurate mass: C$_{25}$H$_{26}$N$_6$O$_{10}$NaPCl required 659.1029, found 659.1034.

EXAMPLE 70

(S)-2-[[(2R,3S,4R, 5R)-5-(4-Amino-2-oxo-2H-pyrimidin-1-yl)-2-azido-3,4-dihydroxy-tetrahydro-furan-2ylmethoxy]-(4-chloro-phenoxy)-phosphorylamino]-4-methyl-pentanoic acid ethyl ester (I-17)

step 1—3,4-dichloro-phenyldichloro phosphate 3,4-Dichloro-phenyl dichlorophosphate was prepared as described in Example 2 from p-chlorophenol (3.79 g, 0.023 mol), POCl$_3$ (2.17 mL, 0.023 mol) and TEA (3.25 mL, 0.023 mol) and dry Et$_2$O (25 mL).The dichlorophosphate 11c was obtained as a yellow clear oil (2.93 g, 0.0105 mol, 45%) and used without further purification.

$^{31}$P NMR (CDCl$_3$): δ4.79; $^1$H NMR (CDCl$_3$): δ7.41 (1H, m, CH-phenyl), 7.38 (1H, m, CH-phenyl), 7.33 (1H, m, CH-phenyl).

step 2—3,4-dichloro-phenyl-(ethoxy-L-leucinyl)phosphorochloridate

The title compound was prepared as described in Example 3 utilizing 3,4-dichloro-phenyl dichlorophosphate (11c, 7.6 mL of a 1M solution in DCM, 2.14 g, 7.66 mmol), L-leucine ethyl ester hydrochloride salt (14q, 1.5 g, 7.66 mmol), dry TEA (2.14 mL, 15.32 mmol) and dry DCM (15 mL). The phosphorochloridate 12ac was obtained as a clear oil (2.28 g, 5.66 mmol, 75%).

$^{31}$P NMR (CDCl$_3$): δ9.84, 9.78; $^1$H NMR (CDCl$_3$): δ7.41 (1H, m, CH-phenyl), 7.38 (1H, m, CH-phenyl), 7.33 (1H, m, CH-phenyl), 4.59 (1H, m, NH), 4.28 (1H, m, CHα), 4.09 (2H, m, CH$_2$-ethyl), 3.88 (1H, m, CH-α), 1.70 (1H, m, CH-lateral chain), 1.45 (2H, m, CH$_2$-lateral chain), 1.03 (6H, m, CH$_3$-lateral chain), 0.78 (3H, m, CH$_3$-ethyl).

step 3—azido-cytidine 5'-O-[3,4-dichloro-phenyl(ethoxy-L-leucinyl)phosphate

The title compound was prepared as described in Example 4 utilizing 4'-azido-cytidine (13b, 350 mg, 1.15 mmol), tert-BuMgCl (2.87 mL 1M solution in THF, 2.876 mmol) and 2.87 mL of solution 1M of 3,4-dichloro-phenyl-(ethoxy-L-leucinyl)phosphorochloridate (12ac, 1.06 g, 2.88 mmol). The crude was purified by column chromatography and eluted with CHCl$_3$/MeOH (90:10) which afforded I-17 as a white solid (40 mg, 0.061 mmol, 5%).

$^{31}$P NMR (d$_4$-CH$_3$OH): δ5.27, 4.99; $^1$H NMR (d$_4$-CH$_3$OH): δ7.70 (1H, m, H6-cytidine, J=7.5 Hz), 7.54-7.48 (2H, m, CH-phenyl), 7.25, 7.18 (1H, m, CH-phenyl), 6.13 (1H, m, H1'cytidine), 5.93 (1H, t, H5-cytidine, J=7.5 Hz), 4.39 (1H, m, H2'-cytidine), 4.28 (1H, m, H3'-cytidine), 4.13 (2H, m, CH$_2$-ethyl), 4.11 (2H, m, H5'-cytidine), 3.89 (1H, m, CH-α), 1.74 (1H, m, CH-lateral chain), 1.56 (2H, m, CH$_2$-lateral chain), 1.28 (3H, m, CH$_3$-lateral chain), 0.90 (3H, m, CH$_3$-ethyl); $^{13}$C NMR (d$_4$-CH$_3$OH): δ175.19 (1C, C=O ester), 168.05 (1C, C4-cytidine), 156.62 (1C, C2-cytidine), 151.31 (1C, C-phenyl), 143.96, 143.49 (1C, C6-cytidine), 132.70 (2C, CH-phenyl), 131.85 (1C, CH-phenyl), 124.17, 124.10 (1C, CH-phenyl), 122.32, 122.13, 122.06 (1C, CH-phenyl), 98.96, 98.83 (1C, C5-cytidine), 97.35, 97.23 (1C, C4'-cytidine), 94.14 (1C, C1'-cytidine), 74.84, 74.55 (1C, C3'-cytidine), 73.94, 73.81 (1C, C2'-cytidine), 69.65, 69.58 (1C, C5'-cytidine), 62.87, 62.78 (1C, CH$_2$-ethyl), 55.05, 54.98 (1C, CH-α), 44.38, 44.29 (1C, CH$_2$-lateral chain), 26.04, 25.91 (1C, CH-lateral chain), 23.68, 23.62, 23.52 (1C, CH$_3$-lateral chain), 22.23, 21.84 (1C, CH$_3$-lateral chain), 14.86 (1C, CH$_3$-ethyl); MS (ES) m/e: 672.1 (MNa$^+$, 100%), 674.1 (MNa$^+$, 48%); Accurate mass: C$_{23}$H$_{30}$N$_7$O$_9$NaPCl$_2$ required 672.1 101, found 672.11 17.

EXAMPLE 71

(S)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(3,4-dichloro-phenoxy)-phosphorylamino]-4-methyl-pentanoic acid ethyl ester (I-31)

The title compound was prepared as described in Example 4 utilizing 4'-azido-uridine (13a, 250 mg, 1.7535 mmol), tert-BuMgCl (1.75 mL 1M solution in THF, 1.753 mmol) and 2.87 mL of solution 1M of 3,4-dichloro-phenyl-(ethoxy-L-leucinyl)phosphorochloridate (12ac, 0.706 g, 1.753 mmol). The crude was purified by column chromatography and eluted with CHCl$_3$[MeOH (90:10). The product was further purified by preparative tlc on silica gel and developed with CHCl$_3$/MeOH (90:10) which afforded I-31 as a white solid (40 mg, 0.061 mmol, 5%).

$^{31}$P NMR (d$_4$-CH$_3$OH): δ3.84, 3.52; $^1$H NMR (d$_4$-CH$_3$OH): δ7.67 (1H, m, H6-cytidine, J=12.0 Hz), 7.53 (1H, d, CH-phenyl, J=9.0 Hz), 7/48 (1H, m, CH-phenyl), 7.22 (1H, d, CH-phenyl, J=9.0 Hz), 6.12 (1H, m, H1'-cytidine), 5.72 (1H, m, H5-cytidine, J=12.0 Hz), 4.39 (1H, m, H2'-cytidine), 4.36 (1H, m, H3'-cytidine), 4.22 (2H, m, CH$_2$-ethyl), 4.12 (2H, m, H5'-cytidine), 3.88 (1H, m, CH-α), 1.72 (1H, m, CH-lateral chain), 1.55 (2H, m, CH$_2$-lateral chain), 1.30 (3H, m, CH$_3$-lateral chain), 1.25 (3H, m, CH$_3$-lateral chain), 0.92 (3H, m, CH$_3$-ethyl); $^{13}$C NMR dept (d$_4$-CH$_3$OH): δ141.92 (1C, C6-uridine), 131.19 (1C, C5uridine), 122.61, 122.55 (1C, CH-phenyl), 120.56, 120.49 (1C, CH-phenyl), 102.44 (1C, Ch-phenyl), 98.65 (1C, C5-uridine), 92.03 (1C, C1'-uridine), 72.77, 72.66 (1C, C3'-uridine), 72.56, 72.41 (1C, C2'-uridine), 68.15 (1C, C5'-uridine), 61.26 (1C, CH$_2$-ethyl), 53.44 (1C, CH-α), 42.85, 42.76 (1C, CH$_2$-lateral chain), 24.53 (1C, CH-lateral chain), 22.15, 22.08 (1C, CH$_3$-lateral chain), 20.68, 20.28 (1C, CH$_3$-lateral chain), 13.32 (1C, CH$_3$-ethyl); MS (ES) m/e: 673.1 (MNa$^+$, 100%); Accurate mass: C$_{23}$H$_{30}$N$_7$O$_9$NaPCl$_2$ required 673.0968, found 673.0958.

EXAMPLE 72

(R)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(3,4-dichloro-phenoxy)-phosphorylamino]-propionic acid benzyl ester (I-52)

step 1—3,4-dichloro-phenyl-(benzyloxy-D-alaninyl)phosphorochloridate

The title compound was prepared as described in Example 3 utilizing 4.3 mL of a 1M solution of 3,4-dichlorophenyl dichlorophosphate in DCM (11c, 1.19 g mL, 4.267 mmol), D-alanine benzyl ester tosylate salt (1.5 g, 4.267 mmol), dry TEA (1.2 mL, 8.534 mmol) and dry DCM (15 mL). The phosphorochloridate 12ad was obtained as a clear oil (1.26 g, 3.24 mmol, 76%).

$^{31}$P NMR (CDCl$_3$): δ9.52, 9.35; $^1$H NMR (CDCl$_3$): δ7.40 (8H, m, CH-phenyl), 5.26 (2H, d, CH$_2$-benzyl), 4.59 (1H, m, NH), 4.28 (1H, m, CH-α), 1.58 (3H, m, CH$_3$-lateral chain).

step 2—azido-uridine 5'-O-[3,4-dichloro-phenyl(benzyloxy-L-alaninyl)phosphate

The title compound was prepared as described in Example 4 utilizing 4'-azido-uridine (13a, 215 mg, 0.754 mmol), tert-BuMgCl (1.1 mL 1M solution in THF, 1.130 mmol) and 1.1 mL of a 1M solution of 3,4-dichloro-phenyl(benzyloxy-D-alaninyl)phosphorochloridate (12ad, 0.400 g, 2.88 mmol). The crude was purified by column chromatography and eluted with $CHCl_3$/MeOH (90:10). The product was further purified by preparative tlc on silica gel and developed with $CHCl_3$/MeOH (90:10) which afforded I-52 as a white solid (10 mg, 0.162 mmol, 2%).

$^{31}$P NMR ($d_4$-$CH_3OH$): δ4.85, 4.56; $^1$H NMR ($d_4$-$CH_3OH$): δ7.62 (1H, m, H6-cytidine), 7.35 (8H, m, CH-phenyl), 6.08 (1H, m, H1'cytidine), 5.69 (1H, t, H5-cytidine), 5.17 (2H, $CH_2$-benzyl), 4.39 (1H, m, H2'-cytidine), 4.24 (1H, m, H3'-cytidine), 4.20 (2H, m, $CH_2$-ethyl), 4.05 (2H, m, H5'-cytidine), 3.70 (1H, m, CH-α), 1.38 (3H, m, $CH_3$-lateral chain); MS (ES) m/e: 693.0 ($MNa^+$, 100%); Accurate mass: $C_{25}H_{25}N_6O_{10}NaPCl_2$ required 693.0630, found 693.0645.

EXAMPLE 73

(S)-2-{[(2R,3S,4R,5R)-2-Azido-5-(2,4-dioxo-3,4-dihydro-2H-pyrimidin-1yl)-3,4-dihydroxy-tetrahydro-furan-2-ylmethoxy]-p-tolyloxy-phosphorylamino}-propionic acid ethyl ester (I-77)

The title compound was prepared as described in Example 4 utilizing 4'-azido-uridine (13a, 200 mg, 0.701 mmol), tert-BuMgCl (1.4 mL 1M solution in THF, 1.4 mmol), 1.4 mL of solution 1M of p-methylphenyl-(benzyloxy-L-alaninyl)-phosphorochloridate (12ae, 1.4 mmol) and dry THF (10 mL). The crude was purified by two column chromatographies and eluting with a $CHCl_3$/MeOH gradient (90:10 to 80:20). The product was further purified by preparative TLC and developed with $CHCl_3$/MeOH (90:10) which afforded I-77 as a white solid (31 mg, 8%).

$^{31}$P NMR (121.5 MHz, $d_4$-MeOH): δ4.97,4.73; $^1$H NMR (300 MHz, $d_4$-MeOH): 67.72-7.63 (1H, m, H-6), 7.25-7.15 (5H, m, Ph-CH), 6.23-6.17 (1H, m, H-1'), 5.78-5.69 (1H, m, H-5), 4.41 (2H, m, H-5'), 4.24-4.15 (4H, m, H-2', H-3' and $CH_2CH_3$), 4.05-3.98 (1H, m, Ala-CH), 2.38 (3H, br s, Ar—$CH_3$), 1.47-1.38 (3H, m, $CH_2CH_3$) 1.32-1.20 (3H, m, Ala-$CH_3$); $^{13}$C NMR (75.5 MHz, $d_4$-MeOH): δ175.52, 175.26, 175.19 (C=O), 166.25 (C-2), 152.62 (Ph-C), 150.19, 150.10 (C-6), 143.01, 142.83 (Ar—C), 136.66 (Ar—C), 131.68 (Ar—C), 121.51, 121.44 (Ar—C), 104.09, 104.01 (C-5), 99.22, 99.07, 98.94 (C-4'), 92.68, 92.24 (C-1'), 74.25, 74.18, 74.08 (C-3'), 69.23, 69.17 (C-2'), 62.89 (O—$CH_2$), 52.14, 51.96 (Ala-CH), 55.20 (Ar—$CH_3$), 21.14, 20.96, 20.87, 20.63 (Ala—$CH_3$), 14.84 ($CH_2CH_3$).

EXAMPLE 74

(S)-2-{[(2R,3S,4R,5R)-5-(4-Amino-2-oxo-2H-pyrimidin-1-yl)-2-azido-3,4-dihydroxy-tetrahydro-furan-2-ylmethoxy]-p-tolyloxy-phosphorylamino}-4-methyl-pentanoic acid ethyl ester (I-25)

step 1—p-methyl-phenyl dichloro phosphate
p-Methylphenyl dichlorophosphate was prepared as described in Example 2 from p-cresol (4.00 g, 0.037 mol), $POCl_3$ (3.45 mL, 0.037 mol) and TEA (5.15 mL, 0.037 mol) and dry $Et_2O$ (25 mL). The dichlorophosphate 11e was obtained as a yellow clear oil (7.91 g, 0.027 mol, 72%) and used without further purification.

$^{31}$P NMR ($CHCl_3$): δ4.98; $^1$H NMR ($CHCl_3$): δ7.22 (4H, m, CH-phenyl), 2.39 (3H, s, $CH_3$-p-cresol).

step 2—p-methyl-phenyl-(ethoxy-L-leucinyl)phosphorochloridate

The title compound was prepared as described in Example 3 utilizing p-methyl phenyl dichlorophosphate (11e, 7.6 mL of a 1M solution in DCM, 1.72 g, 7.66 mmol), L-leucine ethyl ester hydrochloride salt (14q, 1.5 g, 7.66 mmol), dry TEA (2.14 mL, 15.32 mmol) and dry DCM (15 mL). The phosphorochloridate 12ag was obtained as a clear oil (2.28 g, 5.66 mmol, 75%).

$^{31}$P NMR ($CHCl_3$): δ10.06, 9.63; $^1$H NMR ($CHCl_3$): δ7.05 (2H, d, CH-phenyl), 7.00 (2H, m, CH-phenyl), 4.67 (1H, m, NH), 4.26 (1H, m, CHα), 4.12 (2H, m, $CH_2$-ethyl), 1.87 (1H, m, CH-lateral chain), 1.69 (2H, m, $CH_2$-lateral chain), 1.45 (3H, m, $CH_3$-ethyl), 1.32 (3H, m, $CH_3$-lateral chain), 1.02 (3H, m, $CH_3$-lateral chain).

step 3—azido-cytidine 5'-O-[p-methyl-phenyl(ethoxy-L-leucinyl)phosphate

The title compound was prepared as described in Example 4 utilizing 4'-azido-cytidine (13b, 350 mg, 1.15 mmol), tert-BuMgCl (2.87 mL 1M solution in THF, 2.876 mmol) and p-methyl-phenyl-(ethoxy-L-leucinyl) phosphorochloridate (12ag, 2.87 mL of a 1M solution, 1.06 g, 2.88 mmol. The crude was purified by column chromatography and eluted with $CHCl_3$/MeOH (85:15) which afforded I-74 as a white solid (14 mg, 0.061 mmol, 4%).

$^{31}$P NMR ($d_4$-$CH_3OH$): δ5.24, 4.90; $^1$H NMR ($d_4$-$CH_3OH$): δ7.65 (1H, m, H6-cytidine, J=7.5 Hz), 7.15 (2H, m, CH-phenyl), 7.06 (2H, m, CH-phenyl), 6.20 (1H, m, H1'cytidine), 5.89 (1H, t, H5-cytidine, J=7.5 Hz), 4.32 (1H, m, H2'-cytidine), 4.23 (1H, m, H3'-cytidine), 4.17 (2H, m, $CH_2$-ethyl), 4.11 (2H, m, H5'-cytidine), 4.07 (1H, m, CH-α), 2.26 (3H, s, $CH_3$-p-phenyl), 1.72 (1H, m, CH-lateral chain), 1.55 (2H, m, $CH_2$-lateral chain), 1.25 (3H, m, $CH_3$-lateral chain), 1.18 (3H, m, $CH_3$-lateral chain), 0.91 (3H, m, $CH_3$-ethyl); $^{13}$C NMR ($d_4$-$CH_3OH$): δ175.31 (1C, C=O ester), 167.97 (1C, C4-cytidine), 150.11 (1C, C2-cytidine), 143.31, 143.08 (1C, C6-cytidine), 131.65, 131.60 (1C, C-phenyl), 130.86 (2C, CH-phenyl), 121.65, 121.59 (1C, C-phenyl), 121.47, 121.41 (2C, CH-phenyl), 98.92 (1C, C5-cytidine), 97.35 (1C, C4'-cytidine), 93.89 (1C, C1'-cytidine), 75.03, 74.83 (1C, C3'-cytidine), 73.89 (1C, C2'-cytidine), 69.26, 69.07 (1C, C5'-cytidine), 62.78, 62.72 (1C, $CH_2$-ethyl), 54.96 (1C, CHα), 44.54 (1C, $CH_2$-lateral chain), 26.03, 25.81 (1C, CH-lateral chain), 23.65, 23.56, 23.44 (1C, $CH_3$, lateral chain), 23.18, 22.39 (1C, $CH_3$, lateral chain), 14.67, 14.45 (1C, $CH_3$-ethyl).

EXAMPLE 75

(S)-2-{[(2R,3S,4R,5R)-2-Azido-5-(2,4-dioxo-3,4-dihydro-2H-pyrimidin-1yl)-3,4-dihydroxy-tetrahydro-furan-2-ylmethoxy]-p-tolyloxy-phosphorylamino}-4-methyl-pentanoic acid ethyl ester (I-37)

The title compound was prepared as described in Example 4 utilizing 4'-azido-uridine (13a, 250 mg, 1.753 mmol), tert-BuMgCl (1.75 mL 1M solution in THF, 1.753 mmol) and p-methyl-phenyl-(ethoxy-L-leucinyl)phosphorochloridate (12ae, 1.75 mL of a solution 1M solution, 0.610 g, 1.753 mmol). The crude was purified by column chromatography and eluted with $CHCl_3$/MeOH (90:10) which afforded I-37 as a white solid (50 mg, 0.084 mmol, 5%).

$^{31}$P NMR ($d_4$-$CH_3OH$): δ5.63, 5.22; $^1$H NMR ($d_4$-$CH_3OH$): δ7.55 (1H, m, H6-cytidine), 7.08 (2H, m, CH-phenyl), 7.04 (2H, m, CH-phenyl), 6.08 (1H, m, H1'cytidine), 5.60 (1H, m, H5-cytidine), 4.25 (1H, m, H2'-cytidine), 4.23 (1H, m, H3'-cytidine), 4.08 (2H, m, $CH_2$-ethyl), 4.04 (2H, m, H5'-cytidine), 3.79 (1H, m, CH-α), 2.23 (3H, s, CH₃-phenyl), 1.64 (1H, m, CH-lateral chain), 1.47 (2H, m, CH₂-lateral chain), 1.15 (3H, m, CH₃-lateral chain), 1.13 (3H, m, CH₃-lateral chain), 0.80 (3H, m, CH₃-ethyl); ¹³C NMR (d₄-CH₃OH): δ175.34 (1C, C=O ester), 166.19 (1C, C4-uridine), 152.71, 152.59 (1C, C2-uridine), 142.95, 142.66 (1C, C6-uridine), 131.68, 131.63 (2C, CH-phenyl), 121.65 (1C, C-phenyl), 121.59 (1C, C-phenyl), 121.43, 121.36 (2C, CH-phenyl), 99.29, 99.04, 98.91 (1C, C5-uridine), 92.52 (1C, C4'-uridine), 91.76 (1C, C1'-uridine), 74.45, 74.36 (1C, C3'-uridine), 74.19, 74.13 (1C, C2'-uridine), 69.33, 69.26 (1C, C5'-uridine), 62.81, 62.76, 62.66 (1C, CH₂-ethyl), 55.07, 54.93 (1C, CHα), 44.53, 44.44 (1C, CH₂-lateral chain), 44.10, 43.99 (1C, CH₃-phenyl), 26.22, 26.04, 25.82 (1C, CH₂-lateral chain), 23.67, 23.58, 23.46 (1C, CH₃, lateral chain), 22.87, 22.39, 21.99, 21.17 (1C, CH₃, lateral chain), 14.93, 14.87 (1C, CH₃-ethyl); MS (ES) m/e: 619.1 (M+Na)⁺, 100%; Accurate mass: C₂₄H₃₄N₇O₉NaP required 619.1891, found 619.1893.

EXAMPLE 76

(S)-2-[[(2R,3S,4R,5R)-5-(4-Amino-2-oxo-2H-pyrimidin-1-yl)-2-azido-3,4-dihydroxy-tetrahydro-furan-2-ylmethoxy]-(4-methoxy-phenoxy)-phosphorylamino]-4-methyl-pentanoic acid ethyl ester (I-26)

step 1—p-methoxy-phenyl dichloro phosphate p-methoxyphenyl dichlorophosphate (11d) was prepared as described in Example 2 from p-methoxyphenol (4.00 g, 0.032 mol), POCl₃ (3.00 mL, 0.032 mol) and TEA (4.49 mL, 0.032 mol) and dry Et₂O (25 mL). The dichlorophosphate 11d was obtained as a yellow clear oil (5.1 g, 0.021 mol, 67%) and used without further purification.

³¹P NMR (CHCl₃): δ5.45; ¹H NMR (CHCl₃): δ7.10 (2H, d, CH-phenyl, J=9.1 Hz), 6.80 (2H, d, J=9.1 Hz), 3.69 (3H, s, CH₃O-p-phenol).

step 2—p-methoxy-phenyl-(ethoxy-L-leucinyl)phosphorochloridate

The title compound was prepared as described in Example 3 utilizing p-methoxyphenyl dichlorophosphate (11d, 7.6 mL of a solution 1M in THF, 1.85 g, 7.66 mmol)), L-leucine ethyl ester hydrochloride salt (14q, 1.5 g, 7.66 mmol), dry TEA (2.14 mL, 15.32 mmol) and dry DCM (15 mL). The phosphorochloridate 12ai was obtained as a clear oil (1.71 g, 4.70 mmol, 61%).

³¹P NMR (CHCl₃): δ10.54, 10.22; ¹H NMR (CHCl₃): δ7.12 (2H, d, CH-phenyl, J=9.0 Hz), 6.85 (2H, d, J=9.0 Hz), 4.46 (1H, m, NH), 4.28 (1H, m, CHα), 3.85 (3H, s, CH₃O-p-phenyl), 1.86 (1H, m, CH-lateral chain),1.65 (2H, m, CH₂-lateral chain), 1.37 (3H, m, CH₃-ethyl), 1.32 (3H, m, CH₃-lateral chain), 0.96 (3H, m, CH₃-lateral chain).

step 3—azido-cytidine 5'-O-[p-methoxy-phenyl(ethoxy-L-leucinyl)phosphate

The title compound was prepared as described in Example 4 utilizing 4'-azido-cytidine (13b, 350 mg, 1.15 mmol), tert-BuMgCl (2.87 mL 1M solution in THF, 2.876 mmol) and of p-methoxy-phenyl-(ethoxy-L-leucinyl)phosphorochloridate (12ai, 2.87 mL of a 1M solution in THF, 1.05 g, 2.876 mmol. The crude was purified by column chromatography and eluted with CHCl₃/MeOH (90:10) which afforded I-26 as a white solid (20 mg, 0.032 mmol, 3%).

³¹P NMR (d₄-CH₃OH): δ5.59, 5.22; ¹H NMR (d₄-CH₃OH): δ7.71 (1H, m, H6-cytidine, J=7.6 Hz), 7.17 (2H, m, CH-phenyl), 6.91 (2H, m, CH-phenyl), 6.22 (1H, m, H1'cytidine), 5.96 (1H, m, H2-cytidine, J=7.6 Hz), 4.36 (1H, m, H2'-cytidine), 4.34 (1H, m, H3'-cytidine), 4.17 (2H, m, CH₂-ethyl), 410 (2H, m, H5'-cytidine), 3.91 (1H, m, CH-α), 3.79 (3H, s, CH₃O-phenyl), 1.74 (1H, m, CH-lateral chain), 1.56 (2H, m, CH₂-lateral chain), 1.27 (3H, m, CH₃-lateral chain), 1.21 (3H, m, CH₃-lateral chain), 0.92 (3H, m, CH₃-ethyl); ¹³C NMR (d₄-CH₃OH): δ175.33 (1C, C=O ester), 167.50 (1C, C4-cytidine), 158.99 (1C, C2-cytidine), 145.85, 145.76 (1C, C-phenyl),143.64, 143.42 (1C, C6-cytidine), 122.85, 122.79 (1C, C-phenyl), 122.67, 122.61 (2C, CH-phenyl), 157.11 (1C, C-phenyl), 99.30, 99.10, 98.97 (1C, C5-cytidine), 97.47, 97.39 (1C, C4'-cytidine), 93.90 (1C, C1'-cytidine), 74.99, 74.75, 74.05 (1C, C3'-cytidine), 73.90 (1C, C2'-cytidine), 69.22, 69.15 (1C, C5'-cytidine), 62.80, 62.73, 62.23 (1C, CH₂-ethyl), 56.53, 56.44 (1C, CH₃O-phenyl), 55.10, 54.96 (1C, CHα), 44.55, 44.45 (1C, CH₂-lateral chain), 26.04, 25.81 (1C, CH-lateral chain), 23.69, 23.59, 23.46, 23.23 (1C, CH₃, lateral chain), 22.41, 21.97 (1C, CH₃, lateral chain), 14.78, 14.56 (1C, CH₃-ethyl).

EXAMPLE 77

(S)-2-[[(2R,3S,4R,5R)-5-(4-Amino-2-oxo-2H-pyrimidin-1-yl)-2-azido-3,4-dihydroxy-tetrahydro-furan-2-ylmethoxy]-(4-methoxy-phenoxy)-phosphorylamino]-propionic acid benzyl ester (I-66)

The title compound was prepared as described in Example 4 utilizing 4'-azido-cytidine (13b, 300 mg, 0.999 mmol), tert-BuMgCl (2.0 mL 1M solution in THF, 2.876 mmol), p-methoxyphenyl-(benzyloxy-L-alaninyl)-phosphorochloridate (12ah, 2.0 mL of a 1M solution in THF, 2.0 mmol) and dry THF (15 mL). The crude was purified by two column chromatographies and eluting with a CHCl₃/MeOH gradient (90:10 to 80:20). The product was further purified by preparative TLC and developed with CHCl₃/MeOH (90:10) which afforded I-66 as a white solid (40 mg, 6%).

³¹P NMR (121.5 MHz, d₄-MeOH): δ$_P$5.17, 4.94; ¹H NMR (300 MHz, d₄-MeOH): δ7.64-7.56 (1H, dd, J=7.1, 14.2 Hz, H-6), 7.35-7.23 (5H, m, Ph-CH), 7.17-7.09 (2H, m, Ph-CH), 6.89-6.85 (2H, m, Ph-CH), 6.18-6.12 (1H, dd, J=5.3, 13.7 Hz, H-1'), 5.72-5.65 (1H, dd, J=14.2, 8.1 Hz, H-5), 5.16 (2H, m, Bn-CH₂) 4.43-4.30 (2H, m, H-2' and H-3'), 4.14 (2H, m, H-5'), 4.05-3.99 (1H, m, Ala-CH), 3.83 (3H, m, —OCH₃), 1.39-1.31 (3H, m, Ala-CH₃); ¹³C NMR (75.5 MHz, d₄-MeOH): δ175.00, 174.93 (C=O), 168.02 (C-2), 158.89, 158.58 (C-4), 145.80 (C-6), 143.45, 143.27 (Ar—C), 137.60 (Ar—C), 130.00, 129.92, 129.73, 129.69, 129.61 (Ar—C), 122.73, 122.67 (Ar—C), 116.13, 115.53 (Ar—C), 99.16, 99.05, 98.93 (C-4'), 94.14, 93.70 (C-1'), 74.90, 74.72, 73.86 (C-3'), 69.05 (C-2'), 68.43 (Bn-CH₂), 56.48 (—OCH₃), 52.20, 52.03 (Ala-CH), 20.90, 20.81, 20.57 (Ala-CH₃).

EXAMPLE 78

(S)-2-[[(2R,3S,4R,5R)-2-Azido-5-(2,4-dioxo-3,4-dihydro-2H-pyrimidin-1-yl-3,4-dihydroxy-tetrahydro-furan-2-ylmethoxy]-(4-methoxy-phenoxy)-phosphorylamino]-4-methyl-pentanoic acid ethyl ester (I-38)

The title compound was prepared as described in Example 4 utilizing 4'-azido-uridine (13a, 250 mg, 1.753 mmol), tert-BuMgCl (1.75 mL 1M solution in THF, 1.753 mmol) and p-methoxy-phenyl-(ethoxy-L-leucinyl)phosphorochloridate (12ai 0.638 g, 1.75 mL of a 1M solution in THF, 1.753 mmol). The crude was purified by column chromatography and eluted with CHCl₃/MeOH (90:10) which afforded I-38 as a white solid (42 mg, 0.069 mmol, 4%).

³¹P NMR (d₄-CH₃OH): δ5.64, 5.23; ¹H NMR (d₄-CH₃OH): δ7.65 (1H, m, H1-cytidine, J=16 Hz), 7.18 (2H, m, CH-phenyl), 6.91 (2H, m, CH-phenyl), 7.22 (1H, d, CH-phenyl), 6.17 (1H, m, H1'cytidine), 5.71 (1H, m, H2-cytidine, J=16 Hz), 4.36 (1H, m, H2'-cytidine), 4.34 (1H, m, H3'-cytidine), 4.18 (2H, m, CH₂-ethyl), 4.14 (2H, m, H5'-cytidine), 3.89 (1H, m, CH-α), 3.78 (3H, s, CH₃O-phenyl), 1.75 (1H, m, CH-lateral chain), 1.57 (2H, m, CH₂-lateral chain), 1.26 (3H, m, CH₃-lateral chain), 0.97 (3H, m, CH₃-lateral chain), 0.90 (3H, m, CH₃-ethyl); ¹³C NMR dept (d₄-CH₃OH): δ142.95, 142.67 (1C, C6-uridine), 122.83, 122.77, 122.63, 122.56 (2C, CH-phenyl), 116.16, 116.12 (2C, CH-phenyl), 104.18, 104.08 (1C, C5-uridine), 92.52 (1C, C4'-uridine), 91.78 (1C, C1'-uridine), 74.44, 74.37 (1C, C3'-uridine), 74.19, 74.12 (1C, C2'-uridine), 69.33, 69.26 (1C, C5'-uridine), 62.81, 62.76, 62.47 (1C, CH₂-ethyl), 56.52 (1C, CH₃O-phenyl), 55.08, 54.93 (1C, CHα), 45.16, 44.56 (1C, CH₂-lateral chain), 44.46, 43.99 (1C, CH₃-phenyl), 26.25, 26.05, 25.82 (1C, CH₂-lateral chain), 23.71, 23.61, 23.54 (1C, CH₃, lateral chain), 22.90, 22.41, 21.98 (1C, CH₃, lateral chain), 14.90 (1C, CH₃-ethyl);MS (ES) m/e: 635.1 (MNa⁺, 100%); Accurate mass: C₂₁H₃₄N₇O₁₀NaP required 635.1852, found 635.1843.

EXAMPLE 79

(S)-2-[[(2R,3S,4R,5R)-2-Azido-5-(2,4-dioxo-3,4-dihydro-2H-pyrimidin-1-yl)-3,4-dihydroxy-tetrahydro-furan-2-ylmethoxy]-(4-methoxy-phenoxy)-phosphorylamino]-propionic acid benzyl ester (I-65)

The title compound was prepared as described in Example 4 utilizing 4'-azido-uridine (13a, 200 mg, 0.701 mmol), tert-BuMgCl (1.4 mL 1M solution in THF, 1.4 mmol), dry THF (10 mL) and 12ah (1.4 mL 1M solution of THF, 1.4 mmol). The crude was purified by column chromatography and eluted with a CHCl₃/MeOH gradient (90:10 to 80:20) followed by a preparative TLC developed with CHCl₃/MeOH (90:10) which afforded I-65 as a white solid (55 mg, yield 12%).

³¹P NMR (121.5 MHz, d₄-MeOH): δ=5.24, 4.97; ¹H NMR (300 MHz, d₄-MeOH): δ 7.64-7.56 (1H, dd, J=7.1, 14.2 Hz, H-6), 7.35-7.23 (5H, m, Ph-CH), 7.17-7.09 (2H, m, Ph-CH), 6.89-6.85 (2H, m, Ph-CH), 6.18-6.12 (1H, dd, J=5.3, 13.7 Hz, H-1'), 5.72-5.65 (1H, dd, J=14.2, 8.1 Hz, H-5), 5.16 (2H, m Bn-CH₂), 4.38-4.30 (2H, m, H-2' and H-3'), 4.14 (2H, m, H-5'), 4.05-3.99 (1H, m, Ala-CH), 3.77 (3H, m, —OCH₃), 1.39-1.31 (3H, m, Ala-CH₃); ¹³C NMR (75.5 MHz, d₄-MeOH): δ175.33, 175.01, 174.94 (C=O), 166.23 (C-2), 158.87 (C-4), 152.69, 152.61 (Ph-C), 145.80, 145.70 (C-6), 142.98, 142.77 (Ar—C), 137.58 (Ar—C), 130.00, 129.74, 129.71, 129.68, 129.60 (Ar—C), 128.66, 128.39 (Ar—C), 122.72, 122.69, 122.63 (Ar—C), 116.15 (Ar—C), 104.10, 104.01 (C-5), 99.05, 98.92 (C-4'), 92.67, 92.22 (C-1'), 74.25, 74.16, 74.06 (C-3'), 69.21, 69.15 (C-2'), 68.45 (Bn-CH₂), 56.48 (—OCH₃), 52.20, 52.02 (Ala-CH), 20.91, 20.82, 20.68 (Ala-CH₃).

EXAMPLE 80

(R)-2-{[(2R,3S,4R,5R)-5-(4-Amino-2-oxo-2H-pyrimidin-1-yl)-2-azido-3,4-dihydroxy-tetrahydro-furan-2-ylmethoxy]-hydroxy-phosphorylamino}-propionic acid benzyl ester; compound with ammonia (I-68)

step 1—azido-cytidine 5'-monophosphate
The title compound was prepared as described in Example 5 utilizing 4'-azido-cytidine (13b, 200 mg, 0.657 mmol), POCl₃ (0.092 mL, 0.985 mmol), DMAP (120.34 mg, 0.985 mmol) in PO(OEt)₃ (1 mL). The crude was purified by column chromatography, eluting with iso-PrOH/conc. NH₄OH/H₂O (8:1.2:0.8) to afford azido-cytidine monophosphate as a yellow pure solid (180 mg, 0.497 mmol, 76%).

³¹P NMR (D₂O): δ3.56; ¹H NMR (D₂O): δ7.84 (1H, d, H6-cytidine, J=7.5 Hz), 6.08 (1H, d, H1'-cytidine, J=3.9 Hz), 6.00 (1H, d, H5-cytidine, J=7.5 Hz), 4.39-4.29 (2H, s, H2'-cytidine, H3'-cytidine), 3.95-3.78 (2H, m, H5'-cytidine); ¹³C NMR (d₄-CH₃OH): δ166.16 (1C, C4-cytidine), 157.34 (1C, C2-cytidine), 142.15 (1C, C6-cytidine), 98.44 (1C, C5-uridine), 96.97 (1C, C4'-uridine), 91.67 (1C, C1'-uridine), 73.40 (1C, C3'-uridine), 71.14 (1C, C2'-uridine), 65.34 (1C, C5'-uridine); MS (ES) m/e: 363.2 (M⁻, 100%); Accurate mass: C₉H₁₂N₆O₈P required 363.0454 found 363.0454.

step 2—azido-cytidine 5'-O-(benzyloxy-D-alaninyl)phosphate
The title compound was prepared as described in Example 5 utilizing azido-cytidine monophosphate (100 mg, 0.294 mmol), D-alanine benzyl ester tosylate salt (14m 368.83 mg, 2.058 mmol), DCC (302.82 mg, 1.47 mmol) in tert-BuOH (5 mL) and H₂O. The crude was purified by column chromatography eluting with a gradient starting from iso-PrOH, to iso-PrOH/conc. NH₄OH/H₂O (90:7:3, 85:10:5 and 80:12:8) to I-68 afford a white solid (7.8 mg, 0.0139 mmol, 7%).

³¹P NMR (D₂O): δ6.52; ¹H NMR (D₂O): δ7.63 (1H, d, H6-cytidine, J=7.8 Hz), 7.25 (5H, CH-benzyl), 5.91 (1H, d, H1'-cytidine, J=3.0 Hz), 5.86 (1H, d, H5-cytidine, J=7.8 Hz), 5.00 (2H, s, CH₂-benzyl), 4.25-4.13 (2H, m, H2'-cytidine, H3'-cytidine), 3.84 (2H, m, CH₂ (2H, m, H5'-cytidine), 3.71 (1H, m, CHα), 1.37 (3H, d, CH₃-lateral chain); MS (ES) m/e: 524.0 (M⁻, 100%); Accurate mass: C₁₉H₂₃N₇O₉P required 524.1295 found 524.1295.

EXAMPLE 81

2-{[(2R,3S,4R,5R)-2-((Z)-2-Chloro-vinyl)-5-(2,4-dioxo-3,4-dihydro-2H-pyrimidin-1yl)-3,4-dihydroxy-tetrahydro-furan-2-ylmethoxy]-phenoxy-phosphorylamino}-propionic acid benzyl ester (I-39)

The title compound was prepared as described in Example 4 utilizing cis-4'-(2-chloroethenyl)-uridine (13e, 100 mg, 0.33 mmol), tert-BuMgCl (0.7 mL 1M solution in THF, 0.7 mmol), phenyl-(benzyloxy-L-alaninyl)-phosphorochloridate (12an, 0.7 mL of a 1M THF solution, 0.7 mmol) and dry THF (10 mL). The crude was purified by column chromatography eluting with a CHCl₃/MeOH gradient (90: 10 to 80:20). The product was further purified by preparative TLC and developed with CHCl₃/MeOH (90: 10) which afforded I-39 as a white solid (19 mg, yield 9%).

³¹P NMR (121.5 MHz, d₄-MeOH): δ4.98, 4.67; ¹H NMR (300 MHz, d₄-MeOH): δ7.73-7.66 (1H, dd, J=7.1, 13.4 Hz, H-6), 7.39-7.34 (7H, m, Ph-CH), 7.33-7.18 (2H, m, Ph-CH), 6.89-6.85 (2H, m, Ph-CH), 6.18-6.12 (1H, dd, J=5.3, 13.7 Hz, H-1'), 6.02-5.96 (2H, m, C=C—H), 5.70-5.61 (1H, dd, J=18.8, 8.1 Hz, H-5), 5.19-5.15 (2H, m, Ph-CH₂), 4.45-4.31 (3H, m, H-5' and H'-3), 4.25-4.22 (1H, t, J=5.4 Hz, H'-2), 4.07-3.98 (1H, m, Ala-CH), 1.39-1.31 (3H, m, Ala-CH₃); ¹³C NMR (75.5 MHz, d₄-MeOH): δ175.24, 174.90 (C=O), 166.37 (C-4), 158.87 (C-2), 152.88, 152.45 (Ph-C), 142.78, 142.73 (C-6), 137.64, 137.59 (Ar—C), 131.29, 131.01, 130.01, 129.74, 129.71, 129.69, 129.58, 129.54 (Ar—C), 128.38 (Ar—C), 126.75 (Ar—C), 122.60, 122.53 (Ar—C), 121.83, 121.79, 121.76, 121.73 (Ar—C), 103.81, 103.75 (C-5), 90.17 (C-1'), 88.56, 88.51, 88.44, 88.40 (C=C), 75.39, 75.32 (C-3'), 72.99, 72.90 (C-2'), 68.79, 68.44, 68.40 (C-5'), 65.62 (Bn-CH$_2$), 52.19, 52.02 (Ala-CH), 20.95, 20.67, 20.57 (Ala-CH$_3$).

EXAMPLE 82

2-[[2-Azido-5-(2,4-dioxo-3,4-dihydro-2H-pyrimidin-1-yl)-3,4-dihydroxy-tetrahydro-furan-2-ylmethoxy]-(3-bromo-naphthalen-2-yloxy)-phosphorylamino]-propionic acid benzyl ester (I-86)

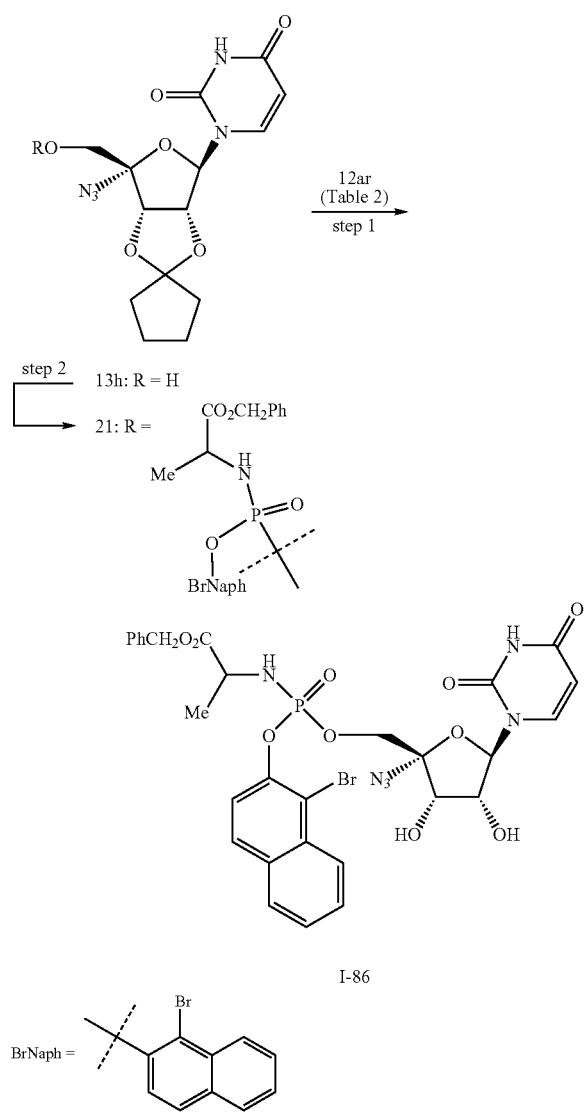

step 1—Protection of the 2',3'-diols of a ribose sugar as a cyclopentylidene ketal is readily accomplished from the nucleoside using standard methodology (T. W. Greene and P. G. M. Wuts; *Protecting Groups in Organic Synthesis, 3$^{rd}$ Ed.*, J. T. Wiley & Sons: New York, N.Y., 1999, pp. 215-217). The phosphoramidate 21 was prepared as described in Example 4 utilizing 13h (140 mg, 0.4 mmol), tert-BuMgCl (0.8 mL, 1M in THF, 0.8 mmol), 12ar (387 mg, 0.8 mmol) and dry THF (8 mL). The crude was purified by column chromatography on SiO$_2$ eluting with CHCl$_3$/MeOH (98:2) which afforded 310 mg (97%) of 21 as a white foam.

$^{31}$P NMR (121.5 MHz, d$_4$-MeOH): δ$_P$=2.99; $^1$H NMR (500 MHz, d$_4$-MeOH): δ$_H$ 8.25-8.21 (1H, m, Ar—CH), 7.88-7.84 (5H, m, Ar—CH), 7.69-7.52 (3H, m, Ar—CH and H-6), 7.34-7.27 (3H, m, Ar—CH), 5.94-5.88 (1H, m, H-1'), 5.66-5.60 (1H, m, H-5), 5.15-4.95 (4H, m, Bn-CH$_2$ and H-5'), 4.39-4.29 (2H, m, H-2' and H-3'), 4.21-4.20 (1H, m, Ala-CH), 2.10-2.06 (2H, m, CyPt—CH), 1.71-1.62 (6H, m, CyPt—H), 1.44-1.42 (3H, m, Ala-CH$_3$); $^{13}$C NMR (75.5 MHz, d$_4$-MeOH): δ$_C$ 174.75, 174.71, 174.61 (C=O), 165.98 (C-4), 151.84, 151.77 (C-2), 147.34 (Ar—C), 145.11, 144.73 (C-6), 137.11 (Ar—C), 134.08, 134.03 (Ar—C), 133.20 (Ar—C), 130.32, 130.28, (Ar—C) 129.64, 129.60, 129.51, 129.39, 129.34, 129.28, 129.25, (Ar—C), 127.78, 127.76, 127.36, (Ar—C), 126.18 (Ar—C), 121.27, 121.24 (Ar—C), 114.04, 113.97 (Ar—C), 103.39, 103.23 (C-5), 100.58, 100.51 (C-4'), 95.20, 94.79 (C-1'), 85.12, 85.08 (C-2'), 84.77, 83.62 (C-3'), 70.00, 69.95 (C-5'), 68.18, 68.12 (Bn-CH$_2$), 51.80, 51.66 (Ala-CH), 37.28, 37.13 (CyPt—CH$_2$), 36.29, 36.18 (CyPt—CH$_2$), 24.85 (CyPt—CH$_2$), 24.06 (CyPt—CH$_2$), 20.66, 20.61, 20.53, 20.47 (Ala-CH$_3$).

step 2—A solution of 21 (310 mg, 0.39 mmol) and 60/40 HCO$_2$H/H$_2$O mixture (15 mL), and stirred at RT for 8 h. The crude was purified by column chromatography on SiO$_2$ eluting with CHCl$_3$/MeOH (gradient, 100:0 to 97:3) which afforded 186 mg (64%) of I-86 as a white foam.

$^{31}$P NMR (121.5 MHz, d$_4$-MeOH): δ$_P$=3.50, 3.27; $^1$H NMR (500 MHz, d$_4$-MeOH): δ$_H$ 8.25-8.23 (1H, m, Ar—CH), 7.92-7.87 (2H, m, Ar—CH), 7.71-7.63 (3H, m, Ar—CH and H-6), 7.58-7.53 (1H, m, Ar—CH), 7.35-7.27 (5H, m, Ar—CH), 6.17-6.11 (1H, m, H-1'), 5.69-5.53 (1H, m, H-5), 5.14-5.07 (2H, m, Bn-CH$_2$), 4.43-4.37 (2H, m, H-5'), 4.36-4.26 (2H, m, H-2' and H-3'), 4.22-4.13 (1H, m, Ala-CH), 1.42-1.40 (3H, m, Ala-CH$_3$); $^{13}$C NMR (75.5 MHz, d$_4$-MeOH): δ$_C$ 174.20 (C=O), 165.78 (C-4), 152.24 (C-2), 147.24, 147.22 (Ar—C), 142.54, 142.40 (C-6), 137.12 (Ar—C), 134.02 (Ar—C), 133.22 (Ar—C), 130.46, 130.42 (Ar—C), 129.62, 129.60, 129.53, 129.53, 129.30 (Ar—C), 127.69, 127.47, 127.44 (Ar—C), 121.02, 120.97 (Ar—C), 113.80 (Ar—C), 103.81, 103.61 (C-5), 98.73, 98.65 (C-4'), 92.33, 91.85 (C-1'), 73.99, 73.86, 73.65 (C-2' and C-3'), 69.31, 69.28 (C-5'), 68.16, 68.12 (Bn-CH$_2$), 51.86, 51.70 (Ala-CH), 20.55, 20.50, 20.32, 20.25 (Ala-CH$_3$).

EXAMPLE 83

2-[[5-(6-Amino-purin-9-yl)-2-azido-3,4-dihydroxy-tetrahydro-furan-2-ylmethoxy]-(naphthalen-1-yloxy)-phosphorylamino]-propionic acid benzyl ester (I-87)

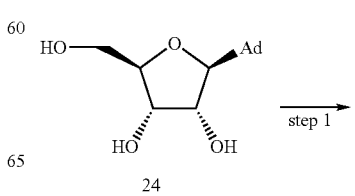

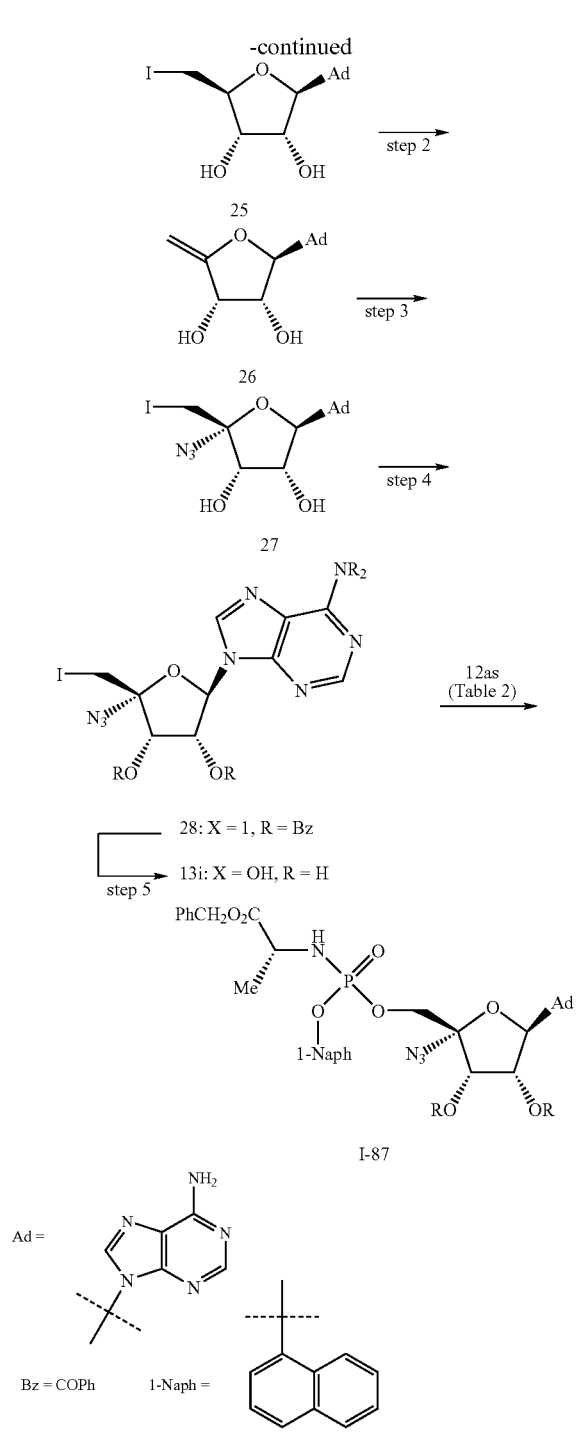

step 1—Iodine (35.43 g, 0.140 mol) and Ph₃P (36.80 g, 0.140 mol) were added to a solution of adenosine (24, 25 g, 0.093 mol) in pyridine (200 mL). After 2 h a saturated solution of Na₂S₂O₃ was added, the solvent was removed in vacuo and the yellow solid was purified by column chromatography on SiO₂ eluting with CHCl₃/MeOH (9:1) to afford 60 g (>100%) of 25 which was sufficiently pure to use in the subsequent step.

¹H NMR $\delta_H$ (d₆-(CH₃)₂SO): 8.82 (1H, s, NH₂-adenosine), 8.59 (1H, s, H2-adenosine), 8.36 (1H, s, H8-adenosine), 5.95 (1H, d, H1'-adenosine, J=5.6 Hz), 4.75 (1H, t, H2'-adenosine), 4.16 (1H, t, H3'-adenosine), 4.01 (1H, m, H4'-adenosine), 3.60 (1H, m, H5'-adenosine), 3.46 (1H, m, CH5'-adenosine).

step 2—To a solution of 5'-deoxy-5'-iodo-adenosine (25, 35 g, 0.093 mol) in pyridine (200 mL) was added potassium tert-butoxide (47.0 g, 0.418 mol), and the reaction stirred for 1 h at 80° C. The solvent was removed under reduced pressure and the black solid was purified by column chromatography on SiO₂ eluting with a CHCl₃/MeOH gradient (90% to 70% CHCl₃) to afford 18.54 g (80%) of 26 as a brown 20 solid.

¹H NMR $\delta_H$ (d₆-(CH₃)₂SO): 8.37 (1H, s, H2-adenosine), 8.16 (1H, s, H8-adenosine), 7.32 (2H, s, NH₂-adenosine), 6.16 (1H, d, H1'-adenosine, J=5.3 Hz), 5.73 (1H, s, OH-2'-adenosine), 5.58 (1H, s, OH-3'-adenosine), 4.83 (1H, t, H2'-adenosine), 4.73 (1H, t, H3'-adenosine), 4.31 (1H, s, H5'-adenosine), 4.21 (1H, s, H5'-adenosine).

step 3—Sodium azide (11.73 g, 0.1804 mol) was added to a solution of ICl (14.65 g, 0.0902 mol) in DMF (50 mL) and the resulting solution was stirred for 20 min at 30° C. A solution of 1-(5-deoxy-β-D-glycero-pent-4-enofuranosyl)-adenosine (26, 9 g, 0.0361 mmol) in DMF (200 mL) then was added dropwise over a 30 min interval. After 1 h a saturated solution of Na₅S₂O₃ was added and the solvent was removed under reduced pressure. The resulting solid was dissolved in MeOH and any precipitate was removed by filtration. The MeOH was removed in vacuo and the yellow solid was purified by column chromatography on SiO₂ eluting with CHCl₃/MeOH (9:1) to afford 19 g (>100%) of 27 as a yellow solid.

¹H NMR $\delta_H$ (d₄-CH₃OH): 8.86 (1H, s, H2-adenosine), 8.78 (1H, s, H8-adenosine), 6.26 (1H, d, H1'-adenosine, J=5.1 Hz), 5.28 (1H, m, H2'-adenosine), 4.73 (1H, t, H3'-adenosine), 3.71 (1H, s, H5'-adenosine), 3.68 (1H, s, H5'-adenosine); ¹³C NMR $\delta_C$ (d₄-CH₃OH): 157.39 (1C, C4-adenosine), 154.17 (1C, CH2-adenosine), 153.80 (1C, CH8-adenosine), 150.68 (1C, C6-adenosine), 120.70 (1C, C5-adenosine), 98.77 (1C, C4'-adenosine), 91.22 (1C, CH1'-adenosine), 75.30 (1C, CH3'adenosine), 73.98 (1C, CH2'-adenosine), 9.61 (1C, CH₂5'-adenosine).

step 4—To a solution of 27 in pyridine was added benzoyl chloride. After 15 h the solvent was removed in vacuo and the resulting dark solid was purified by column chromatography on SiO₂ eluting with EtOAc/Hexane (3:7) to afford 8.5 g (35%) of 28a as a yellow solid.

¹H NMR $\delta_H$ (d₄-CH₃OH): 8.76 (1H, s, H2-adenosine), 8.67 (1H, s, H8-adenosine), 8.06-7.86 (10H, m, benzoyl), 7.63-7.40 (10H, m, benzoyl), 6.88 (1H, d, H3'-adenosine, J=3.0 Hz), 6.60-6.59 (2H, m, H2'-adenosine, H1'-adenosine), 3.93 (1H, m, H5'-adenosine); ¹³C NMR $\delta_C$ (d₄-CH₃OH): 166.46 (1C, C=O-benzoyl), 166.07 (1C, C=O-benzoyl), 153.94 (1C, C=O-benzoyl), 153.32 (1C, C=O-benzoyl), 135.39 (2C, C-benzoyl), 135.15 (1C, CH-benzoyl), 135.08 (1C, CH-benzoyl), 134.38 (1C, CH-benzoyl), 134.03 (1C, CH-benzoyl), 131.07 (2C, CH-benzoyl), 131.07 (2C, CH-benzoyl), 130.90 (4C, CH-benzoyl), 130.74 (2C, CH-benzoyl), 130.55 (2C, CH-benzoyl), 129.91 (2C, CH-benzoyl), 129.80 (2C, CH-benzoyl), 129.73 (2C, CH-benzoyl), 129.46 (2C, CH-benzoyl), 97.93 (1C, C4'-adenosine), 89.94 (1C, CH3'-adenosine), 74.74 (1C, CH2'-adenosine), 74.67 (1C, CH1'-adenosine), 6.70 (1C, CH5'-adenosine).

step 5- To a solution of 4-N,N-dibenzoyl, 2',3'-O,O-dibenzoyl-4'-azido-5'-deoxy-5'-iodo-adenosine (28a, 2.20 g, 2.64 mmol) in 20 mL of DCM (saturated with 1% of water), 85% MCPBA (3.63 g, 15.84 mmol) was added and the reaction stirred at 40° C. for 1 h. EtOAc was added and the resulting solution was washed with a saturated solution of Na₅S₂O₃. The EtOAc solution was dried (MgSO₄), filtered, and the solvents removed in vacuo. The yellow solid was dissolved in 6 mL of 1 N methanolic sodium methoxide and stirred for 1 h. The volatile solvents were removed in vacuo and the resulting crude material was purified by SiO₂ chromatography eluting with CHCl₃/MeOH (9:1 containing 1% concentrated NH₄OH) to afford 200 mg (24%) of 13i.

¹H NMR $\delta_H$ (d₄-CH₃OH): 8.31 (1H, s, H2-adenosine), 8.19 (1H, s, H8-adenosine), 6.25 (1H, d, H1'-adenosine, J=6.4 Hz), 5.00 (1H, t, H2'-adenosine), 4.53 (1H, d, H3'-adenosine), 3.77 (1H, d, H5'-adenosine, J=12.2 Hz), 3.60 (1H, d, H5'-adenosine, J=12.2 Hz); low resolution ms (ES) m/e: 331.1 (MNa⁺, 100%); high resolution ms: for $C_{10}H_{12}N_8O_4Na$, required 331.0879, found 331.0886.

step 6—The title compound was prepared as described in Example 4 utilizing 4'-azido-adenosine (13i, 165.6 mg, 0.0537 mmol), ¹BuMgCl (1.34 mL 1M solution of THF, 1.343 mmol) and α-naphthyl-(benzyloxy-L-alaninyl) phosphorochloridate (1.34 mL of solution 1M in THF, 1.343 mmol). The crude was purified by preparative HPLC on SiO₂ eluting with CHCl₃/MeOH (85:15) to afford 20.2 mg (6%) of I-87 as a white solid.

³¹P NMR $\delta_P$ (d₄-CH₃OH): 3.71, 3.67; ¹H NMR $\delta_H$ (d₄-CH₃OH): 8.26 (1H, d, H2-adenosine), 8.17 (1H, s, H8-adenosine), 8.17 (1H, s, CH-naphthyl), 7.88 (1H, d, CH-naphthyl, J=7.9 Hz), 7.69 (1H, m, CH-naphthyl), 7.53-7.43 (4H, m, 3 CH-naphthyl, 1 CH-phenyl), 7.38-7.25 (5H, CH-naphthyl, 4 CH-phenyl), 6.28 (1H, d, H1'-adenosine, J=5.1 Hz), 5.05 (2H, m, CH₂-benzyl), 4.95 (1H, m, H2'-adenosine), 4.70 (1H, d, H3'-adenosine, J=5.4 Hz), 4.40 (2H, m, H5'-adenosine), 4.05 (1H, m, CHα), 1.28 (3H, m, CH₃-alanine); low resolution ms (ES) m/e: 698.1 (MNa⁺, 100%); high resolution ms: for $C_{30}H_{30}N_9O_7Na$, required 698.1853, found 698.1852.

EXAMPLE 84

2-[[2-Azido-3,4-dihydroxy-5-(6-oxo-1,6-dihydropurin-9-yl)-tetrahydro-furan-2-ylmethoxy]-(naphthalen-1-yloxy)-phosphorylamino]-propionic acid benzyl ester (I-88)

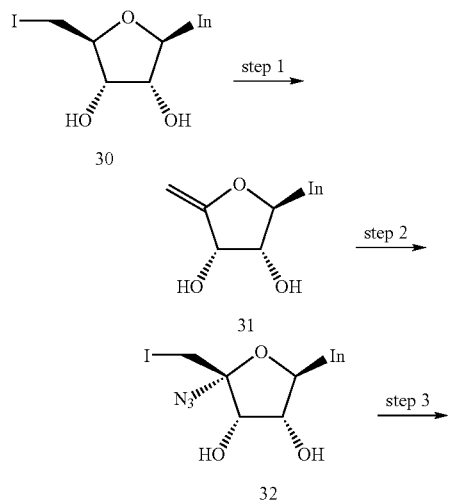

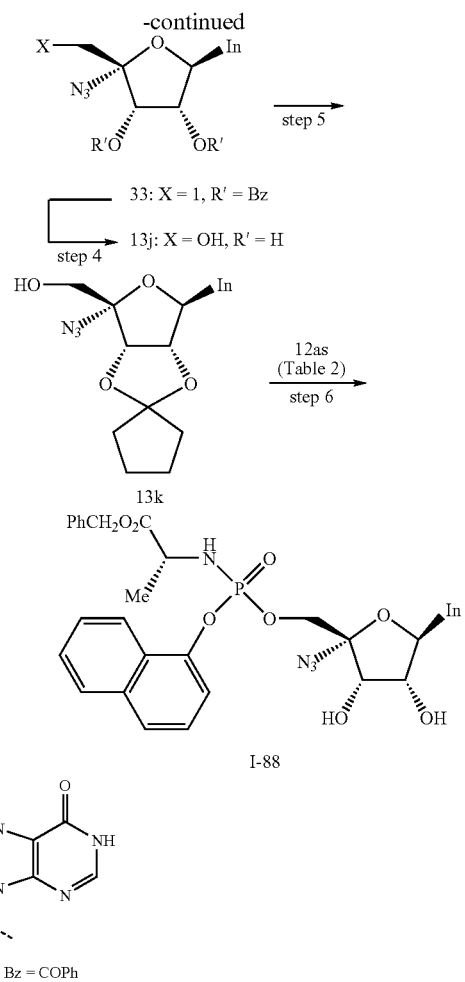

step 1—To a suspension of inosine (20.00 g, 74.56 mmol) in pyridine (200 mL) was added Ph₃P (30.40 g, 113.34 mmol) and I₂ (28.77, 113.34 mmol). The mixture was stirred at RT overnight, MeOH was added and the solvent evaporated in vacuo. The crude purified by column chromatography on SiO₂ eluting with a CHCl₃/MeOH gradient (10 to 20% MeOH). The solid obtained was suspended in EtOH, refluxed for 0.5 h and filtered to afford 20.32 g (72%) of 30 as a white solid.

¹H-NMR (DMSO-d₆; 500 MHz): δ 12.42 (1H, bs, H-1), 8.35 (1H, s, H-8), 8.10 (1H, s, H-2), 5.91 (1H, d, ³J=5.8 Hz, H-1'), 4.71 (1H, ψt, ³J=5.4 Hz, H-2'), 4.13 (1H, 104 d, ³J=4.6 Hz, H-3'), 4.01 (1H, m, H-4'), 3.62-3.59 and 3.48-3.44 (2H, 2m, H-5'); ¹³C-NMR (DMSO-d₆; 125.7 MHz): δ 7.65 (C-5'), 73.08, 73.17 (C-3'+C-2'), 83.98 (C-4'), 87.39 (C-1'), 124.41 (C-5), 139.02 (C-8), 146.00 (C-2), 148.33 (C-4), 156.51 (C-6).

step 2—A 1 M solution of sodium methoxide (32 mL) was added to a suspension of 5'-deoxy-5'-iodoinosine (30, 3.11 g, 8.22 mmol) in MeOH (100 mL). The solution was heated at reflux for 5 h, cooled at RT and purified by column chromatography on SiO₂ eluting with a CHCl₃/MeOH gradient (10 to 20% MeOH) to afford 1.25 g (61%) of 31 as a white solid.

¹H-NMR (DMSO-d₆; 500 MHz): δ 12.44 (1H, bs, H-1), 8.35 (1H, s, H-8), 8.11 (1H, s, H-2), 6.35 (1H, d, ³J=4.3 Hz, H-1'), 5.83 (1H, bs, OH-2'), 5.58 (1H, bs, OH-3'), 4.76 (1H, m, H-2'), 4.65 (1H, m, H-3'), 4.33, 4.23 (2H, 2s, H-5'); $^{13}$C-NMR (MeOD; 125.7 MHz): δ 69.45 (C-3'), 72.27 (C-2'), 85.01 (C-5'), 87.73 (C-1'), 124.65 (C-5), 139.20 (C-8), 146.17 (C-2), 148.30 (C-4), 156.52 (C-6), 161.89 (C-4'); MS (ES+) m/e 273.07 (MNa$^+$, 100%).

step 3—Sodium azide (1.55 g, 23.9 mmol) was added under argon to a stirred solution of iodine monochloride (1.94 g, 11.95 mmol) in DMF (30 mL) at room temperature. The mixture was stirred at room temperature for 20 min and after this time a solution of 9-(5-deoxy-β-D-erythro-pent-4-enofuranosyl)hypoxanthine (31, 1.20 g, 4.78 mmol) in DMF (300 mL) was added dropwise over 30 min. The mixture was stirred for 4 h then saturated solution of sodium bicarbonate was added followed by sodium thiosulfate. The solvent was evaporated in vacuo and the crude product purified by column chromatography on silica gel eluting with a CHCl$_3$/MeOH gradient (20 to 30% MeOH) to afford 1.16 g (58%) of 32 as a white solid (1.16 g, 58%).

$^1$H-NMR (DMSO-d$_6$; 500 MHz): δ 12.41 (1H, bs, H-1), 8.46 (1H, s, H-8), 8.12 (1H, s, H-2), 6.41 (1H, bs, OH-2'), 6.17 (1H, d, $^3$J=7.0 Hz, H-1'), 5.88 (1H, bs, OH-3'), 5.02-4.99 (1H, m, H-2'), 4.47-4.46 (1H, m, H-3'), 3.73, 3.60 (2H, 2d, $^2$J=11.1 Hz, H-5'); $^{13}$C-NMR (MeOD; 125.7 MHz): δ 11.33 (C-5'), 72.18 (C-2'), 74.57 (C-3'), 87.51 (C-1'), 97.42 (C-4'), 124.61 (C-5), 139.29 (C-8), 146.28 (c-2), 148.43 (C-4), 156.50 (C-6).

step 4—To a solution of 32 (1.10 g, 2.62 mmol) and PTSA (81 mg, 0.66 mmol) in pyridine (20 mL) was added benzoyl chloride (1.47 g, 10.48 mmol, 1216 μL) and the reaction stirred at RT for 3.5 h. The solvent was removed in vacuo and the crude product purified by column chromatography on SiO$_2$ eluting with a CHCl$_3$/MeOH gradient (2 to 5% MeOH) to afford 1.49 g (91%) of 33 as a yellow solid.

$^1$H-NMR (MeOD; 500 MHz): δ 8.34 (1H, s, H-8), 8.20 (1H, s, H-2), 8.05-7.38 (10H, m, Bz), 6.80-6.79 (1H, m, H-1'), 6.54-6.53 (1H, m, H-3'), 6.50-6.48 (1H, m, H-2'), 3.96, 3.90 (2H, 2d, $^2$J=11.4 Hz, H-5').

step 5—A solution of 33 (4.08 g, 6.50 mmol) and MCPBA (5.83 g, 4.49 mmol) in water-saturated DCM was heated at reflux and stirred for 4 h. The reaction mixture was diluted with EtOAc, washed with sodium meta-bisulfite solution followed by saturated NaHCO$_3$. The organic phase was dried (MgSO4), and evaporated to provide a foam. The foam was dissolved in MeOH (30 mL) and a 1M solution of sodium methoxide in methanol was added (5 mL) and the reaction stirred at RT for 1 h. The reaction was neutralized with DOWEX® resin, filtered and the solvent removed in vacuo. The crude was purified by two successive column chromatographies on SiO$_2$ eluting with EtOAc/IPA/H$_2$O (88/10/2) to afford 217 mg (11%) of 13j.

$^1$H-NMR (MeOD; 500 MHz): δ 8.36 (1H, s, H-8), 8.12 (1H, s, H-2), 6.30 (1H, d, $^3$J=5.8 Hz, H-1'), 4.88-4.86 (1H, m, H-2'), 4.43 (1H, d, $^3$J=5.4 Hz, H-3'), 3.69 (1H, m, H-5'); $^{13}$C-NMR (MeOD; 125.7 MHz): δ 65.69 (C-5'), 74.31 (C-3'), 75.22 (C-2'), 91.04 (C-1'), 101.42 (C-4'), 126.10 (C-5), 141.10 (C-8), 147.09 (C-2), 149.81 (C-4), 154.84 (C-6); ms (ES+) m/e 332.08 (MNa$^+$, 100%).

step 6—The cyclopentylidene protected group was incorporated by treating 13j with cyclopentanone, HC(OMe)$_3$ and pTSA in MeCN. The phosphoramidate was introduced using the procedure in Example 4 utilizing 13j (65 mg, 0.17 mmol), 1-naphthyl(benzoxy-L-alaninyl)-phosphochloridate (12as, 1M solution in THF, 0.433 mmol, 433 μL), tert-butylmagnesium choride (1 M solution in THF, 433 μL) and THF (15 mL). The reaction was stirred for 4 h, the solvent removed and the crude purified by SiO$_2$ column chromatography eluting with a CHCl$_3$/MeOH gradient (starting with 5% MeOH). The appropriate fractions were collected and the solvent removed under reduced pressure to afford 75 mg (59%) of 35 as a white solid.

$^{31}$P-NMR (MeOD; 202.5 MHz): δ 3.69, 3.56; $^1$H-NMR (MeOD; 500 MHz): δ 8.18, 8.17 (1H, 2s, H-8), 8.15-7.23 (13H, m, naphthyl, PhCH$_2$ and H-2), 6.45-6.41 (1H, 2s, H-1'), 5.36-5.02 (2H, m, PhCH$_2$+H-2'+H-3'), 4.37-4.32 (1H, m, H-5'), 4.11-4.04 (1H, m, CH$_3$CH), 2.29-2.12 (2H, m, cyclopentylidene), 1.89-1.61 (6H, m, cyclopentylidene), 1.5-1.34 (3H, m, CH$_3$CH).

step 7—A solution of 35 (75 mg, 0.101 mmol) and HCOOH (80% v/v solution in water, 10 mL) was stirred at RT for 10 h. The solvent was removed and the crude purified by SiO$_2$ column chromatography eluting with a CHCl$_3$/MeOH gradient (from 5 to 8% MeOH) to afford 45 mg (66%) of I-88 as a white solid.

$^{31}$P-NMR (MeOD; 202.5 MHz): δ 3.76, 3.65; $^1$H-NMR (MeOD; 500 MHz): δ 8.22, 8.21 (1H, 2s, H-8), 8.13-7.24 (131H, m, naphthyl, PhCH$_2$ and H-2), 6.28-6.26 (1H, m, H-1'), 5.09-5.01 (2H, m, PhCH$_2$), 4.92-4.89 (1H, m, H-2'), 4.67-4.64 (1H, m, H-3'), 4.39-4.28 (1H, m, H-5'), 4.06-4.01 (1H, m, CH$_3$CH), 1.30 (3H, d, $^3$J=7.05, CH$_3$CH); $^{13}$C-NMR (MeOD; 125.7 MHz): δ 20.20, 20.26, 20.38, 20.43 (CH$_3$CH), 51.68, 51.79 (CH$_3$CH), 67.97, 68.03 (PhCH$_2$), 68.75, 68.79, 68.91 (C-5'), 73.95, 74.08, 74.16 (C-2'+C+3'), 91.26, 91.37 (C-1'),99.18, 99.26 (C-4'), 116.16, 116.28, 116.30, 122.53, 122.66, 126.08, 126.30, 126.35, 126.47, 127.48, 127.57, 127.68, 127.73, 127.79, 127.83, 128.83, 128.93, 129.20, 129.24, 129.28, 129.52, 129.54, 136.16, 136.25, 137.10, 137.15 (naphthol, PhCH$_2$ and C-5), 141.29 (C-8), 146.85, 146.95 (C-2), 147.70, 147.76 ('ipso', naphthol), 149.83 (C-4), 158.81 (C-6), 174.82, 174.85 (COOBn).

EXAMPLE 85

Renilla Luciferase Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The Renilla luciferase gene was introduced into the first open reading frame of a replicon construct NK5.1 (Krieger et al., *J. Virol* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contain replicative HCV subgenomic RNA, and the activity of Renilla luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

Renilla luciferase HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960). All the reagents described in the following paragraph were included in the manufacturer's kit, and the manufacturer's instructions were followed for preparations of the reagents. The cells were washed twice with 200 μl of phosphate buffered saline (pH 7.0) (PBS) per well and lysed with 25 μl of 1×passive lysis buffer prior to incubation at room temperature for 20 min. One hundred microliters of LAR II reagent was added to each well. The plate was then inserted into the LB 96V microplate luminometer (MicroLumatPlus, Berthold), and 100 μl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microlitre of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

| Compound Number | Luciferase Activity $IC_{50}$ (μM) |
| --- | --- |
| I-34 | 0.382 |
| I-28 | 0.615 |
| I-13 | 0.754 |
| I-14 | 0.864 |
| I-35 | 0.991 |

EXAMPLE 86

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound according to formula I

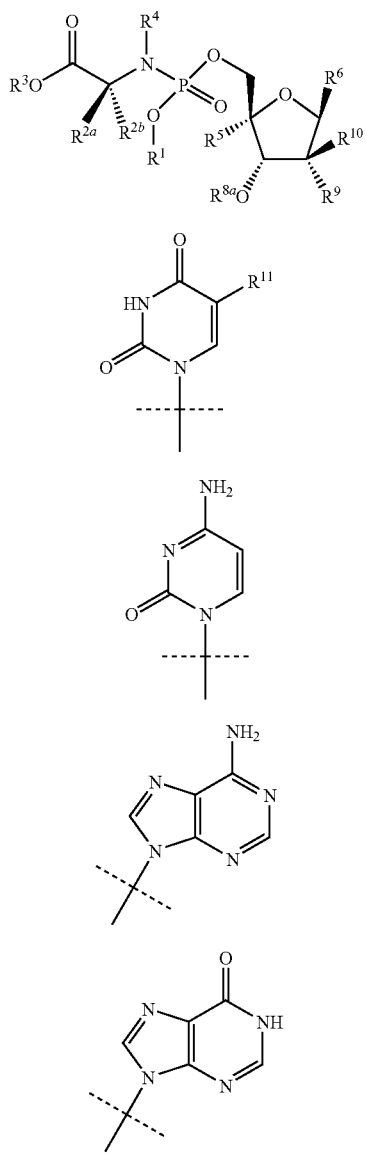

wherein:
$R^1$ is hydrogen or aryl wherein said aryl is phenyl or naphthyl optionally substituted with one to three substituents independently selected from the group consisting of $C_{1-6}$ alkyl, $C_{2-6}$ alkenyl, $C_{2-6}$ alkynyl, $C_{1-6}$ alkoxy, halogen, $C_{1-6}$ haloalkyl, $-N(R^{1a})_2$, $C_{1-6}$ acylamino, $-NHSO_2C_{1-6}$ alkyl, $-SO_2N(R^{1a})_2$, $-SO_2C_{1-6}$ alkyl, $COR^{1b}$, nitro and cyano;

$R^{1a}$ is independently hydrogen or $C_{1-6}$ alkyl;
$R^{1b}$ is $-OR^{1a}$ or $-N(R^{1a})_2$;
$R^{2a}$ and $R^{2b}$ are (i) independently selected from the group consisting of hydrogen, $C_{1-10}$ alkyl, $-(CH_2)_rNR^{1a}{}_2$, $C_{1-6}$ hydroxyalkyl, $-CH_2SH$, $-(CH_2)_2S(O)_pMe$, $-(CH_2)_3NHC(=NH)NH_2$, (1H-indol-3-yl)methyl, (1H-imidazol-4-yl)methyl, $-(CH_2)_mCOR^{1b}$, aryl and aryl $C_{1-3}$ alkyl, said aryl groups optionally substituted with a group selected from the group consisting of hydroxyl, $C_{1-10}$ alkyl, $C_{1-6}$ alkoxy, halogen, nitro and cyano,; (ii) $R^{2a}$ is hydrogen and $R^{2b}$ and $R^4$ together are $(CH_2)_3$; (iii) $R^{2a}$ and $R^{2b}$ together are $(CH_2)_n$; or, (iv) $R^{2a}$ and $R^{2b}$ both are $C_{1-6}$ alkyl;

$R^3$ is hydrogen, $C_{1-10}$ alkyl, $C_{1-10}$ haloalkyl, aryl or aryl-$C_{1-3}$ alkyl wherein said aryl is phenyl;
$R^4$ is hydrogen, $C_{1-3}$ alkyl, or $R^{2b}$ and $R^4$ together are $(CH_2)_3$;
$R^5$ is azide, $C\equiv CH$ or $-(Z)-CH=CHCl$;
$R^6$ is A, B, C or D wherein $R^{11}$ is hydrogen or $C_{1-3}$ alkyl;
$R^7$ is hydrogen, methyl, halomethyl or halogen;
either
(a) $R^9$ is $OR^{8b}$ and $R^{10}$ is hydrogen wherein $R^{8a}$ and $R^{8b}$ are (i) independently hydrogen, benzoyl or $C_{1-6}$ acyl or (i) together $R^{8a}$ and $R^{8b}$ are $C(Me)_2$, $C(CH_2)_4$, CHPh, or
(b) $R^9$ is hydrogen and $R^{10}$ is $OR^{8b}$ wherein $R^{8a}$ and $R^{8b}$ are independently hydrogen or $C_{1-6}$ acyl;

m is 0 to 3;
n is 4 or 5;
p is 0 to 2;
r is 1 to 6; and,
pharmacologically acceptable salts thereof.

2. A compound according to claim 1 wherein $R^3$ is hydrogen, $C_{1-10}$ alkyl, aryl or aryl-$C_{1-3}$ alkyl wherein said aryl is phenyl and $R^{11}$ is hydrogen.

3. A compound according to claim 2 wherein:
$R^{2a}$ and $R^{2b}$ are (i) independently hydrogen, methyl, iso-propyl, iso-butyl, sec-butyl, $-CH_2OH$, $-CH(OH)CH_3$, $-CH_2SH$, $-CH_2CH_2S(O)_pMe$, $-(CH_2)_mCOR^{1b}$ wherein m is 1 or 2, $-(CH_2)_r-NH_2$ wherein r is 3 or 4, $-(CH_2)_3-NHC(=NH)NH_2$, $-CH_2C_6H_5$, $-CH_2-p-C_6H_4-OH$, (3-indolinyl)methylene, (4-imidazolyl)methylene; (ii) $R^{2a}$ and $R^{2b}$ together are $(CH_2)_n$; or, (iii) $R^{2a}$ and $R^{2b}$ both are $C_{1-3}$ alkyl;
$R^3$ is hydrogen, $C_{1-10}$ alkyl or benzyl;
$R^9$ is $OR^{8b}$; and,
$R^4$, $R^7$, $R^{8a}$, $R^{8b}$ and $R^{10}$ are hydrogen.

4. A compound according to claim 3 wherein:
$R^{2a}$ is hydrogen and $R^{2b}$ is selected from the group consisting of hydrogen, methyl, iso-propyl, iso-butyl, sec-butyl, $-CH_2OH$, $-CH(OH)CH_3$, $-CH_2SH$, $-CH_2CH_2SMe$, $-(CH_2)_mCOR^{1b}$ wherein m is 1 or 2, $-(CH_2)_r-NH_2$ where r is 3 or 4, $-(CH_2)_3-NHC(=NH)NH_2$, $-CH_2C_6H_5$, $-CH_2-p-C_6H_4-OH$, (3-indolinyl)methylene, and (4-imidazolyl)methylene; and,
$R^5$ is azide or $C\equiv CH$.

5. A compound according to claim 4 wherein $R^{2b}$ is hydrogen, -Me, $-CH_2CH(Me)_2$, $-CH(Et)Me$ or $-CHMe_2$.

6. A compound according to claim 3 wherein both $R^{2a}$ and $R^{2b}$ are Me or $R^{2a}$ and $R^{2b}$ together are $(CH_2)_4$ and $R^5$ is azide or $C\equiv CH$.

7. A compound according to claim 2 wherein:
$R^{2a}$ and $R^{2b}$ are (i) independently hydrogen, methyl, iso-propyl, iso-butyl, sec-butyl, $-CH_2OH$, $-CH(OH)CH_3$, $-CH_2SH$, $-CH_2CH_2S(O)_pMe$, $-(CH_2)_mCOR^{1b}$ wherein m is 1 or 2, $-(CH_2)_r-NH_2$ wherein r is 3 or 4, $-(CH_2)_3-NHC(=NH)NH_2$, $-CH_2C_6H_5$, $-CH_2-p-C_6H_4-OH$, (3-indolinyl)methylene, (4-imidazolyl)methylene; (ii) $R^{2a}$ and $R^{2b}$ together are $(CH_2)_n$; or, (iii) $R^{2a}$ and $R^{2b}$ both are $C_{1-3}$ alkyl;
$R^3$ is $C_{1-10}$ alkyl or benzyl;
$R^{10}$ is $OR^{8b}$; and,
$R^4$, $R^7$, $R^{8a}$, $R^{8b}$ and $R^9$ are hydrogen.

8. A compound according to claim 7 wherein:
$R^{2a}$ is hydrogen and $R^{2b}$ is selected from the group consisting of hydrogen, methyl, iso-propyl, iso-butyl, sec-butyl, —$CH_2OH$, —$CH(OH)CH_3$, —$CH_2SH$, —$CH_2CH_2SMe$, —$(CH_2)_m COR^{1b}$ wherein m is 1 or 2, —$(CH_2)_r$—$NH_2$ wherein r is 3 or 4, —$(CH_2)_3$—NHC(=NH)$NH_2$, —$CH_2C_6H_5$, —$CH_2$-p-$C_6H_4$—OH, (3-indolinyl)methylene, and (4-imidazolyl)methylene; and, $R^5$ is azide or C≡CH.

9. A compound according to claim 8 wherein $R^{2b}$ is hydrogen, -Me, —$CH_2CH(Me)_2$, —CH(Et)Me or —$CHMe_2$.

10. A compound according to claim 7 wherein both $R^{2a}$ and $R^{2b}$ are Me or $R^{2a}$ and $R^{2b}$ together are $(CH_2)_4$ and $R^5$ is azide or C≡CH.

11. A method for inhibiting HCV replication in a cell comprising administering an effective amount of a compound according to claim 1.

12. A method for inhibiting HCV replication in a cell comprising administering an effective amount of a compound according to claim 4.

13. A pharmaceutical composition comprising an effective quantity of a compound according to claim 1 admixed with at least one pharmaceutically acceptable carrier, diluent, or excipient.

* * * * *